United States Patent
Sampath et al.

(10) Patent No.: US 9,650,428 B2
(45) Date of Patent: May 16, 2017

(54) METHODS AND COMPOSITIONS FOR TREATING CANCER

(71) Applicant: Roger Williams Hospital, Providence, RI (US)

(72) Inventors: Prakash Sampath, Lincoln, RI (US); Sadhak Sengupta, Sharon, MA (US); Richard P. Junghans, Boston, MA (US)

(73) Assignee: Roger Williams Hospital, Providence, RI (US)

( * ) Notice: Subject to any disclaimer, the term of this patent is extended or adjusted under 35 U.S.C. 154(b) by 0 days.

(21) Appl. No.: 14/956,299

(22) Filed: Dec. 1, 2015

(65) Prior Publication Data

US 2016/0151490 A1    Jun. 2, 2016

Related U.S. Application Data

(60) Provisional application No. 62/086,346, filed on Dec. 2, 2014.

(51) Int. Cl.
| | |
|---|---|
| *C07K 14/705* | (2006.01) |
| *C07K 14/54* | (2006.01) |
| *A61K 48/00* | (2006.01) |
| *C12N 9/10* | (2006.01) |

(52) U.S. Cl.
CPC ...... *C07K 14/70521* (2013.01); *A61K 48/005* (2013.01); *C07K 14/5437* (2013.01); *C12N 9/1007* (2013.01); *C07K 2319/02* (2013.01); *C07K 2319/03* (2013.01); *C07K 2319/33* (2013.01); *C12N 2740/13043* (2013.01)

(58) Field of Classification Search
None
See application file for complete search history.

(56) References Cited

U.S. PATENT DOCUMENTS

| | | | |
|---|---|---|---|
| 5,965,126 A * | 10/1999 | Pegg | A61K 38/45 424/93.21 |
| 2012/0148552 A1* | 6/2012 | Jensen | A61K 48/005 424/93.71 |
| 2016/0024175 A1* | 1/2016 | Chow | C07K 14/4748 424/278.1 |

FOREIGN PATENT DOCUMENTS

| | | |
|---|---|---|
| WO | WO 2014/164554 A1 | 10/2014 |
| WO | WO 2015/120363 A1 | 8/2015 |
| WO | WO 2016/089916 A1 | 6/2016 |

OTHER PUBLICATIONS

Dasgupta et al., "Engineered drug resistant immunocompetent cells enhance tumor cell killing during a chemotherapy challenge", Biochem. Biophys. Res. Commun., vol. 391, No. 1, pp. 170-175 (2010).
Debinski et al., "Receptor for Interleukin 13 is a Marker and Therapeutic Target for Human High-Grade Gliomas", Clin. Cancer Res., vol. 5, pp. 985-990 (1999).
Fontes et al., "Differential competitive resistance to methylating versus chloroethylating agents among five $O^6$-alkylguanine DNA alkyltransferases in human hematopoietic cells", Mol. Cancer Ther., vol. 5, No. 1, pp. 121-128 (2006).
Genbank: AAP36645.1, Homo sapiens O-6-methylguanine-DNA methyltransferase, partial [synthetic construct], 2 pages, Accessed on Jun. 13, 2016 from http://www.ncbi.nlm.nih.gov/protein/30584785.
International Search Report from PCT Patent Application No. PCT/US2015/063267 mailed May 13, 2016, application now published as International Publication No. WO2016/089916 on Jun. 9, 2016.
Kahlon et al, "Specific recognition and killing of glioblastoma multiforme by interleukin 13-zetakine redirected cytolytic cells", Cancer Res., vol. 64, pp. 9160-9166 (2004).
Kawakami et al., "Specifically targeted killing of interleukin-13 (IL-13) receptor-expressing breast cancer by IL-13 fusion cytotoxin in animal model of human disease", Mol. Cancer Ther., vol. 3, pp. 137-147 (2004).
Kong et al., "Suppression of human glioma xenografts with second-generation IL13R-specific chimeric antigen receptor-modified T cells", Clin. Cancer Res., vol. 18, pp. 5949-5960 (2012).
Krebs et al., "T cells redirected to interleukin-13Rα2 with interleukin-13 mutein—chimeric antigen receptors have anti-glioma activity but also recognize interleukin-13Rα1", Cytoyherapy, vol. 16, No. 8, pp. 1121-1131 (2014).
Madhankumar et al., "Interleukin-13 receptor-targeted nanovesicles are a potential therapy for glioblastoma multiforme", Mol. Cancer Ther., vol. 5, No. 12, pp. 3162-3169 (2006).
NCBI: NP_000631.1, Interleukin-13 receptor subunit alpha-2 precursor [Homo-sapiens], 3 pages, Accessed on Nov. 19, 2015 from http://www.ncbi.nim.nih.gov/protein/N_000631.1.
Radcliffe and Mitrophanous, "Multiple gene products from a single vector: 'self-cleaving' 2A peptides", Gene Therapy, vol. 11, pp. 1673-1674 (2004).

(Continued)

*Primary Examiner* — Addison D Ault
(74) *Attorney, Agent, or Firm* — McDermott Will & Emery LLP

(57) ABSTRACT

Described are compositions and methods relating to immune cells which express both a chimeric antigen receptor which binds to the IL13 receptor α-2 (IL13Rα2) and a $O^6$-methylguanine DNA methyltransferase (MGMT) protein. Viral particles containing an IL13 chimeric antigen receptor (IL13CAR) or variant thereof and an MGMT protein or variant thereof are used to transfect immune cells such as T cells, imparting to the transfected cells both IL13Rα2-targeting activity and resistance to the chemotherapeutic agent temozolomide (TMZ). The compositions and methods described are useful for cancer therapy such as the treatment of a high-grade malignant glioma.

32 Claims, 13 Drawing Sheets

(56) References Cited

OTHER PUBLICATIONS

Sawai et al., "Protection and in Vivo Selection of Hematopoietic Stem Cells Using Temozolomide, $O^6$-Benzylguanine, and an Alkyltransferase-Expressing Retroviral Vector", Mol. Ther., vol. 3, No. 1, pp. 78-87 (2001).

Sengupta et al., "Impact of temozolomide on immune response during malignant glioma chemotherapy", Clinical Dev. Immunol., Article ID: 831090, 7 pages (2012), Accessed from http://dx.doi.org/10.1155/2012/831090.

Sengupta et al., "Interleukin-13 receptor alpha 2-targeted glioblastoma immunotherapy", BioMed Res. Int., Article ID: 952128, 8 pages (2014), Accessed from http://dx.doi.org/10.1155/2014/952128.

Thaci et al., "Significance of interleukin-13 receptor alpha 2—targeted glioblastoma therapy", Neuro-Oncology, vol. 16, No. 10, pp. 1304-1312 (2014).

Woolford et al., "The P140K mutant of human O(6)-methylguanine-DNA-methyltransferase (MGMT) confers resistance in vitro and in vivo to temozolomide in combination with the novel MGMT inactivator O(6)-(4-bromothenyl)guanine", J. Gene Med., vol. 8, No. 1, pp. 29-34 (2006).

Zhang et al., "Identification, Purification, and Characterization of a Soluble Interleukin (IL)-13-binding Protein", J. Biol. Chem., vol. 272, No. 14, pp. 9747-9480 (1997).

\* cited by examiner

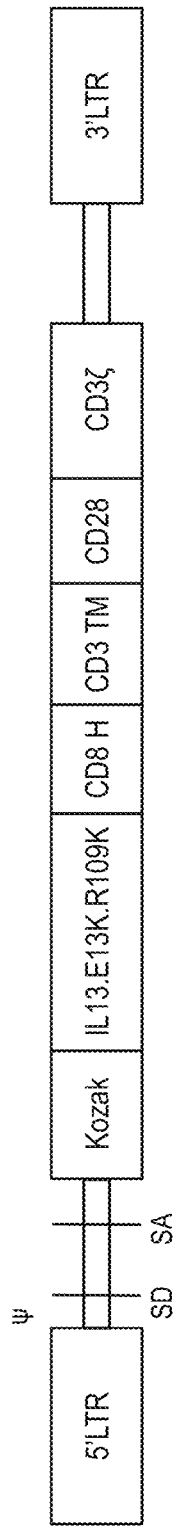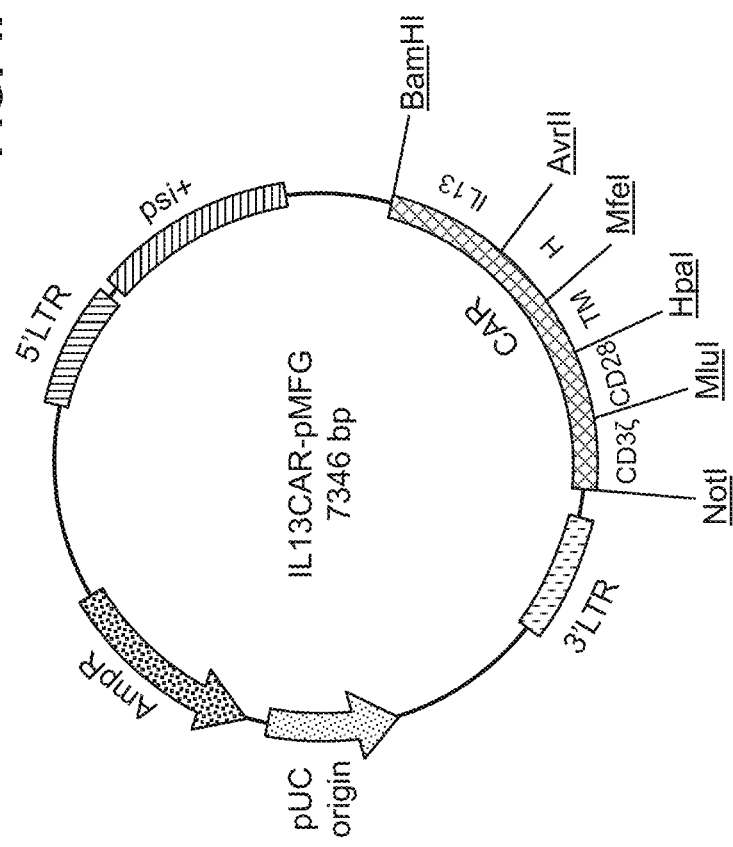
FIG. 1A
FIG. 1B

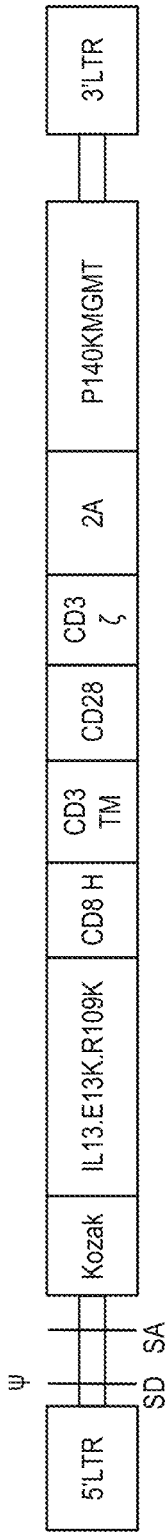
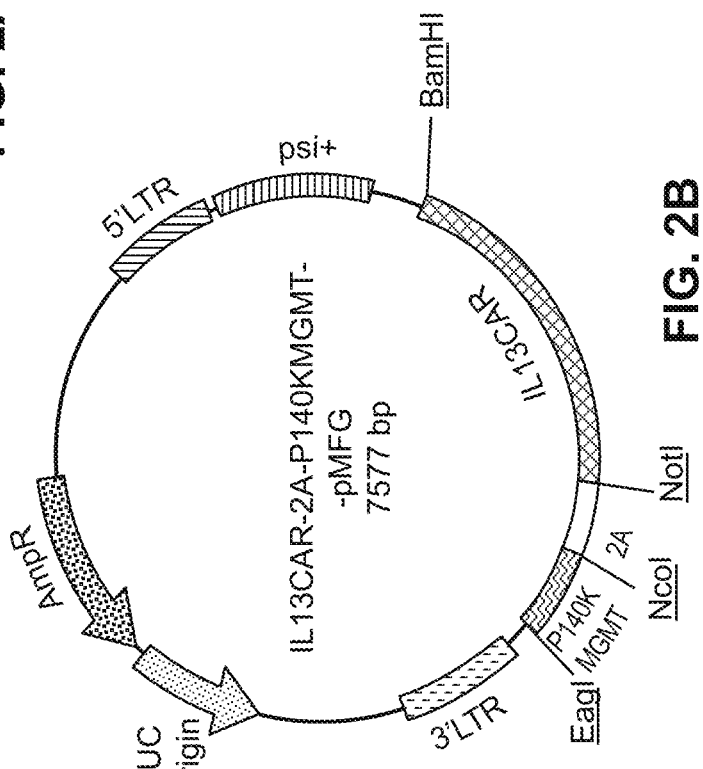
FIG. 2A
FIG. 2B

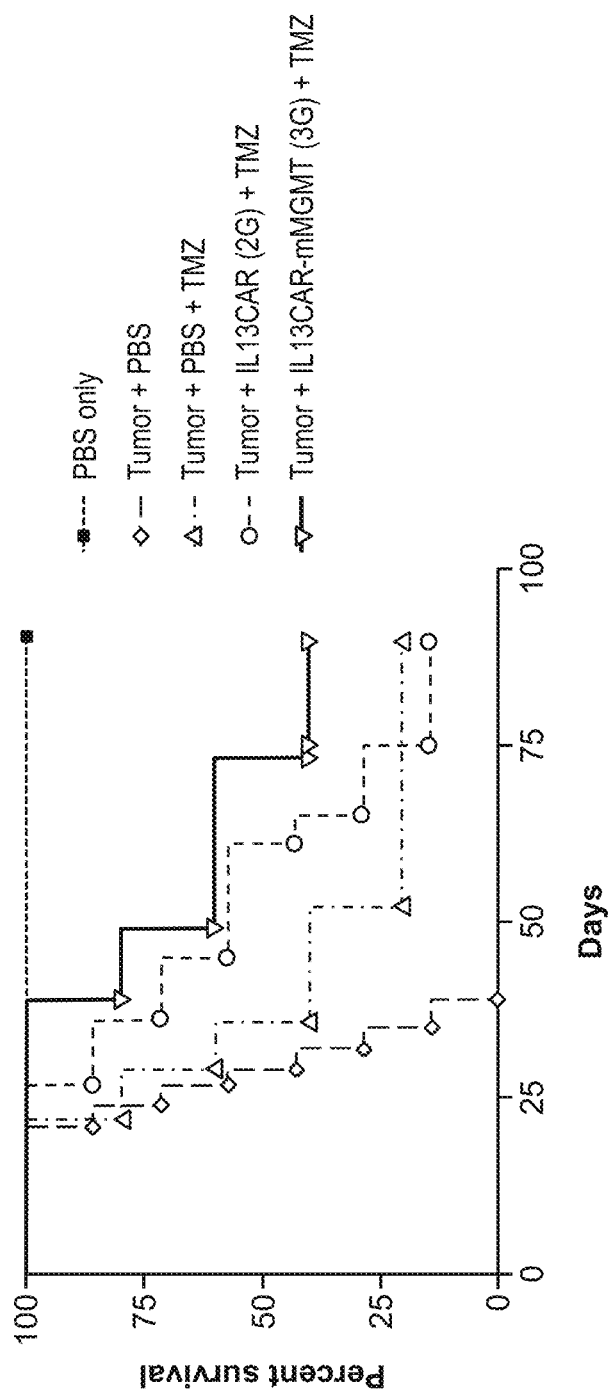

DNA Sequence of IL13CAR-P140KMGMT SEQ ID NO:1

| GGA TCC | GCC ACC | ATG | CAT CCG CTC CTC AAT CCT CTC CTG TTG GCA | Signal |
| CTG GGC CTC ATG GCG CTT TTG TTG ACC ACG TCA ATT GCT CTC ACT | |
| TGC CTT GGC GGC TTT GCC | TCC CCA GGC CCT GTG CCT CCC TCT ACA | |
| GCC CTC AGG GAG CTC ATT GAG GAG CTG GTC AAC ATC ACC CAG AAC | IL13(WT) |
| CAG AAG GCT CCG CTC TGC AAT GGC AGC ATG GTA TGG AGC ATC AAC | |
| CTG ACA GCT GGC ATG TAC TGT GCA GCC TGG AAT CCT GAT CAA C | |
| GTG TCA GGC TGC AGT GCC ATC GAG AAG ACC CAG AGG ATG CTG AGC | |
| GGA TTC TGC CCG CAC AAG GTC TCA GCT GGG CAG TTT TCC AGC TTG | |
| CAT GTC CGA GAC ACC AAA ATC GAG GTG GCC CAG TTT GTA AAG GAC | |
| CTG CTC TTA CAT TTA AAG AAA CTT TTT CGC GAG GGA CAG TTC AAC | |
| CCT AGG | AAG CCC ACC ACG ACG CCA GCG CCG CGA CCA CCA ACA CCG GCG | Hinge |
| CCC ACC ATC GCG TCG CAG CCC CTG TCC CTG CGC CCA GAG GCG TGC CGG | |
| CCA GCG GCG GGG GGC GCA GTG CAC ACG AGG GGG CTG GAC TTC GCC | |
| CAA TTG | CTC TGC TAC CTG CTG GAT GGA ATC CTC TTC ATC TAT GGT GTC | TM |
| ATT CTC ACT GCC TTG TTC CTG AGA GTG | GTT AAC | TTC TGG GTG AGG AGT | |
| AAG AGG AGC AGG CTC CTG CAC AGT GAC TAC ATG AAC ATG ACT CCC CGC | CD28 |
| CGC CCC GGG CCC ACC CGC AAG CAT TAC CAG CCC TAT GCC CCA CCA CGC | |
| GAC TTC GCA GCC TAT CGC | TCC ACG | CGT AAG TTC AGC AGG AGC GCA GAC | |
| GCC CCC GCG TAC CAG CAG GGC CAG AAC CAG CTC TAT AAC GAG CTC AAT | |
| CTA GGA CGA AGA GAG GAG TAC GAT GTT TTG GAC AAG AGA CGT GGC CGG | |
| GAC CCT GAG ATG GGG GGA AAG CCG AGA AGG AAG AAC CCT CAG GAA GGC | CD3ζ |
| CTG TAC AAT GAA CTG CAG AAA GAT AAG ATG GCG GAG GCC TAC AGT GAG | |
| ATT GGG ATG AAA GGC GAG CGC CGG AGG GGC AAG GGG CAC GAT GGC CTT | |
| TAC CAG GGT CTC AGT ACA GCC ACC AAG GAC ACC TAC GAC GCC CTT CAC | |
| ATG CAG GCC CTG CCC CCT CGC | TAA | CAG CCA | GCG GCC GC | A | GAG GGC AGA | A2 |
| GGA AGT CTT CTA ACA TGC GGT GAC GTG GAG GAG AAT CCC GGC CCT | CCA | |
| TGG | ATG | GAC AAA GAT TGC GAG ATG AAG CGG ACC ACA CTG GAT TCC CCC | |
| CTG GGC AAA CTG GAG CTG TCT GGC TGT GAA CAG GGG CTG CAC GAG ATC | |
| AAA CTG CTG GGA AAG GGC ACT AGC GCC GCT GAT GCT GTG GAA GTG CCA | |
| GCT CCA GCT GCT GTG CTG GGA GGA CCT GAG CCA CTG ATG CAG TGC ACC | |
| GCC TGG CTG AAC GCT TAC TTC CAT CAG CCT GAA GCC ATC GAG GAA TTT | |
| CCC GTG CCT GCC CTG CAC CAT CCA GTG TTC CAG CAG GAG AGT TTT ACA | |
| AGG CAG GTG CTG TGG AAG CTG CTG AAA GTG GTG AAG TTC GGG GAA GTG | P140K |
| ATT TCC TAC CAG CAG CTG GCT GCT CTG GCT GGA AAC CCA AAA GCT GCT | MGMT |
| CGG GCC GTG GGA GGA GCT ATG AGA GGC AAT CCA GTG | AAA | ATC CTG ATT | |
| CCC TGC CAC AGG GTG GTG TGT AGC TCC GGA GCT GTG GGG AAC TAT TCT | |
| GGG GGA CTG GCC GTG AAA GAA TGG CTG CTG GCT CAC GAG GGA CAT AGG | |
| CTG GGA AAG CCT GGC CTG GGA GGG TCT AGT GGA CTG GCT GGA GCT TGG | |
| CTG AAG GGA GCT GGA GCT ACC TCA GGA AGC CCA CCT GCC GGC CGG AAT | |
| TGA | CGG CCG | |

FIG. 7A

Peptide Sequence of IL13CAR-P140KMGMT  SEQ ID NO:4

| | |
|---|---|
| MHPLLNPLLLALGLMALLLTTVIALTCLGGFA SPGPVPPSTALRELIEELVNITQNQKAPL CNGSMVWSINLTAGMYCAALESLINVSGCSAIEKTQRMLSGFCPHKVSAGQFSSLHVR DTKIEVAQFVKDLLLHLKKLFREGQFN | IL13 |
| PR KPTTTPAPRPPTPAPTIASQPLSLRPEAC RPAAGGAVHTRGLDFA | Hinge |
| QL LCYLLDGILFIYGVILTALFLRV VN FWVRSKRSRLLHSDYM | TM/CD28 |
| NMTPRRPGPTRKHYQPYAPPRDFAAYRS TR KFSRSADAPAYQQGQNQLYNELNLGR REEYDVLDKRRGRDPEMGGKPRRKNPQEGLYNELQKDKMAEAYSEIGMKGERRRGK GHDGLYQGLSTATKDTYDALHMQALPPR STOP | CD3ζ |
| QP AAA EGRGSLLTCGDVEENPGP M | A2 |
| DKDCEMKRTTLDSPLGKLELSGCEQGLHEIKLLGKGTSAADAVEVPAPAAVLGGPEPL MQCTAWLNAYFHQPEAIEEFPVPALHHPVFQQESFTRQVLWKLLKVVKFGEVISYQQL AALAGNPKAARAVGGAMRGNPV K LIPCHRVVCSSGAVGNYSGGLAVKEWLLAHEGH RLGKPGLGGSSGLAGAWLKGAGATSGSPPAGRN STOP | P140K MGMT |

FIG. 7B

DNA Sequence of IL13 (E13Y) CAR-P140KMGMT  SEQ ID NO:2

| Sequence | Region |
|---|---|
| GGA TCC \| GCC ACC \| ATG \| CAT CCG CTC CTC AAT CCT CTC CTG TTG GCA CTG GGC CTC ATG GCG CTT TTG TTG ACC ACG TCA TTG CTC TCA CT TGC CTT GGC GGC TTT GCC \| | Signal |
| TCC CCA GGC CCT GTG CCT CCC TCT ACA GCC CTC AGG TAC CTC ATT GAG GAG CTG GTC AAC ATC ACC CAG AAC CAG AAG GCT CCG CTC TGC AAT GGC AGC ATG GTA TGG AGC ATC AAC CTG ACA GCT GGC ATG TAC TGT GCA GCC CTG GAA TCC CTG ATC AAC GTG TCA GGC TGC AGT GCC ATC GAG AAG ACC CAG AGG ATG CTG AGC GGA TTC TGC CCG CAC AAG GTC TCA GCT GGG CAG TTT TCC AGC TTG CAT GTC CGA GAC ACC AAA ATC GAG GTG GCC CAG TTT GTA AAG GAC CTG CTC TTA CAT TTA AAG AAA CTT TTT CGC GAG GGA CAG TTC AAC | IL13(E13y) |
| CCT AGG \| AAG CCC ACC ACG ACG CCA GCG CCG CGA CCA CCA ACA CCG GCG CCC ACC ATC GCG TCG CAG CCC CTG TCC CTG CGC CCA GAG GCG TGC CGG CCA GCG GCG GGG GGC GCA GTG CAC ACG AGG GGG CTG GAC TTC GCC | Hinge |
| CAA TTG \| CTC TGC TAC CTG CTG GAT GGA ATC CTC TTC ATC TAT GGT GTC ATT CTC ACT GCC TTG TTC CTG AGA GTG \| GTT AAC \| | TM |
| TTC TGG GTG AGG AGT AAG AGG AGC AGG CTC CTG CAC AGT GAC TAC ATG AAC ATG ACT CCC CGC CGC CCC GGG CCC ACC CGC AAG CAT TAC CAG CCC TAT GCC CCA CCA CGC GAC TTC GCA GCC TAT CGC \| TCC ACG \| | CD28 |
| CGT AAG TTC AGC AGG AGC GCA GAC GCC CCC GCG TAC CAG CAG GGC CAG AAC CAG CTC TAT AAC GAG CTC AAT CTA GGA CGA AGA GAG GAG TAC GAT GTT TTG GAC AAG AGA CGT GGC CGG GAC CCT GAG ATG GGG GGA AAG CCG AGA AGG AAG AAC CCT CAG GAA GGC CTG TAC AAT GAA CTG CAG AAA GAT AAG ATG GCG GAG GCC TAC AGT GAG ATT GGG ATG AAA GGC GAG CGC CGG AGG GGC AAG GGG CAC GAT GGC CTT TAC CAG GGT CTC AGT ACA GCC ACC AAG GAC ACC TAC GAC GCC CTT CAC ATG CAG GCC CTG CCC CCT CGC \| TAA \| CAG CCA \| GCG GCC GC \| A \| GAG GGC AGA | CD3ζ / A2 |
| GGA AGT CTT CTA ACA TGC GGT GAC GTG GAG GAG AAT CCC GGC CCT \| CCA TGG \| ATG \| | |
| GAC AAA GAT TGC GAG ATG AAG CGG ACC ACA CTG GAC TCC CCC CTG GGC AAA CTG GAG CTG TCT GGC TGT GAA CAG GGG CTG CAC GAG ATC AAA CTG CTG GGA AAG GGC ACT AGC GCC GCT GAT GCT GTG GAA GTG CCA GCT CCA GCT GCT GTG CTG GGA GGA CCT GAG CCA CTG ATG CAG TGC ACC GCC TGG CTG AAC GCT TAC TTC CAT CAG CCT GAA GCC ATC GAG GAA TTT CCC GTG CCT GCC CTG CAC CAT CCA GTG TTC CAG CAG GAG AGT TTT ACA AGG CAG GTG CTG TGG AAG CTG CTG AAA GTG GTG AAG TTC GGG GAA GTG ATT TCC TAC CAG CAG CTG GCT GCT CTG GCT GGA AAC CCA AAA GCT GCT CGG GCC GTG GGA GGA GCT ATG AGA GGC AAT CCA GTG \| AAA \| ATC CTG ATT CCC TGC CAC AGG GTG GTG TGT AGC TCC GGA GCT GTG GGG AAC TAT TCT GGG GGA CTG GCC GTG AAA GAA TGG CTG CTG GCT CAC GAG GGA CAT AGG CTG GGA AAG CCT GGC CTG GGA GGG TCT AGT GGA CTG GCT GGA GCT TGG CTG AAG GGA GCT GGA GCT ACC TCA GGA AGC CCA CCT GCC GGC CGG AAT \| TGA \| CGG CCG \| | P140K MGMT |

FIG. 8A

Peptide Sequence of IL13 (E13Y) CAR-P140KMGMT SEQ ID NO:5

| | |
|---|---|
| MHPLLNPLLLALGLMALLLTTVIALTCLGGFA SPGPVPPSTALRYLIEELVNITQNQKAPL CNGSMVWSINLTAGMYCAALESLINVSGCSAIEKTQRMLSGFCPHKVSAGQFSSLHVR DTKIEVAQFVKDLLLHLKKLFREGQFN | IL13 (E13y) |
| PR KPTTTPAPRPPTPAPTIASQPLSLRPEAC | Hinge |
| RPAAGGAVHTRGLDFA QL LCYLLDGILFIYGVILTALFLRV VN FWVRSKRSRLLHSDYM | TM/CD28 |
| NMTPRRPGPTRKHYQPYAPPRDFAAYRS TR KFSRSADAPAYQQGQNQLYNELNLGR REEYDVLDKRRGRDPEMGGKPRRKNPQEGLYNELQKDKMAEAYSEIGMKGERRRGK GHDGLYQGLSTATKDTYDALHMQALPPR | CD3ζ |
| STOP QP AAA EGRGSLLTCGDVEENPGP M | A2 |
| DKDCEMKRTTLDSPLGKLELSGCEQGLHEIKLLGKGTSAADAVEVPAPAAVLGGPEPL MQCTAWLNAYFHQPEAIEEFPVPALHHPVFQQESFTRQVLWKLLKVVKFGEVISYQQL AALAGNPKAARAVGGAMRGNPV K ILIPCHRVVCSSGAVGNYSGGLAVKEWLLAHEGH RLGKPGLGGSSGLAGAWLKGAGATSGSPPAGRN STOP | P140K MGMT |

FIG. 8B

DNA Sequence of IL13 (E13K,R109K) CAR-P140KMGMT SEQ ID NO:3

| Sequence | Region |
|---|---|
| GGA TCC \| GCC ACC \| ATG \| CAT CCG CTC CTC AAT CCT CTC CTG TTG GCA CTG GGC CTC ATG GCG CTT TTG TTG ACC ACG GTC ATT GCT CTC ACT TGC CTT GGC GGC TTT GCC \| | Signal |
| TCC CCA GGC CCT GTG CCT CCC TCT ACA GCC CTC AGG AAG CTC ATT GAG GAG CTG GTC AAC ATC ACC CAG AAC CAG AAG GCT CCG CTC TGC AAT GGC AGC ATG GTA TGG AGC ATC AAC CTG ACA GCT GGC ATG TAC TGT GCA GCC CTG GAA TCC CTG ATC AAC GTG TCA GGC TGC AGT GCC ATC GAG AAG ACC CAG AGG ATG CTG AGC GGA TTC TGC CCG CAC AAG GTC TCA GCT GGG CAG TTT TCC AGC TTG CAT GTC CGA GAC ACC AAA ATC GAG GTG GCC CAG TTT GTA AAG GAC CTG CTC TTA CAT TTA AAG AAA CTT TTT AAG GAG GGA CAG TTC AAC | IL13 (E13K R109K) |
| CCT AGG \| AAG CCC ACC ACG ACG CCA GCG CCG CGA CCA CCA ACA CCG GCG CCC ACC ATC GCG TCG CAG CCC CTG TCC CTG CGC CCA GAG GCG TGC CGG CCA GCG GCG GGG GGC GCA GTG CAC ACG AGG GGG CTG GAC TTC GCC | Hinge |
| CAA TTG \| CTC TGC TAC CTG CTG GAT GGA ATC CTC TTC ATC TAT GGT GTC ATT CTC ACT GCC TTG TTC CTG AGA GTG \| | TM |
| GTT AAC \| TTC TGG GTG AGG AGT AAG AGG AGC AGG CTC CTG CAC AGT GAC TAC ATG AAC ATG ACT CCC CGC CGC CCC GGG CCC ACC CGC AAG CAT TAC CAG CCC TAT GCC CCA CCA CGC GAC TTC GCA GCC TAT CGC \| TCC ACG \| | CD28 |
| CGT AAG TTC AGC AGG AGC GCA GAC GCC CCC GCG TAC CAG CAG GGC CAG AAC CAG CTC TAT AAC GAG CTC AAT CTA GGA CGA AGA GAG GAG TAC GAT GTT TTG GAC AAG AGA CGT GGC CGG GAC CCT GAG ATG GGG GGA AAG CCG AGA AGG AAG AAC CCT CAG GAA GGC CTG TAC AAT GAA CTG CAG AAA GAT AAG ATG GCG GAG GCC TAC AGT GAG ATT GGG ATG AAA GGC GAG CGC CGG AGG GGC AAG GGG CAC GAT GGC CTT TAC CAG GGT CTC AGT ACA GCC ACC AAG GAC ACC TAC GAC GCC CTT CAC ATG CAG GCC CTG CCC CCT CGC \| TAA \| CAG CCA \| GCG GCC GC \| A \| GAG GGC AGA GGA AGT CTT CTA ACA TGC GGT GAC GTG GAG GAG AAT CCC GGC CCT \| CCA | CD3ζ |
| | A2 |
| TGG \| ATG \| GAC AAA GAT TGC GAG ATG AAG CGG ACC ACA CTG GAC TCC CCC CTG GGC AAA CTG GAG CTG TCT GGC TGT GAA CAG GGG CTG CAC GAG ATC AAA CTG CTG GGA AAG GGC ACT AGC GCC GCT GAT GCT GTG GAA GTG CCA GCT CCA GCT GCT GTG CTG GGA GGA CCT GAG CCA CTG ATG CAG TGC ACC GCC TGG CTG AAC GCT TAC TTC CAT CAG CCT GAA GCC ATC GAG GAA TTT CCC GTG CCT GCC CTG CAC CAT CCA GTG TTC AGC AGG AGA GTT TTT ACA AGG CAG GTG CTG TGG AAG CTG CTG AAA GTG GTG AAG TTC GGG GAA GTG ATT TCC TAC CAG CAG CTG GCT GCT CTG GCT GGA AAC CCA AAA GCT GCT CGG GCC GTG GGA GGA GCT ATG AGA GGC AAT CCA GTG \| AAA \| ATC CTG ATT CCC TGC CAC AGG GTG GTG TGT AGC TCC GGA GCT GTG GGG AAC TAT TCT GGG GGA CTG GCC GTG AAA GAA TGG CTG CTG GCT CAC GAG GGA CAT AGG CTG GGA AAG CCT GGC CTG GGA GGG TCT AGT GGA CTG CTG GAG CTT GGG CTG AAG GGA GCT GGA GCT ACC TCA GGA AGC CCA CCT GCC GGC CGG AAT TGA \| CGG CCG | P140K MGMT |

FIG. 9A

Peptide Sequence of IL13 (E13K.R109K) CAR-P140KMGMT SEQ ID NO:6

| | |
|---|---|
| MHPLLNPLLLALGLMALLLTTVIALTCLGGFA | IL13 |
| SPGPVPPSTALRKLIEELVNITQNQKAPL CNGSMVWSINLTAGMYCAALESLINVSGCSAIEKTQRMLSGFCPHKVSAGQFSSLHVR DTKIEVAQFVKDLLLHLKKLFKEGQFN | (E13K R109K) |
| PR | |
| KPTTTPAPRPPTPAPTIASQPLSLRPEAC | Hinge |
| RPAAGGAVHTRGLDFA | |
| QL | |
| LCYLLDGILFIYGVILTALFLRV | TM/CD28 |
| VN | |
| FWVRSKRSRLLHSDYM NMTPRRPGPTRKHYQPYAPPRDFAAYRS | |
| TR | |
| KFSRSADAPAYQQGQNQLYNELNLGR REEYDVLDKRRGRDPEMGGKPRRKNPQEGLYNELQKDKMAEAYSEIGMKGERRRGK GHDGLYQGLSTATKDTYDALHMQALPPR | CD3ζ |
| STOP | |
| QP | |
| AAA | |
| EGRGSLLTCGDVEENPGP | A2 |
| M | |
| DKDCEMKRTTLDSPLGKLELSGCEQGLHEIKLLGKGTSAADAVEVPAPAAVLGGPEPL MQCTAWLNAYFHQPEAIEEFPVPALHHPVFQQESFTRQVLWKLLKVVKFGEVISYQQL AALAGNPKAARAVGGAMRGNPV | P140K MGMT |
| K | |
| LIPCHRVVCSSGAVGNYSGGLAVKEWLLAHEGH RLGKPGLGGSSGLAGAWLKGAGATSGSPPAGRN | |
| STOP | |

FIG. 9B

METHODS AND COMPOSITIONS FOR TREATING CANCER

CROSS-REFERENCE TO RELATED APPLICATION

This application claims the benefit of priority to U.S. provisional application No. 62/086,346, filed Dec. 2, 2014, which is hereby incorporated by reference in its entirety.

CROSS-REFERENCE TO A SEQUENCE LISTING

A "Sequence Listing" is submitted with this application in the form of a text file, created Dec. 1, 2015, and named "0962018010US00seqlist.txt" (69000 bytes), the contents of which are incorporated herein by reference in their entirety.

BACKGROUND OF THE INVENTION

Targeted immunotherapy has thus emerged as promising field of research in the treatment of malignancies and has received a great deal of interest in recent years (Carpentier and Meng, 2006, Curr Opin Oncol, 18(6):631-636; Wainwright et al., 2012, Exp Opin Emerging Drugs; 17(2):181-202). One of the most extensively studied targets is the interleukin-13 receptor alpha 2 (IL13Rα2) (Thaci et al., 2014, Neuro-Oncol, 16(10):1304-1324). IL13Rα2 is a decoy receptor for interleukin-13 (IL13), lacking the signaling chain that is present on the ubiquitous IL13Rα1, thus preventing any IL13-mediated downstream signaling pathway (Arima et al., 2005, J Biol Chem, 280(26):24915-24922). Increased expression of IL13Rα2 has been reported to promote tumor progression in glioma and other tumor models. IL13Rα2 expression is a prognostic marker for glioma malignancy grade and for poor patient survival (Brown et al., 2013, PLoS ONE, 8(10): Article ID e77769). Its selective expression on MG, discovered almost two decades ago, has been a target for therapy ever since (Debinski et al., 1999, Clin Canc Res, 5(5):985-990).

Glioblastoma is the most common primary brain tumor in adults. More than half of the 18,000 patients diagnosed with malignant primary brain tumors in US each year have glioblastoma multiforme. Glioblastoma multiforme is an anaplastic, highly cellular tumor, with high proliferation indices, microvascular proliferation and focal necrosis. Signs and symptoms depend on several factors (size, rate of growth, localization of the tumor within the brain) and are mainly represented by headache, seizures, neurological deficits, changes in mental status. Glioblastoma multiforme prognosis remains dismal. Survival time is less than 2 years for the majority of patients.

Despite incremental improvements in survival with the current standard of care for glioblastoma (GBM), which is a tripartite regimen of surgery, radiotherapy, and chemotherapy (Rolle et al., 2010, Neurosurgery Clin of North America, 21(1):201-214; Ashby and Ryken, 2006, Neurosurgical focus, 20(4):E3), the prognosis for most patients remains dismal (Stupp et al, 2009, Lancet Oncol, 10(5):459-466; Omuro and DeAngelis, 2013, JAMA, 310(17):1842-1850). Major limitations in the treatment of GBM are the tumor's location within the brain that impedes delivery of cytotoxic agents across the blood-brain barrier (Ashby and Ryken, 2006, Neurosurgical Focus, 20(4):E3), compounded with a strong immunosuppressive environment (Rolle et al., 2012, Adv Exp Med Biol, 746:53-76) and chemo- and radioresistant glioma-initiating cells (Bao et al, 2006, Nature, 444(7120):756-760; Frosina, Mol Canc Res, 2009 7(7):989-999). As a result, novel strategies are continually being tested to improve patient survival, quality of life, and overall outcomes.

Accordingly, described herein are compositions and methods for more efficacious treatment of cancers in which malignant cells express or over-express IL13Rα2, including brain cancers.

SUMMARY OF THE INVENTION

In one aspect, a chimeric nucleic acid sequence is provided, wherein the chimeric nucleic acid sequence comprises a first nucleic acid which encodes an IL13 chimeric antigen receptor (IL13CAR) which binds the IL1Rα2 receptor (IL13Rα2) and a second nucleic acid which encodes a drug-resistance polypeptide which is a $O^6$-methylguanine DNA methyltransferase (MGMT) protein.

In one embodiment, the IL13CAR comprises a ligand to the IL13Rα2. In another embodiment, the ligand is IL13. In yet another embodiment, the ligand is a fragment of IL13 which binds the IL13Rα2. In still another embodiment, the ligand is an antibody variable domain or fragment thereof which selectively binds IL13Rα2.

In one embodiment, the MGMT protein comprises a P140K substitution.

In one embodiment, the chimeric nucleic acid sequence comprises a first nucleic acid sequence encoding the IL13CAR and a second nucleic acid sequence encoding the MGMT protein.

In one embodiment, the first nucleic acid sequence encoding the IL13CAR is 5' to the second nucleic acid sequence encoding the MGMT polypeptide. In an alternative embodiment, the first nucleic acid sequence encoding the IL13CAR is 3' to the second nucleic acid sequence encoding the MGMT polypeptide.

In one embodiment, the first nucleic acid sequence encoding the IL13CAR comprises in a 5' to 3' direction: a nucleic acid sequence encoding an IL13Rα2 ligand domain, a nucleic acid sequence encoding a transmembrane (TM) domain, and a nucleic acid sequence encoding a cytoplasmic domain which comprises a CD3 zeta signaling domain. In another embodiment, the first nucleic acid sequence further comprises a nucleic acid sequence which encodes a hinge region, wherein the hinge region positioned between the IL13 ligand domain and the TM domain. In still another embodiment, the first nucleic acid sequence further comprises a nucleic acid sequence which encodes a CD28 co-stimulatory domain wherein the CD28 co-stimulatory domain is positioned between the TM domain and the CD3-zeta chain. In still another embodiment, the first nucleic acid sequence further comprises a nucleic acid which encodes a signal sequence wherein the signal sequence is positioned N-terminal to the IL13Rα2 ligand domain.

In one embodiment, the hinge domain is a CD8 hinge domain. In another embodiment, the CD8 hinge domain comprises SEQ ID NO:27.

In one embodiment, the cytoplasmic domain further comprises one or more co-stimulatory domains. In one embodiment, the co-stimulatory domain is a CD28 co-stimulatory domain. In another embodiment, the CD28 co-stimulatory domain is positioned between the TM domain and the CD3-zeta signaling domain.

In one embodiment, the cytoplasmic domain further comprises one or more co-stimulatory domains selected from the group consisting of an OX-40 costimulatory domain, an HVEM co-stimulatory domain, a 41BB co-stimulatory domain, an ICOS co-stimulatory domain, an OX40 co-stimulatory domain and a CD27 co-stimulatory domain. In one embodiment, the additional co-stimulatory domain is positioned between a CD28 co-stimulatory domain and a CD3-zeta signaling domain.

In one embodiment, the signal sequence is a heterologous signal sequence. In another embodiment, the signal sequence is an IL13 signal sequence or a variant thereof. In still another embodiment, the IL13 signal sequence comprises SEQ ID NO:25. In yet another embodiment, the nucleic acid sequence encoding the signal sequence comprises SEQ ID NO:9.

In one embodiment, the IL13 ligand binding domain comprises the mature IL13 protein (SEQ ID NO:26). In another embodiment, the IL13 ligand binding domain consists of a fragment of the mature IL13 wherein the fragment binds to the IL13Rα2 protein with approximately the same affinity as does the mature IL13 protein (SEQ ID NO:26).

In one embodiment, the nucleic acid sequence encoding the IL13 ligand encodes a polypeptide selected from the group consisting of SEQ ID NO:26, SEQ ID NO:36 and SEQ ID NO:37. In another embodiment, the nucleic acid sequence encoding the mature IL13 polypeptide comprises a nucleic acid sequence selected from the group consisting of SEQ ID NO:10, SEQ ID NO:34, and SEQ ID NO:35.

In one embodiment, the first nucleic acid comprises in a 5' to 3' direction, a nucleic acid selected from the group consisting of SEQ ID NO:10, SEQ ID NO:34, or SEQ ID NO:35 which encodes the IL13 ligand domain, a nucleic acid comprising SEQ ID NO:14 or a variant thereof which encodes the TM domain, and a nucleic acid comprising SEQ ID NO:18 or a variant thereof which encodes the CD3-zeta signaling domain. In another embodiment, the first nucleic acid further comprises SEQ ID NO:9 or a variant thereof which encodes the IL13 signal sequence wherein the sequence of SEQ ID NO:9 is upstream of the nucleic acid sequence encoding the IL13 ligand domain. In another embodiment, the first nucleic acid further comprises SEQ ID NO:12 or a variant thereof which encodes the CD8 hinge domain. In still another embodiment, the first nucleic acid further comprises the nucleic acid of SEQ ID NO:16 or a variant thereof which encodes the CD28 co-stimulatory domain.

In one embodiment, the first nucleic acid comprises in a 5' to 3' direction, the nucleic acid sequence of SEQ ID NO:9 or variant thereof which encodes the signaling domain, a nucleic acid selected from the group consisting of SEQ ID NO:10, SEQ ID NO:34, or SEQ ID NO:35 which encodes the IL13 ligand domain, the nucleic acid sequence of SEQ ID NO:12 or a variant thereof which encodes the CD8 hinge domain, a nucleic acid comprising SEQ ID NO:14 or a variant thereof which encodes the TM domain, the nucleic acid of SEQ ID NO:16 or a variant thereof which encodes the CD28 co-stimulatory domain and the nucleic acid sequence of SEQ ID NO:18 or a variant thereof which encodes the CD3-zeta signaling domain.

In one embodiment, the first nucleic acid sequence encoding the CAR further comprises a nucleic acid sequence encoding a linker between the mature IL13 ligand and the CD8 hinge domain. In another embodiment, the nucleic acid sequence encoding the linker between the mature IL13 ligand and the CD8 hinge domain consists of SEQ ID NO:11.

In one embodiment, the first nucleic acid sequence encoding the CAR further comprises a nucleic acid sequence encoding a linker between SEQ ID NO:12 and SEQ ID NO:14. In another embodiment, the nucleic acid sequence encoding the linker between SEQ ID NO:12 and SEQ ID NO:14 consists of SEQ ID NO:13.

In one embodiment, the first nucleic acid sequence encoding the CAR further comprises a nucleic acid sequence encoding a linker between SEQ ID NO:14 and SEQ ID NO:16. In another embodiment, the nucleic acid sequence encoding the linker between SEQ ID NO:14 and SEQ ID NO:16 consists of SEQ ID NO:15.

In one embodiment, the first nucleic acid sequence encoding the CAR further comprises a nucleic acid sequence encoding a linker between SEQ ID NO:16 and SEQ ID NO:18. In another embodiment, the nucleic acid sequence encoding the linker between SEQ ID NO:16 and SEQ ID NO:18 consists of SEQ ID NO:17.

In one embodiment, the second nucleic acid sequence encoding the MGMT protein comprises P140KMGMT (SEQ ID NO:22). In another embodiment, the second nucleic acid sequence encoding the MGMT protein comprises a nucleic acid sequence which encodes a protein comprising SEQ ID NO:33.

In one embodiment, the second nucleic acid sequence encoding the MGMT protein comprises an amino acid sequence selected from the group consisting of G156A-MGMT (SEQ ID NO:38), MGMT-2 (SEQ ID NO:39), MGMT-3 (SEQ ID NO:40) and MGMT-5 (SEQ ID NO:41). In another embodiment, the second nucleic acid sequence encoding the MGMT protein comprises a nucleic acid sequence which encodes a protein comprising G156A-MGMT (SEQ ID NO:38), MGMT-2 (SEQ ID NO:39), MGMT-3 (SEQ ID NO:40) and MGMT-5 (SEQ ID NO:41).

In one embodiment, the second nucleic sequence encoding the MGMT protein does not comprise SEQ ID NO:48. In another embodiment, the second nucleic acid sequence encodes an MGMT protein that does not comprise SEQ ID NO:49.

In one embodiment, the chimeric nucleic acid sequence further comprises a nucleic acid sequence encoding a self-cleaving peptide. In another embodiment, the nucleic acid sequence encoding the self-cleaving peptide comprises SEQ ID NO:21. In still another embodiment, the self-cleaving peptide comprises the amino acid sequence of SEQ ID NO:32.

In one embodiment, the chimeric nucleic acid sequence further comprises a Kozak sequence. In another embodiment, the Kozak sequence comprises SEQ ID NO:8. In still another embodiment, the Kozak sequence is located upstream of the nucleic acid sequences which encode the IL13CAR and the MGMT proteins. In one embodiment, the chimeric nucleic acid sequence further comprises a first restriction endonuclease site which is upstream of the Kozak sequence. In another embodiment, the restriction endonuclease site upstream of the Kozak sequence consists of SEQ ID NO:7. In one embodiment, the chimeric nucleic acid sequence further comprises a second endonuclease site which is downstream of the nucleic acid sequences which encode the IL13CAR and the MGMT proteins.

In one embodiment, the chimeric nucleic acid sequence comprises a nucleotide sequence selected from the group consisting of nucleotides 109 to 1836 of SEQ ID NO:1, nucleotides 109 to 1836 of SEQ ID NO:2 and nucleotides 109 to 1836 of SEQ ID NO:3. In one embodiment, the chimeric nucleic acid sequence comprises a nucleotide sequence selected from the group consisting of nucleotides 13 to 1836 of SEQ ID NO:1, nucleotides 13 to 1836 of SEQ ID NO:2 and nucleotides 13 to 1836 of SEQ ID NO:3. In one embodiment, the chimeric nucleic acid sequence comprises a nucleotide sequence selected from the group consisting of nucleotides 7 to 1842 of SEQ ID NO:1, nucleotides 7 to 1842 of SEQ ID NO:2 and nucleotides 7 to 1842 of SEQ ID NO:3. In another embodiment, the chimeric nucleic acid sequence comprises a nucleotide sequence selected from the group consisting of SEQ ID NO:1, SEQ ID NO:2 and SEQ ID NO:3.

In one embodiment, the chimeric nucleic acid sequence comprises a nucleotide sequence which encodes the protein of SEQ ID NO:4, SEQ ID NO:5, SEQ ID NO:6, SEQ ID NO:45, SEQ ID NO:46 or SEQ ID NO:47.

In one embodiment, the IL13Rα2 receptor ligand is a variant of IL-13 or fragment thereof which binds the IL13Rα2 with about 5-fold, 10-fold, or 100-fold less affinity than wild-type IL13 (SEQ ID NO:26). In an alternative embodiment, the IL13Rα2 receptor ligand is a variant of IL13 or fragment thereof which binds the IL13Rα2 with about 5-fold, 10-fold, or 100-fold higher affinity than wild-type IL13 (SEQ ID NO:26).

In one embodiment, the IL13Rα2 receptor ligand is not identical to wild-type IL-13. In another embodiment, IL13Rα2 receptor ligand is not identical to SEQ ID NO:26.

In one embodiment, P140KMGMT protein is effective in increasing in vitro and/or in vivo viability of a cell expressing the drug-resistance polypeptide when a cell transfected with an IL13-CAR-T is treated with a chemotherapeutic agent as compared to the cell treated with the chemotherapeutic but not expressing the drug-resistance polypeptide.

In one embodiment, the IL13Rα2 receptor ligand is not identical to wild-type IL-13. In another embodiment, IL13Rα2 receptor ligand is not identical to SEQ ID NO:26.

In another aspect, a vector comprising a nucleic acid sequence which encodes the IL13CAR and MGMT protein as described herein is provided.

In one embodiment, the vector comprises a monocistronic nucleic acid sequence which encodes an IL13CAR, a self-cleaving peptide, and a MGMT protein as described herein. In another embodiment, the self-cleaving peptide comprises a 2A peptide.

In an alternative embodiment, the vector comprises a polycistronic chimeric nucleic acid sequence which encodes an IL13CAR and an MGMT protein. In another embodiment the polycistronic chimeric nucleic acid sequence which encodes the IL13CAR and the MGMT protein further comprises an internal ribosome entry site (IRES) positioned between the nucleic acid sequence encoding the IL13CAR and the nucleic acid sequence encoding the MGMT protein. In still another embodiment, the polycistronic chimeric nucleic acid sequence which encodes the IL13CAR and the MGMT protein further comprises a promoter positioned between the nucleic acid sequence encoding the IL13CAR and the nucleic acid sequence encoding the MGMT protein.

In one embodiment, the vector is a bacterial plasmid vector. In another embodiment, the vector is an expression vector.

In one embodiment, the vector is a viral vector. In another embodiment, the viral vector is selected from the group consisting of a retroviral vector, a lentiviral vector, an adenoviral vector and an adeno-associated viral vector.

In another aspect, a cell transfected with a vector comprising a chimeric nucleic acid sequence which encodes a chimeric antigen receptor (CAR) and a drug-resistance polypeptide as described herein is provided.

In one embodiment, the cell is selected from the group consisting of a T-cell, an NK-cell, and NKT-cell.

In another, a recombinant polypeptide is provided comprising in an N-terminal to C-terminal direction, a ligand which binds to a tumor antigen, a transmembrane domain, and a cytoplasmic signaling domain as described herein.

In one embodiment, the recombinant polypeptide comprising, in an N-terminal to C-terminal direction, a ligand which binds to a tumor antigen, a transmembrane domain, and a cytoplasmic signaling domain, further comprises a self-cleaving peptide positioned between the CAR and drug resistance polypeptide. In another embodiment, the drug resistance polypeptide is N-terminal to the CAR. In still another embodiment, the drug resistance polypeptide is C-terminal to the CAR.

In another aspect, a recombinant polypeptide is provided comprising a modified MGMT polypeptide which increases viability of a cell exposed to TMZ, wherein the cell is genetically modified to express a CAR as described herein and wherein the cell is administered to a patient diagnosed with a brain cancer.

In another aspect, a composition comprising a first nucleic acid which encodes a CAR as described herein and a second nucleic acid which encodes an MGMT protein as described herein is provided.

In one embodiment, the first nucleic acid encodes a CAR protein which comprises an IL13 ligand domain as described herein, a TM domain as described herein, and a cytoplasmic domain comprising a CD3-zeta signaling domain as described herein. In another embodiment, the first nucleic acid further encodes a signal sequence which is upstream of the IL13 ligand binding domain of the CAR protein. In still another embodiment, the first nucleic acid further encodes a hinge region as described herein wherein the hinge region is positioned between the IL13 ligand domain and the TM domain of the CAR protein. In yet another embodiment, the first nucleic acid further encodes a CD28 co-stimulatory domain which is positioned between the TM domain and the CD3-zeta signaling domain. In still another embodiment, the first nucleic acid further encodes an additional co-stimulatory domain. In another embodiment, the first nucleic acid further comprises a Kozak sequence upstream of the nucleic acid encoding the CAR protein.

In one embodiment, the second nucleic acid encodes an MGMT protein which has an amino acid sequence selected from the group consisting of SEQ ID NO:33, SEQ ID NO:38, SEQ ID NO:39, SEQ ID NO:40, SEQ ID NO:41 and SEQ ID NO:43.

In one embodiment, the MGMT protein does not comprise SEQ ID NO:49.

In one embodiment, the composition comprises a chimeric nucleic acid which comprises the first nucleic acid and the second nucleic acid.

In one embodiment, the chimeric nucleic acid further comprises a nucleic acid which encodes a self-cleaving linker peptide as described herein, wherein the nucleic acid encoding the self-cleaving linker peptide is positioned between the first nucleic acid and the second nucleic acid.

In one embodiment, the chimeric nucleic acid further comprises an internal ribosome entry site (IRES) as described herein, wherein the IRES is positioned between the first nucleic acid and the second nucleic acid.

In one embodiment, the chimeric nucleic acid is a bicistronic construct which comprises a first promoter upstream of the first nucleic acid encoding the CAR protein and a second promoter upstream of the second nucleic acid encoding the MGMT protein.

In one embodiment, the composition comprises a first vector which comprises the first nucleic acid which encodes the CAR protein and a second vector which comprises the second nucleic acid which encodes the MGMT protein. In another embodiment, the first and second vectors are each a plasmid or expression vector. In yet another embodiment, the first and second vectors are each a retroviral particle.

In another aspect, a host cell comprising a first nucleic acid which encodes a CAR as described herein and a second nucleic acid which encodes an MGMT protein as described herein. In one embodiment, the first nucleic acid encodes a CAR protein which comprises an IL13 ligand domain as described herein, a TM domain as described herein, and a cytoplasmic domain comprising a CD3-zeta signaling domain as described herein. In another embodiment, the first nucleic acid further encodes a signal sequence which is upstream of the IL13 ligand binding domain of the CAR protein. In still another embodiment, the first nucleic acid further encodes a hinge region as described herein wherein the hinge region is positioned between the IL13 ligand domain and the TM domain of the CAR protein. In yet another embodiment, the first nucleic acid further encodes a CD28 co-stimulatory domain which is positioned between the TM domain and the CD3-zeta signaling domain. In still another embodiment, the first nucleic acid further encodes an additional co-stimulatory domain. In another embodiment, the first nucleic acid further comprises a Kozak sequence upstream of the nucleic acid encoding the CAR protein.

In one embodiment, the second nucleic acid encodes an MGMT protein which has an amino acid sequence selected from the group consisting of SEQ ID NO:33, SEQ ID NO:38, SEQ ID NO:39, SEQ ID NO:40, SEQ ID NO:41 and SEQ ID NO:43. In another embodiment, the MGMT protein is not SEQ ID NO:49.

In one embodiment, the host cell comprises a chimeric nucleic acid which comprises the first nucleic acid and the second nucleic acid.

In one embodiment, the chimeric nucleic acid further comprises a nucleic acid which encodes a self-cleaving linker peptide as described herein, wherein the nucleic acid encoding the self-cleaving linker peptide is positioned between the first nucleic acid and the second nucleic acid.

In one embodiment, the chimeric nucleic acid further comprises an internal ribosome entry site (IRES) as described herein, wherein the IRES is positioned between the first nucleic acid and the second nucleic acid.

In one embodiment, the chimeric nucleic acid is a dicistronic construct which comprises a first promoter upstream of the first nucleic acid encoding the CAR protein and a second promoter upstream of the second nucleic acid encoding the MGMT protein.

In one embodiment, the host cell comprises a first vector which comprises the first nucleic acid which encodes the CAR protein and a second vector which comprises the second nucleic acid which encodes the MGMT protein. In another embodiment, the first and second vectors are each a plasmid or expression vector as described herein. In yet another embodiment, the first and second vectors are each a retroviral particle as described herein.

In another aspect, a composition comprising a recombinant polypeptide is provided, wherein the recombinant polypeptide comprises in an N-terminal to C-terminal direction, a signal sequence as described herein, an IL13 ligand as described herein, a transmembrane domain as described herein, a cytoplasmic signaling domain as described herein, an MGMT protein as described herein and a pharmaceutically acceptable excipient. In another embodiment, the recombinant polypeptide further comprises a hinge domain as described herein wherein the hinge domain is positioned between the IL13 ligand domain and the transmembrane domain. In still another embodiment, the recombinant polypeptide further comprises a self-cleaving peptide as described herein wherein the self-cleaving peptide is positioned between the cytoplasmic signaling domain and the MGMT protein.

In one embodiment, the composition is a pharmaceutical composition.

In another aspect, a method for treating a subject diagnosed with a cancer is provided.

In one embodiment, the method comprises obtaining a cell from the subject, transducing the cell with one or more nucleic acids which encode an IL13CAR as described herein and an MGMT protein as described herein, maintaining the cell under conditions in which the nucleic acids are expressed by the cell, and administering to the patient a therapeutically effective number of the cells expressing the IL13CAR and MGMT proteins.

In one embodiment, the introducing into the cell comprises using a first vector comprising a nucleic acid encoding the IL13CAR and a second vector comprising a nucleic acid encoding the MGMT protein. In another embodiment, the introducing into the cell comprises using a vector that comprises a nucleic acid encoding the IL13CAR and the MGMT protein.

In one embodiment, the cell is transduced with a vector comprising an IL13CAR-P140KMGMT chimeric construct as described herein.

In one embodiment the subject is a mammal. In another embodiment, the mammal is a primate, a human, or a mouse.

In one embodiment, the one or more nucleic acids are introduced into the cell using a viral vector selected from the group consisting of a retroviral vector, a lentiviral vector, an adenoviral vector or a combination thereof.

In one embodiment, the cell is a T cell.

In one embodiment, the T cells are obtained using plasmapheresis.

In one embodiment, the subject has been diagnosed with a cancer selected from the group consisting of brain, breast, pancreatic, head and neck, ovarian and colorectal. In another embodiment, the cancer has metastasized.

In one embodiment, the subject has been diagnosed with a high-grade malignant glioma. In another embodiment, the subject has been diagnosed with glioblastoma multiforme (GMB), an anaplastic astrocytoma or a pediatric glioma.

In one embodiment, the brain cancer is a glioblastoma. In another embodiment, the brain cancer is a high-grade astrocytoma.

In one embodiment, the breast cancer is a basal-like breast cancer.

In one embodiment, the method further comprises treating the subject with one or more chemotherapeutic agents. In another embodiment, the method comprises treating the subject with temozolomide (TMZ).

In one embodiment, the one or more chemotherapeutic agents is administered to the subject before, during, and/or after administration of a dose of the modified cells.

In one embodiment, the administering is intracranial, intramedullary, intradermally, subcutaneously, topically, or intravenously.

In another aspect, a method for producing a cell which expresses an IL13CAR-P140KMGMT construct as described herein is provided comprising introducing into the cell a nucleic acid sequence encoding the IL13CAR-P140KMGMT chimeric protein, maintaining the cell under conditions in which the IL13CAR-P140KMGMT chimeric protein is expressed by the cell.

In one embodiment the cell is a mammalian cell. In another embodiment, the mammalian cell is a human cell, a primate cell or a mouse cell.

In one embodiment, the cell is a T cell. In another embodiment, the cell is an autologous cell or a human leukocyte antigen (HLA)-matched cell.

In one embodiment, the cell is obtained from one or more subjects diagnosed with a brain cancer or malignancy.

In another aspect, a population of cells comprising the IL13CAR-P140KMGMT construct is provided. In another embodiment, at least about 50%, 60%, 70%, 80T, 90% or 95% of cells in the population of cells express the IL13CAR-P140KMGMT construct is provided.

In one aspect, the invention is directed to an (one or more) isolated nucleic acid sequence encoding (having; comprising; consisting essentially of; consisting of) a chimeric antigen receptor (CAR) comprising (consisting essentially of; consisting of) a T cell receptor that expresses one or more ligands (e.g., an antibody) to one or tumor antigens of a brain cancer. In some aspects, the CAR further expresses one or more additional agents useful for treating a brain cancer.

In another aspect, the invention is directed to an expression construct comprising (consisting essentially of; consisting of) one or more nucleic acid sequences encoding a CAR comprising a T cell receptor that expresses one or more ligands (e.g., an antibody) of one or tumor antigens of a brain cancer (e.g., a cancer antigen-binding domain). In some aspects, the CAR further expresses one or more additional agents useful for treating a brain cancer.

In another aspect, the invention is directed to a host cell comprising (consisting essentially of; consisting of) an expression construct comprising one or more nucleic acid sequences encoding a CAR comprising a T cell receptor that expresses one or more ligands (e.g., an antibody) of one or tumor antigens of a brain cancer. In some aspects, the CAR further expresses one or more additional agents useful for treating a brain cancer.

In another aspect, the invention is directed to a method of producing a cell which expresses a CAR comprising (consisting essentially of; consisting of) a T cell receptor comprising one or more ligands (e.g., an antibody) of one or tumor antigens of a brain cancer. In a particular aspect, the CAR further comprises one or more additional agents useful for treating a brain cancer.

In another aspect, the invention is directed to a CAR polypeptide comprising (having; consisting essentially of; consisting of) a T cell receptor comprising one or more ligands (e.g., an antibody) of one or tumor antigens of a brain cancer. In a particular aspect, the CAR polypeptide further comprises one or more additional agents useful for treating a brain cancer.

In another aspect, the invention is directed to a method of treating brain cancer in an individual in need thereof comprising (consisting essentially of; consisting of) administering one or more T cells that express a CAR comprising a T cell receptor that expresses one or more ligands (e.g., an antibody) of one or tumor antigens of a brain cancer. In some aspects, the CAR further expresses one or more additional agents useful for treating a brain cancer.

The invention is also directed to pharmaceutical compositions comprising compositions provided herein.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A provides a schematic of an IL13E13K.R109K CAR nucleic acid construct.

FIG. 1B provides a plasmid map of a pMFG host plasmid comprising an IL13E13K.R109K CAR.

FIG. 2A provides a schematic of an IL13.E13KR109K CAR-2A-P140KMGMT.

FIG. 2B: provides a plasmid map of a pMFG host plasmid comprising an IL-13-CAR-2A-P140KMGMT.

FIG. 3C illustrates western blot analysis of cell lysates.

FIG. 6 illustrates viability of mice harboring a tumor and administered chimeric constructs and/or a chemotherapeutic agent as described herein.

FIGS. 7A-7B provide the chimeric nucleic acid sequence (FIG. 7A; SEQ ID NO:1) and amino acid sequence (FIG. 7B; SEQ ID NO:4) of an IL13CAR-P140KMGMT construct.

FIGS. 8A-8B provide the chimeric nucleic acid sequence (FIG. 8A; SEQ ID NO:2) and amino acid sequence (FIG. 8B; SEQ ID NO:5) of an IL13(E13Y)CAR-P140KMGMT construct.

FIGS. 9A-9B provide the chimeric nucleic acid sequence (FIG. 9A; SEQ ID NO:3) and amino acid sequence (FIG. 9B; SEQ ID NO:6) of an IL13(E13K.R109K)CAR-P140KMGMT construct.

DETAILED DESCRIPTION OF THE INVENTION

Figure 3A:
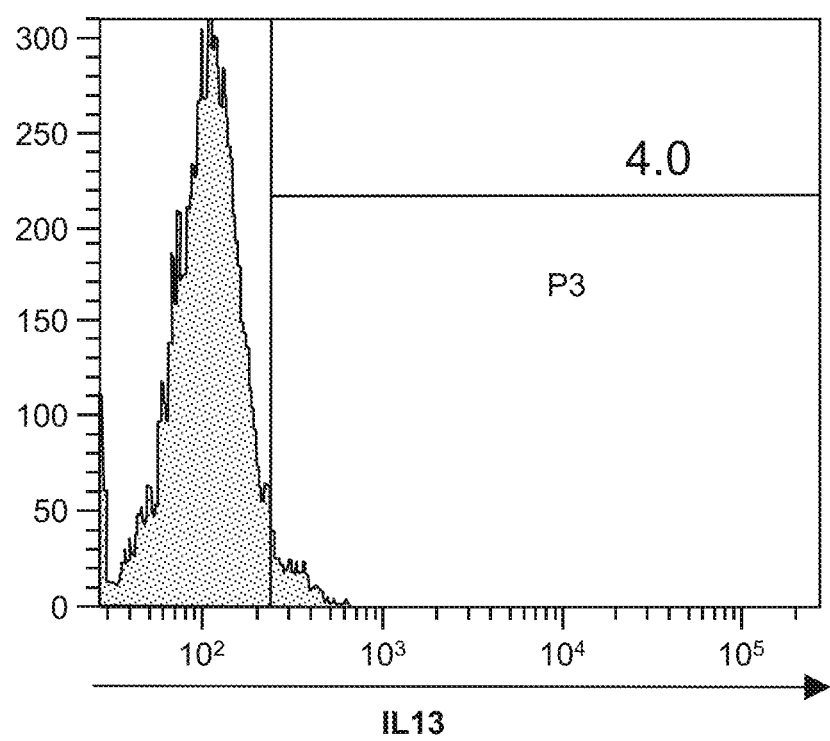
FIGS. 3A-3C illustrate FACS analysis of PG13 cells transduced with a virus containing an IL13CAR construct and a IL13CAR-2A-P140KMGMT construct, prior to enrichment (FIG. 3A) and after enrichment (FIG. 3B).

Described herein is the generation of a (one or more) chimeric antigen receptor (CAR) comprising a T cell receptor modified by genetic engineering to express one or more ligands (e.g., an antibody or other ligand to a cell surface protein) to one or more tumor antigens of a cancer. Specifically, the CAR proteins described herein include a ligand binding domain which binds to a protein which is expressed on the surface of a cancer cell. Preferably, the tumor antigen is not expressed on the surface of non-diseased or normal cells, or is expressed on non-diseased or normal cells at a level which is much lower than the level at which it is expressed on a cancer or other diseased cell. T cells modified to express the resulting CAR are redirected by the neo-specificity of the CAR to attack tumors expressing the surface antigen (e.g., a receptor) recognized by the CAR. Also shown herein is that the CAR can further comprise one or more additional agents useful for treating a brain cancer (e.g., an agent that overcomes the resistance of brain cancer cells to treatment). Specifically, the compositions and methods described herein are designed to treat brain cancers in which the malignant cells express the IL13α2 receptor (IL13Rα2). Accordingly, the disclosure is exemplified herein using a CAR that expresses and displays a ligand of the IL13Rα2, such as the cytokine interleukin 13 (IL13) or a variable domain of an antibody which selectively binds IL13Rα2. The IL13CAR is expressed with an O(6)-methylguanine-DNA-methyltransferase (MGMT) gene. In one embodiment, the MGMT gene is modified to encode a protein which imparts to or enhances a host cell's (e.g. T cell) resistance to temozolomide (TMZ), a chemotherapeutic agent used to treat brain cancer.

In one preferred embodiment, the IL13CAR comprises an IL13 which is mutated at position 13 (numbering relative to SEQ ID NO:26) to change glutamate to tyrosine. In an alternate preferred embodiment, the IL13 is mutated at position 13 to change glutamate to lysine and at position 109 to change arginine to lysine (amino acid positions 13 and 109 are with respect, e.g., to SEQ ID NO:26). In one embodiment, the IL13 is mutated so that the amino acid at position 109 is changed from arginine to lysine.

In one preferred embodiment, the modified MGMT gene encodes a MGMT variant referred to herein as P140KMGMT (SEQ ID N0:33), which protects IL13CAR-P140KMGMT-expressing T cells from cytotoxicity caused by treatment with a methylating agent such as TMZ.

In one embodiment, the IL13CAR and P140KMGMT proteins are expressed from a monocistronic construct which is transcribed to produce a single transcript which encodes a single protein comprising in an N-terminal to C-terminal direction: IL13CAR, a self-cleaving peptide (2A), and P140KMGMT. After translation of this fusion protein, cleavage of the self-cleaving peptide results in a P140KMGMT protein localized primarily to the nucleus and the IL13CAR, wherein the IL13 ligand domain is displayed on the surface of the host cell. However, it is understood that the IL13CAR and P140KMGMT proteins can be expressed from individual nucleic acids. For example, the nucleic acids encoding the IL12CAR and P140KMGMT proteins may be in separate vectors which are then introduced into the same cell, or they can be cloned into a single vector as individual monocistronic constructs (e.g., each having their own promoter).

T cells transduced with an IL13CAR-2A-P140KMGMT construct survived better when compared to IL13CAR-transduced T cells which did not express P140KMGMT, in the presence of TMZ (e.g., Example 6; FIG. 6). Accordingly, also disclosed herein are nucleic acid sequences encoding the CAR and drug resistance polypeptides (MGMT proteins), one or more nucleic acid or retroviral vectors comprising the nucleic acids, cells transfected or transduced with the one or more vectors, and methods for enhancing viability of genetically modified T cells which are exposed to a chemotherapeutic such as TMZ by co-expressing a modified MGMT gene in the modified T cell.

Also envisioned is a method for treating a subject diagnosed with a cancer, wherein the cancer includes cells which express IL13Rα2. For example, a brain cancer such as a high-grade malignant glioma and basal-like breast cancer cells overexpress the IL13Rα2 protein relative to non-diseased or non-cancerous cells of the same tissue. The claimed compositions are particularly useful when in which the subject is administered both a methylating chemotherapeutic agent and genetically modified immune cell (e.g., T cell) which expresses both an IL13CAR and a modified MGMT gene. This method can reduce treatment time and achieve glioma abolition faster and more effectively than if the subject were treated with only the chemotherapeutic or with the genetically modified T cell. Accordingly, in one aspect, the invention is directed to an (one or more) isolated nucleic acid sequence which encode a chimeric antigen receptor (CAR) for use in a T cell that expresses one or more ligands (e.g., an antibody) to one or tumor antigens of a cancer. In some aspects, the T cell further expresses one or more additional agents useful for treating a brain cancer.

DEFINITIONS

As used herein a "chimeric antigen receptor (CAR)" refers to a molecule comprising one or more extracellular cancer antigen-binding domains, one or more transmembrane domains and one or more cytoplasmic signaling domains for T-cell activation, and which has specificity for cells expressing the cancer ligand (e.g., the cancer antigen). When introduced into a T cell, the CAR redirects the specificity of the T cell. In a particular aspect, the CAR is expressed as a single molecule.

As used herein, a "cancer antigen-binding domain" refers to a domain that binds one or more antigens expressed by a cancer cell (one or more cancer antigens). In a particular aspect, the cancer antigen-binding domain is a binding domain that specifically (selectively) binds a cancer antigen and does not bind a non-specific target not expressed by a non-cancer cell (e.g., a normal cell, a healthy cell, a wild type cell).

A variety of cancer antigen-binding domains can be used and can be produced using known methods or obtained from commercial sources. The cancer antigen-binding domain can be, for example, a nucleic acid, a peptide (protein), an antibody, an organic molecule, a synthetic molecule and the like. Such cancer antigen-binding domains can be, for example, derived from libraries and/or obtained from natural sources.

The term "IL13CAR" as used herein encompasses a CAR which comprises an IL13 ligand as described herein or as known in the art, including but not limited to variants of IL13 (including, but not limited to functional fragments of IL13 (e.g., fragments of IL13 that can bind to IL13Rα2)), and other IL13 ligands such as an immunoglobulin domain which selectively binds IL13Rα2. Similarly, the term "MGMT" as used herein encompasses a wildtype MGMT and any MGMT variant as described herein or as known in the art.

As used herein the term "therapeutically effective" applied to dose or amount refers to that quantity of a compound or pharmaceutical composition (e.g., a composition comprising immune cells such as T lymphocytes and/or NK cells) comprising a chimeric receptor of the disclosure, and further comprising a drug resistance polypeptide that is sufficient to result in a desired activity upon administration to a subject in need thereof. Within the context of the present disclosure, the term "therapeutically effective" refers to that quantity of a compound or pharmaceutical composition that is sufficient to delay the manifestation, arrest the progression, relieve or alleviate at least one symptom of a disorder treated by the methods of the present disclosure. Note that when a combination of active ingredients is administered the effective amount of the combination may or may not include amounts of each ingredient that would have been effective if administered individually.

The phrase "pharmaceutically acceptable" as used in connection with compositions of the present disclosure refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "subject" refers to any mammal. In a preferred embodiment, the subject is human.

In other aspects, the cancer antigen-binding domain is all or a biologically active portion of an antibody. The term "antibody" as used herein refers to immunoglobulin molecules and immunologically active portions of immunoglobulin molecules, i.e., molecules that contain an antigen binding site that selectively binds an antigen. As used herein, "selectively binds" refers to the ability of the antibody to bind to an antigen or a fragment thereof and the inability to substantially bind to other molecules (e.g., antigens) in a sample. Examples of immunologically active portions of immunoglobulin molecules include Fab fragments (e.g., F(ab), F(ab')$_2$), variable fragments (e.g., single chain variable (scFv), di-scFv, single domain antibody fragment (sdAb), bi-specific fragments (e.g., bi-specific T cell engagers (BiTE)). Such fragments can be obtained from commercial sources and/or generated by, for example, treating the antibody with an enzyme such as pepsin.

The antibody can be a polyclonal or monoclonal antibody that binds (e.g., selectively binds) to one or more antigens expressed by a cancer cell. As used herein, a "polyclonal antibody" is an antibody from a collection of antibodies that bind to a specific antigen, each identifying a different epitope. As used herein, a "monoclonal antibody" or "monoclonal antibody composition" refers to a population of antibody molecules that contain only one species of an antigen binding site capable of immunoreacting with a particular epitope of one or more antigens. A monoclonal antibody composition thus typically displays a single binding affinity for a particular antigen with which it immunoreacts.

Polyclonal antibodies can be prepared as described above by immunizing a suitable subject with one or more desired cancer antigens such as the extracellular domain of the IL13Rα2 protein. The antibody titer in the immunized subject can be monitored over time by standard techniques, such as with an enzyme linked immunosorbent assay (ELISA) using immobilized polypeptide. If desired, the antibody molecules directed against the cancer antigen can be isolated from the mammal (e.g., from tissue, blood) and further purified by well-known techniques, such as protein A chromatography to obtain the IgG fraction. A person having ordinary skill in the art would be able to make a polyclonal antibody that selectively binds to the extracellular domain of the IL13Rα2 protein.

At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, Nature 256:495-497 (1975), the human B cell hybridoma technique (Kozbor et al., Immunol. Today 4:72 (1983)), the EBV-hybridoma technique (Cole et al., Monoclonal Antibodies and Cancer Therapy, Alan R. Liss, Inc., pp. 77-96 (1985)) or trioma techniques. The technology for producing hybridomas is well known (see generally Current Protocols in Immunology, Coligan et al., (eds.) John Wiley & Sons, Inc., New York, N.Y. (1994)). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well-known protocols used for fusing lymphocytes and immortalized cell lines can be applied for the purpose of generating a monoclonal antibody to a cancer antigen (see, e.g., Current Protocols in Immunology, supra; Galfre et al., Nature, 266:55052 (1977); R. H. Kenneth, in Monoclonal Antibodies: A New Dimension In Biological Analyses, Plenum Publishing Corp., New York, N.Y. (1980); and Lerner, Yale J. Biol. Med. 54:387-402 (1981)). Moreover, the ordinarily skilled worker will appreciate that there are many variations of such methods that also would be useful.

In one alternative to preparing monoclonal antibody-secreting hybridomas, a monoclonal antibody to a cancer antigen can be identified and isolated by screening a recombinant combinatorial immunoglobulin library (e.g., an antibody phage display library) with the polypeptide to thereby isolate immunoglobulin library members that bind the cancer antigen. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology 9:1370-1372 (1991); Hay et al., Hum. Antibod. Hybridomas 3:81-85 (1992); Huse et al., Science 246:1275-1281 (1989); and Griffiths et al., EMBO J. 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

Any of the above routine methods for generating polyclonal antibodies or monoclonal antibodies can be readily applied to a method for generating a monoclonal antibody which selectively binds to the extracellular domain of the IL13Rα2 protein. The variable domain of the resultant antibody or fragment thereof can then be used to generate an IL13 ligand domain which binds to the IL13Rα2 protein with an affinity about the same as the affinity with which the IL13 ligand domain (SEQ ID NO:26) binds the IL13Rα2 protein.

Constructs of the Invention

The invention is based, at least in part, on an immune cell expressing a CAR which is specific for IL13Rα2, where the cell is resistant to a chemotherapeutic agent, such as TMZ.

In certain embodiments, the invention provides a nucleic acid (also referred to herein as a chimeric nucleic acid sequence) encoding both a CAR protein that is selective for a brain cancer cell, and a drug-resistance polypeptide. In a preferred embodiment, the CAR protein is an IL13CAR and the drug resistant polypeptide is an MGMT protein which is capable of conferring TMZ-resistance to cells that express it. A chimeric nucleic acid sequence can be constructed, as described herein, to encode both an IL13CAR protein and an MGMT drug resistance protein. Provided below is a description of the domains or sequence regions of the IL13CAR protein and of the MGMT protein and non-limiting examples of each domain or region. The IL13CAR protein is a linear chimeric (fusion) protein which comprises, in an N-terminal to C-terminal direction, an IL13 ligand domain which selectively binds IL13R2α on a diseased cell such as a brain cancer cell, a transmembrane domain, and an intracellular signaling domain. In certain embodiments, the IL13CAR protein described herein may comprises a signal domain positioned N-terminal to the IL13 ligand domain and/or a hinge region positioned between the ligand domain and the transmembrane domain.

In certain embodiments, a short peptide linker comprising 1, 2, 3, 4, 5, 6, 7, 8, 9 or 10 amino acid residues is included in the IL13CAR in order to separate regions or domains of the CAR protein (e.g. the signal sequence, IL13 ligand domain, hinge region, transmembrane domain, CD28 co-stimulatory domain, CD3-zeta signaling domain, or an additional co-stimulatory domain). It is understood that the short peptide linker can be present between any two regions (domains) independent of the presence or absence of a short peptide linker between any other two regions (domains). For example, a small peptide linker can be present in the CAR wherein the linker separates the signal sequence (if present) and the IL13 ligand domain, the IL13 ligand domain and the transmembrane domain, the IL13 ligand domain and the hinge region (if present), the hinge region (if present) and transmembrane domain, the transmembrane domain and the CD28 co-signaling domain (if present), the CD28 co-signaling domain (if present) and the CD3-zeta signaling domain, the transmembrane domain and the CD3 zeta signaling domain, and/or the CD3-zeta signaling domain and the additional co-stimulatory domain (if present). The peptide linkers can be amino acids which are encoded by a nucleic acid sequence that contains a restriction endonuclease site or other feature which allows ligation of the nucleic acids encoding each of the regions or, in the case of a monocistronic construct, domains of the IL13CAR-self-cleaving peptide-MGMT chimeric protein. Each of these domains and linkers are described in greater detail below.

In one aspect, the cancer antigen-binding domain is a peptide or protein (e.g., a ligand that binds an antigen expressed on the surface of a cancer cell; a ligand that binds a receptor expressed on the surface of a cancer cell). In a preferred embodiment, the receptor is an IL132a receptor and the CAR is constructed to comprise a ligand which selectively binds the IL132a receptor. In a particular aspect, the cancer antigen-binding domain is an interleukin 13 (IL13) or a variant of IL-13 having one or more insertions, deletions, or point mutations, (e.g., E13K IL13; R109K IL13; and/or E13Y IL13). The cancer antigen-binding domain can alternatively be a variable domain of an antibody or fragment thereof that selectively binds IL13Rα2, such as a scFv fragment.

Tables 1 and 2 below provide a summary of the nucleic acids and polypeptides, respectively, described herein that can be used in the compositions, e.g., chimeric nucleic acid sequences, and methods of the invention. In one embodiment, the invention includes a chimeric nucleic acid sequence comprising any combination of nucleic acid sequences referred to in Table 1. In one embodiment, the invention includes a chimeric nucleic acid sequence encoding any combination of amino acid sequences referred to in Table 2.

TABLE 1

Sequence Identifiers for Nucleic Acid Sequences

| SEQ ID NO | Description | Nucleotide Positions Relative to SEQ ID NO: 1 |
|---|---|---|
| 1 | IL13(WT)CAR-P140K Full Length (SEQ ID NO: 1) | |
| 2 | IL13(E13Y)CAR-P140K Full Length (SEQ ID NO: 2) | |
| 3 | IL13(E13K.R109K)CAR-P140K Full Length (SEQ ID NO: 3) | |
| 7 | Restriction endonuclease site | 1-6 |
| 8 | Kozak sequence | 7-12 |
| 9 | IL13 Signal Sequence | 13-108 |
| 10 | Mature IL13 | 109-450 |
| 11 | Dipeptide linker-1 | 451-456 |
| 12 | CD8 Hinge region | 457-591 |
| 13 | Dipeptide linker-2 | 592-597 |
| 14 | CD3 zeta transmembrane domain | 598-666 |
| 15 | Dipeptide linker-3 | 667-672 |
| 16 | CD28 costimulatory domain | 673-804 |
| 17 | Dipeptide linker-4 | 805-810 |
| 18 | CD3 zeta signaling domain | 811-1140 |
| 19 | Stop codon | 1141-1143 |
| 20 | 5 amino acid linker/restriction site/ reading frame adjust | 1144-1158 |
| 21 | Self-cleaving peptide | 1159-1212 |
| 22 | P140K MGMT drug resistance polypeptide | 1213-1839 |
| 23 | Stop codon | 1840-1842 |
| 24 | Restriction endonuclease site | 1843-1846 |
| 34 | Mature IL13 with E13Y mutation | 109-450 |
| 35 | Mature IL13 with E13KR109K | 109-450 |
| 48 | MGMT drug resistance polypeptide (P140) | |

TABLE 2

Sequence Identifiers for Polypeptide Sequences

| SEQ ID NO | Description | Amino Acid Positions Relative to SEQ ID NO: 4 |
|---|---|---|
| 4 | IL13(WT)CAR-P140K Full Length (SEQ ID NO: 4) | |
| 5 | IL13(E13Y)CAR-P140K Full Length (SEQ ID NO: 5) | |
| 6 | IL13(E13K.R109K)CAR-P140K Full Length (SEQ ID NO: 6) | |
| 25 | IL13CAR-P140K - IL13 Signal Sequence | 1-32 |
| 26 | IL13CAR-P140K - wt mature IL13 Dipeptide linker-1 | 33-146 147-148 |
| 27 | IL13CAR-P140K - CD8 Hinge region Dipeptide linker-2 | 149-193 194-195 |
| 28 | IL13CAR-P140K - CD3 zeta transmembrane domain Dipeptide linker-3 | 196-218 219-220 |
| 29 | IL13CAR-P140K - CD28 costimulatory domain Dipeptide linker-4 | 221-264 265-266 |
| 30 | IL13CAR-P140K - CD3 zeta signaling domain | 267-376 |
| 31 | 5 amino acid linker/reading frame adjust/ restriction site | 377-381 |
| 32 | IL13CAR-P140K - 2A self-cleaving peptide | 382-399 |
| 33 | IL13CAR-P140K - P140K MGMT drug resistance protein | 400-606 |
| 36 | Mature IL13 with E13Y mutation | 33-146 |
| 37 | Mature IL13 with E13KR109K | 33-146 |
| 38 | G156A-MGMT | |
| 39 | MGMT-2 | |
| 40 | MGMT-3 | |
| 41 | MGMT-5 | |
| 43 | MGMT (GenBank NP_002403-(P140K)) | |
| 44 | IL13Rα2 | |

TABLE 2-continued

Sequence Identifiers for Polypeptide Sequences

| SEQ ID NO | Description | Amino Acid Positions Relative to SEQ ID NO: 4 |
|---|---|---|
| 45 | IL13(WT)CAR-P140K Full Length (SEQ ID NO: 45) | |
| 46 | IL13(E13Y)CAR-P140K Full Length (SEQ ID NO: 46) | |
| 47 | IL13(E13K.R109K)CAR-P140K Full Length (SEQ ID NO: 47) | |
| 49 | MGMT P140 | |

The Ligand

The IL13CAR ligand (alternatively, ligand domain) is a peptide, polypeptide or protein which selectively binds to an IL13 receptor, e.g., IL13Rα2, expressed by a diseased cell. The diseased cell may be a tumor cell or other cancerous or malignant cell and the protein expressed by the diseased cell is alternatively referred to herein as a cancer antigen. In some embodiments, the cancer antigen is a protein which is expressed by none or few (less than 50%, 40%, 30% 20% or 10% as determined by mRNA expression profiling) healthy tissue cells. In one embodiment, the diseased cell is a brain cancer cell such as a glioblastoma cell. In a particular aspect, the cancer antigen-binding domain is all or a biologically active portion of an antibody that binds (e.g., specifically or selectively binds) an IL-13R (e.g., IL13Rα2, e.g., GenBank Acc. No. NP_000631; SEQ ID NO:44). In other aspects, the ligand (cancer antigen-binding domain) is a scFv directed against (binds to; specifically or selectively binds to) an IL-13R (e.g., IL13Rα2).

A variety of antigens expressed by cancer (e.g., tumor) cells are known in the art. In one aspect, the cancer antigen is a brain tumor antigen e.g., that is expressed on the tumor surface. In a particular aspect, the brain tumor antigen is expressed by a high-grade malignant glioma (e.g., a glioma/malignant brain tumor antigen). Specific examples of high-grade malignant gliomas include glioblastoma multiforme (GBM), anaplastic astrocytoma and pediatric glioma. Specific examples of antigens expressed by tumor cells of high-grade gliomas include EGFRvIII, EphA2, Her-2 and IL-13R (e.g., IL13Rα2).

In one aspect, the cancer antigen targeted by the methods and compositions of the invention is an IL13 receptor α-2 (IL13Rα2), a glioblastoma multiforme (GBM)-associated protein that is overexpressed on GBM tumors but minimally, or not, expressed in normal brain tissue (Thaci et al., Neuro-Onco, 16(10):1304-1312 (2014); Sengupta et al., Biomed Res Int, 2014:952128 (2014)). In a one aspect, the IL13 CAR expresses or contains a ligand domain which is IL13 and/or an IL13 mutant such as E13K IL13 (SEQ ID NO:36) and/or R109K IL13 (SEQ ID NO:37) that binds to an IL13α2 receptor (Kong et al., Clin Cancer Res, 18(21): 5949-5960 (2012)). The IL13Rα2 protein has also been found to be upregulated breast cancers including breast cancer metastasis (Papageorgis et al., 2015, Breast Canc Res, 17:98-112) in head and neck cancers (Joshi et al., 2000, Cancer Res, 60:1168-1172; Kawakami et al, 2003, 9:6381-6388) and were also shown to promote invasion and metastasis of pancreatic, ovarian, and colorectal cancers (Fujisawa et al., 2009, Int J Cancer, 69:8678-8695; Barderas et al., 2012, Cancer Res, 72:2780-2790). Accordingly, the compositions and methods described herein are useful in a method for treating a subject diagnosed with a malignancy wherein the type of malignancy includes but is not limited to a brain, head and neck, breast, pancreatic, ovarian and colorectal cancer.

A person having ordinary skill in the art can generate ligands which specifically bind the IL13Rα2. For example, routine experimentation is done to generate antibodies which selectively bind IL13Rα2, such as though immunization of a mouse with the extracellular domain of IL13Rα2 or by phage display. The variable domain of the antibodies with desired selective binding activity can then be used to create a single chain variable domain (scFv). In one embodiment, an scFv which selectively binds IL13Rα2 with the same affinity as wildtype IL13, IL13(E13Y), IL13(R109K) or IL13(E13K.R109K) can be used as a ligand in an IL13CAR construct as disclosed herein.

In one embodiment, the IL13CAR has an IL13 ligand domain which comprises an IL13 polypeptide which is at least 90%, 95%, 96%, 97%, 98%, 99% or 99.5% identical to SEQ ID NO:26, or functional fragments thereof, wherein: a) the amino acid at position 13 of SEQ ID NO:26 is a glutamate; b) the amino acid at position 13 of SEQ ID NO:26 is a tyrosine; or c) the amino acid at position 13 of SEQ ID NO:26 is a lysine and the amino acid at position 109 of SEQ ID NO:26 is an arginine. In one embodiment, the IL13CAR IL13 ligand domain comprises SEQ ID NO:26, SEQ ID NO:36 or SEQ ID NO:37, or functional fragments thereof.

A nucleic acid according to the present disclosure encodes the IL13 polypeptide as described above. In one embodiment, the nucleic acid which encodes the IL13 polypeptide is selected from the group consisting of SEQ ID NO:10, SEQ ID NO:34 and SEQ ID NO:35.

The IL13CAR optionally further comprises a signal (leader) peptide which allows the IL13CAR protein to be processed and displayed on the host cell surface. In one embodiment, the signal peptide is the naturally occurring signal peptide for the ligand protein. For example, the ligand domain comprises the full-length IL13 protein including its signal sequence (a signal sequence comprising or consisting of the amino acid sequence of SEQ ID NO:25). In one embodiment, the signal sequence comprises a sequence which is 95%, 96%, 97%, 98%, 99% or 99.5% identical to SEQ ID NO:25. A nucleic acid according to the present disclosure encodes the signal peptide. In one embodiment, the nucleic acid which encodes the signal peptide consists of SEQ ID NO:9.

A person having ordinary skill in the art understands that a heterologous signal sequence can be used—a signal peptide from a secreted or transmembrane protein that is not IL13. Signal peptides (signal sequences) are essential parts of membrane-bound or secreted polypeptides which are needed for membrane translocation of the polypeptide and which are processed after or during membrane translocation. A signal sequence has a length of about 13 and 36 amino acids and contains at least one positive residue at the amino-terminal end. The center of the signal sequence is a strongly hydrophobic part of 10 to 15 residues and is described, for example, by Nunnari, j., et al., Curr. Opin. Cell Biol. 4 (1992) 573-580 and by Gilmore, R., et al, Ann. N.Y. Acad. Sci. 674 (1992) 27-37. Some examples of signal peptides include but are not limited to the signal peptides of VHCAMP, CD40, CD40L or TNF-R. The signal peptide is cleaved off on integration into the membrane of the target cell. It is also contemplated that a heterologous signal sequence can be used, such as that of an IgG-like protein.

Hinge Region

The IL13CAR as disclosed herein can comprise a spacer region, also referred to as a hinge region or domain, which is positioned between the IL13 ligand domain (antigen binding domain) and the transmembrane domain. The IL13CAR encompassed by the present disclosure may or may not comprise a hinge region. A hinge region of the presently described CAR is a peptide sequence which is typically flexible enough to allow the antigen binding domain to orient in different directions to facilitate antigen recognition. As will be appreciated by those of skill in the art, other appropriate spacers can be determined. For example, a short oligo- or polypeptide linker, e.g., between 2 and 10 amino acids in length, may form the linkage between the transmembrane domain and the cytoplasmic region of the CAR. Examples of a hinge region is a hinge region from an immunoglobulin (e.g., a hinge region of IgG1), include but are not limited to a hinge region from an immunoglobulin-like protein or domain, the CH2CH3 region of an immunoglobulin, and portions of CD3. In one embodiment, the hinge region comprises an Ig-like domain from the CD8 alpha chain.

In one embodiment of the IL13CAR, the hinge region comprises or consists of the amino acid sequence of SEQ ID NO:27. Alternatively, the hinge region comprises or consists of a sequence which is 95%, 96%, 97%, 98%, 99% or 99.5% identical to SEQ ID NO:27. A nucleic acid according to the present disclosure encodes the hinge region. In one embodiment, the nucleic acid which encodes the hinge region comprises SEQ ID NO:12. In one embodiment, the nucleic acid encoding the IL13CAR comprises a nucleic acid which is at least 90%, 95%, 96%, 97%, 98%, 99% or 99.5% identical to SEQ ID NO: 12.

Transmembrane Domain

As described herein, the CAR comprises one or more transmembrane domains. Typically, the transmembrane domain is a hydrophobic region (e.g., a hydrophobic alpha helix) that spans the membrane. Any of a variety of transmembrane domains can be used. Examples of suitable transmembrane domains include, but are not limited to, a CD3 (e.g., a CD3-zeta transmembrane domain) or a CD28 transmembrane domain. The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154.

In one embodiment, the transmembrane domain of the IL13CAR comprises or consists of at least a portion of the human CD3 zeta chain, for example, SEQ ID NO:28. In one embodiment, the transmembrane domain comprises or consists of a sequence which is 95%, 96%, 97%, 98%, 99% or 99.5% identical to SEQ ID NO:28. A nucleic acid according to the present disclosure encodes the transmembrane domain. In one embodiment, the nucleic acid which encodes the transmembrane domain comprises SEQ ID NO:14, or a nucleic acid which is at least 90%, 95%, 96%, 97%, 98%, 99% or 99.5% identical to SEQ ID NO: 14.

Cytoplasmic Signaling Domain(s)

As described herein, the IL13CAR has a cytoplasmic domain which transmits an activation and/or a stimulatory signal to the T cell after antigen is bound (e.g., leading to the activation, initiation, expansion, persistence and/or amplification of the T cells and the T cell response (e.g., the signal required for cytotoxicity) against tumor antigen). The cytoplasmic domain comprises one or more signaling domains (e.g., co-stimulatory domains) and/or one or more activation domains of, or associated with, a T cell receptor. Examples of suitable cytoplasmic signaling domains include but are not limited to those of CD3-ζ (CD3-zeta) which contains an immunoreceptor tyrosine-based activation motif (ITAMs), FcERIγ, CD28 (e.g., chimeric CD28), 4-IBB (CD137), DAP10, OX40 (CD134), CD4, CD27, CD244, inducible T-cell co-stimulator (ICOS), leukocyte C-terminal SRC kinase (LCK), and CD137 (e.g., Sadelain et al., *Cancer Discov*, 3(4):388-398 (2013); Lee et al., *Clin Cancer Res*, 18(10):2780-2790 (2012)). The presence of the one or more these cytoplasmic domains can initiate pathways by the association of ZAP70, TNF receptor-associated factor 1 (TRAF1), PI3K and growth factor receptor-bound protein 2 (GRB2) with elements in the cytoplasmic domain of the CARs, leading to the triggering of signaling intermediates and gene transcription.

"Co-stimulatory domain" or "co-stimulatory signaling domain" refers to the portion of the CAR comprising the intracellular domain of a co-stimulatory molecule. Co-stimulatory molecules are cell surface molecules other than antigen receptors or Fc receptors that provide a second signal required for efficient activation and function of T lymphocytes upon binding to antigen. A co-stimulatory domain undergoes a conformational change that leads to an activation signal to the cell through, for example, the CD3-zeta signaling domain. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M 1CB, HVEM, lymphotoxin beta receptor, 3/TR6, ILT3, ILT4, an agonist or antibody that binds Toll ligand receptor and a ligand that specifically binds with B7-H3. The inclusion of one or more co-stimulatory domains within the IL13CAR may enhance the efficacy and expansion of T cells expressing IL13CARs. In one embodiment, a co-stimulatory domain also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

As will be apparent to those of skill in the art, the IL13CAR can have any number of activation domains and/or stimulatory domains. Each of the signaling domains is linked via a peptide bond to form the cytoplasmic domain of the IL13CAR construct. In one aspect, the IL13CAR has an activation domain and a stimulatory domain. In another aspect, the IL13CAR has one, two three, four five, etc. activation domains and one two, three, four, five, etc. stimulatory domains.

In one embodiment, the IL13CAR of the present disclosure comprises the signaling domains of the human CD28 protein and/or of the human CD3-zeta chain. In one embodiment, IL13CAR comprises both a CD28 and a CD3-zeta chain signaling domain, wherein the CD28 co-stimulatory domain is N-terminal to the CD3-zeta signaling domain. Also contemplated is a CAR cytoplasmic domain in which the CD3-zeta domain is N-terminal to the CD28 co-stimulatory domain. As described herein, the CD28 co-stimulatory domain comprises the sequence of SEQ ID NO:29. The CD3-zeta signaling domain comprises or consists of the sequence of SEQ ID NO:30. A nucleic acid according to the present disclosure encodes the CD28 co-stimulatory domain. In one embodiment, the nucleic acid which encodes the CD28 co-stimulatory domain consists of SEQ ID NO:16. A nucleic acid according to the present disclosure encodes the CD3-zeta signaling domain. In one embodiment, the nucleic acid which encodes the CD3-zeta signaling domain consists of SEQ ID NO:18. Each of these signaling domains may contain one or more deletions, insertions, or point mutations (natural or artificial) wherein the signaling function of each domain is about the same as the signaling function of the protein that does not contain the one or more deletions, insertions, or point mutations.

In one embodiment, the cytoplasmic domain of the IL13CAR is encoded by a nucleic acid sequence comprising nucleotides 673-1140 of SEQ ID NO:1, or nucleotides 673-1143 of SEQ ID NO:1. In another embodiment, the IL13CAR comprises a cytoplasmic domain comprising amino acid residues 221-376 of SEQ ID NO:4.

FIG. 1A illustrates an embodiment of the IL13CAR construct in which the IL13 ligand is the variant containing the E13K and R109K substitutions.

Drug Resistant Polypeptide

The present disclosure is directed, at least in part, to a nucleic acid encoding both a CAR protein selective for a brain cancer cell as detailed above and a drug-resistance polypeptide, wherein expression of both the CAR and the drug resistance polypeptide is useful for treating a cancer. For example, the CAR and drug resistance polypeptide can be expressed in cells administered to a subject being treated with a chemotherapeutic agent and/or an agent that enhances cytotoxicity of a chemotherapeutic agent. Examples of chemotherapeutic agents include 1,3-bis(2-chloroethyl)-1-nitrosurea (BCNU or carmustine), fotemustine, lomustine and Temozolomide (TMZ) commonly used to treat malignant glioma (e.g., glioblastoma multiforme (GBM)). The cytotoxic action of some chemotherapeutic agents involves formation of an $O^6$-methylguanine lesion that is capable of rearranging to form a lethal intrastrand crosslink. The effectiveness of these methylating agents is limited, however, by tumor overexpression of the DNA repair protein, $O^6$-methylguanine DNA methyltransferase (MGMT), a protein which removes cytotoxic $O^6$-alkylguanine adducts from DNA of treated cells. Tumor cells expressing high levels of MGMT are therefore partially or completely resistant to killing by TMZ chemotherapy. One means to prevent the reduced efficacy of a methylating agent is to treat a subject undergoing TMZ chemotherapy with an inhibitor of MGMT, specifically $O^6$-benzylguanine. However, dosing of $O^6$-benzylguanine is limited due to its toxic effect on hematopoietic cells.

Temozolomide (TMZ) is an anti-glioma chemotherapeutic drug that has cytotoxic effects on hematopoietic cells including T cells. The standard dosage of TMZ as directed by the FDA, and hence an unavoidable step in anti-glioma treatment, kills the T cells by methylating their DNA, very much in the same fashion that TMZ destroys tumor cells (Sengupta et al., *Clin Dev Immunol*, 831090 (2012)). However, it has been shown that over-expression of wildtype MGMT or expression of one or more MGMT mutants (e.g., G156A; P140K) in a cell will confer protection to that cell against a methylating agent such as TMZ (Woolford et al., *J Gene Med*, 8(1):29-31 (2006)). Accordingly, the drug resistance polypeptide encoded by the above-described nucleic acid is MGMT or an MGMT variant which confers resistance to TMZ. These TMZ resistant variants include but are not limited to P140K-MGMT (SEQ ID NO:33), P140K-MGMT (SEQ ID NO:43), G156A-MGMT (SEQ ID NO:38), MGMT-2 (SEQ ID NO:39), MGMT-3 (SEQ ID NO:40) and MGMT-5 (SEQ ID NO:41) (Fontes et al., Mol Cancer Ther, 5(1):121-128). The indicated positions (locations) of amino acid substitutions in the MGMT variants described throughout (e.g., P140K and G156A) are amino acid positions based on the sequence of SEQ ID NO:33. The MGMT-2 variant has the substitutions: S152H, A154G, Y158H, G160S and L162V. The MGMT-3 variant has the substitutions: C150Y, A154G, Y158F, L162P and K165R. The MGMT-5 variant has the substitutions: N157T, Y158H and A170S.

Particularly preferred for the constructs disclosed and used herein is the P140K-MGMT variant. A nucleic acid according to the present disclosure encodes the MGMT variant. In one embodiment, the nucleic acid which encodes P140K-MGMT consists of SEQ ID NO:22. Also contemplated is a nucleic acid which encodes G156A-MGMT (SEQ ID NO:38), MGMT-2 (SEQ ID NO:39), MGMT-3 (SEQ ID NO:40) or MGMT-5 (SEQ ID NO:41), each of which may be present in an IL13CAR-MGMT construct. Also contemplated is an MGMT protein sequence comprising SEQ ID NO:43 (GenBank Acc. No. NP_002403 having the P140K point mutation) and any point mutations corresponding to the mutations of G156A-MGMT (SEQ ID NO:38), MGMT-2 (SEQ ID NO:39), MGMT-3 (SEQ ID NO:40) or MGMT-5 (SEQ ID NO:41).

The MGMT or variant thereof encoded by the chimeric nucleic acid sequence disclosed herein can be located downstream or upstream of the portion of the nucleic acid sequence encoding IL13CAR protein. In one embodiment, this chimeric nucleic acid sequence is monocistronic in which the construct comprises a single promoter sequence to drive transcription of a single transcript which in turn is translated into a single protein that is later cleaved. Use of this monocistronic construct requires a self-cleaving element positioned between the IL13CAR and MGMT proteins. For example, the chimeric nucleic acid sequence, when expressed in a host cell, initially gives rise to a single protein comprising, in an N-terminal to C-terminal direction, a CAR (e.g. the IL13 CAR described above), a self-cleaving peptide, and the MGMT protein or MGMT variant described herein. This protein is then cleaved to produce individual CAR and MGMT proteins. The CAR protein is processed and displayed on the cell surface while the MGMT protein can be retained within the cell nucleus. An alternative construct comprises in an N-terminal to C-terminal direction, an MGMT protein, a self-cleaving protein, and a CAR.

In one embodiment, the CAR and MGMT polypeptide portions are separated by a self-cleaving peptide. One example of a self-cleaving sequence is a 2A element which includes the 2A sequence from foot-and-mouth disease virus. In an exemplary embodiment, the self-cleaving sequence comprises or consists of the sequence of SEQ ID NO:32.

In an alternative embodiment, the nucleic acid sequence encoding both a CAR as described above and a MGMT or variant thereof as described above, is polycistronic, wherein it comprises a nucleic acid sequence encoding the CAR and a nucleic acid sequence encoding a MGMT or variant thereof, separated by a non-protein coding sequence such as an internal ribosome entry site (IRES). Examples of IRES sequences that can be used include, without limitation, the IRES elements of encephalomyelitis virus (EMCV), foot-and-mouth disease virus (FMDV), Theiler's murine encephalomyelitis virus (TMEV), human rhinovirus (HRV), coxsackievirus (CSV), poliovirus (POLIO), Hepatitis A virus (HAV), Hepatitis C virus (HCV), and Pestiviruses (e.g., hog cholera virus (HOCV) and bovine viral diarrhea virus (BVDV)) (see, e.g., Le et al., Virus Genes 12:135-147, 1996; and Le et al., Nuc. Acids Res. 25:362-369, 1997, each of which is incorporated by reference in their entirety).

An alternative embodiment of a polycistronic chimeric nucleic acid is one in which a second promoter is positioned between the nucleic acid sequence encoding the IL13CAR and the nucleic acid sequence encoding the MGMT or variant thereof. In this embodiment, a nucleic acid sequence encoding a self-cleaving peptide is not present.

It is also contemplated that the nucleic acids encoding the IL13CAR and MGMT variants are each within an individual nucleic acid vector. I.e., also contemplated is a system or kit which comprises a first vector comprising a nucleic acid encoding the IL13CAR as described herein and a second vector encoding an MGMT protein as described herein.

As will be appreciated by those of skill in the art, the nucleic acid sequences encoding at least the IL13CAR and MGMT proteins or variants thereof can further comprise additional components to facilitate and/or enhance the expression and function of the CAR and/or MGMT in a host cell. For example, the CAR can further comprise a (one or more) sequence that initiates translation (e.g., a Kozak sequence and/or a promoter sequence) as well as sequences for homologous recombination (retroviral 5'LTR; retroviral 3'LTR). A Kozak sequence may be used in the chimeric nucleic acid construct which comprises the nucleic acid sequence encoding the IL13CAR-2A-MGMT constructs as described herein.

A chimeric nucleic acid sequence for use according to the present disclosure is generated by ligating or linking together the following elements in a 5' to 3' direction: a Kozak sequence, a nucleic acid encoding a signal sequence, a nucleic acid encoding an IL13 ligand, a nucleic acid encoding a hinge region, a nucleic acid encoding a transmembrane domain, a nucleic acid encoding a CD28 costimulatory (signaling) domain, a nucleic acid encoding a CD3-zeta signaling domain, a nucleic acid encoding a self-cleaving peptide (e.g., the 2A peptide), and a nucleic acid encoding an MGMT protein, each of which was described above. The chimeric nucleic acid sequence can be generated by synthesizing a single sequence which includes and encodes the above elements. Alternatively, each of the elements above can be generated individually using methods known to the ordinarily skilled artisan. For example, each element was amplified using PCR wherein the PCR was designed to generate restriction endonuclease sites on the 5' and 3' ends of each element as needed, and the individual elements were digested with the appropriate endonucleases and ligated together to obtained the desired construct(s). As a result of this method for generating the IL13CAR-P140KMGMT constructs, short linker peptides are present between individual elements.

For example, a nucleic acid encoding 2, 3, 4, 5 or 6 amino acids can be positioned between the ligand domain and the hinge region, between the hinge region and the transmembrane domain, between the transmembrane domain and the CD28 co-stimulatory domain, between the CD28 co-stimulatory domain and the CD3-zeta signaling domain, between the CD3-zeta signaling domain and/or the self-cleaving peptide.

In an exemplary embodiment, the IL13CAR comprises a linker between the ligand and hinge domain consisting of 2 amino acids, proline-arginine. The linker between the hinge region and the transmembrane domain is glutamine-lysine. The linker between the transmembrane domain and the CD28 co-stimulatory domain is valine-threonine. The linker between the CD28 co-stimulatory domain and the CD3-zeta signaling domain is threonine-arginine. The linker between the CD3-zeta signaling domain and the 2A peptide is glutamine-proline-alanine-alanine-alanine. It is contemplated that each of the linkers described above may or may not be present in the IL13 CAR protein independent of the others.

Accordingly, preferred embodiments of the IL13CAR-P140KMGMT constructs for use in transfecting a host cell such as a T-cell and for use in inhibiting or preventing growth of a cell expressing IL13Rα2 and which is exposed to TMZ, include but are not limited to IL13(WT)CAR-P140KMGMT (nucleotide sequence of SEQ ID NO:1; amino acid sequence of SEQ ID NO:4); IL13(E13Y)CAR-P140KMGMT (nucleotide sequence of SEQ ID NO:2; amino acid sequence of SEQ ID NO:5); and IL13 (E13K.R109K)CAR-P140KMGMT (nucleotide sequence of SEQ ID NO:3; amino acid sequence of SEQ ID NO:6). FIG. 2A provides a schematic of the IL13(E13K.R109K)CAR-P140KMGMT construct. Additional embodiments of these IL13CAR-P140KMGMT constructs include but are not limited to those encoding the proteins IL13(WT)CAR-P140KMGMT (SEQ ID NO:45), IL13(E13Y)CAR-PAR140KMGMT (SEQ ID NO:46), and IL13) E13K.R109K)CAR-P140KMGMT (SEQ ID NO:47).

As will be appreciated by those of skill in the art, each of the nucleic acid sequences which encode for a signal peptide, an IL13 ligand, a hinge region, a transmembrane domain, and CD28 co-stimulatory domain, a CD3-zeta signaling domain, a self-cleaving peptide linker and an MGMT protein or variant thereof as disclosed herein can vary due to codon degeneracy without affecting the encoded protein. Moreover, the polypeptide sequences can also vary, such as through conservative amino acid substitutions, while not significantly affecting the function of the explicitly described proteins. Accordingly, also contemplated herein are variants of the each of the nucleotide sequences described herein such that the nucleic acid sequence of the present disclosure comprises sequences which are at least 75%, 80%, 82%, 85%, 90%, 92%, 94%, 95%, 96%, 97%, 98%, 99% or 99.5% identical to each of SEQ ID NOS:1-3, 7-24 and 34-35). Similarly, also contemplated and disclosed herein are polypeptides which are at least 75%, 80%, 82%, 85%, 90%, 92%, 94%, 95%, 96%, 97%, 98%, 99% or 99.5% identical to each of SEQ ID NOS:4-6, 25-33 and 36-41 and 43.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of the amino acid or nucleotide sequence aligned for comparison purposes is at least 30%, 40%, 50%, 60%, 70%, 80%, 85%, 90%, 92%, 94%, 95%, 96%, 97%, 98%, 99% or 100% of the length of the reference sequence, for example, those sequences provided in FIGS. 7A (SEQ ID NO:1), 7B (SEQ ID NO:4), 8A (SEQ ID NO:2), 8B (SEQ ID NO:5), 9A (SEQ ID NO:3) and 9B (SEQ ID NO:6). The actual comparison of the two sequences can be accomplished by well-known methods, for example, using a mathematical algorithm. A preferred, non-limiting example of such a mathematical algorithm is described in Karlin et al., Proc. Natl. Acad. Sci. USA, 90:5873-5877 (1993). Such an algorithm is incorporated into the BLASTN and BLASTX programs (version 2.2) as described in Schaffer et al., Nucleic Acids Res., 29:2994-3005 (2001). When utilizing BLAST and Gapped BLAST programs, the default parameters of the respective programs (e.g., BLASTN) can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1. In another embodiment, the percent identity between two polypeptides or two polynucleotides is determined over the full-length of the polypeptide or polynucleotide of interest.

Another preferred, non-limiting example of a mathematical algorithm utilized for the comparison of sequences is the algorithm of Myers and Miller, CABIOS (1989). Such an algorithm is incorporated into the ALIGN program (version 2.0), which is part of the GCG sequence alignment software package (Accelrys, San Diego, Calif.). When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, Comput. Appl. Biosci., 10: 3-5 (1994); and FASTA described in Pearson and Lipman, Proc. Natl. Acad. Sci USA, 85: 2444-8 (1988).

In another embodiment, the percent identity between two amino acid sequences can be accomplished using the GAP program in the GCG software package using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package, using a gap weight of 50 and a length weight of 3.

Similarity between polypeptides is typically determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247: 1306-1310 (1990).

A variant polypeptide can differ in amino acid sequence by one or more substitutions, deletions, insertions, inversions, fusions, and truncations or a combination of any of these. Further, variant polypeptides can be fully functional (e.g., ability to infect cells and produce progeny virus) or can lack function in one or more activities (e.g., ability to produce progeny virus). Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncations or a substitution, insertion, inversion, or deletion in a critical residue or critical region.

Amino acids that are essential for function can be identified by methods known in the art, such as site-directed mutagenesis or ala nine-scanning mutagenesis (Cunningham et al., Science, 244: 1081-1085 (1989)). The latter procedure introduces a single alanine mutation at each of the residues in the molecule (one mutation per molecule). The resulting mutant molecules are then tested for biological activity in vitro. Sites that are critical for polypeptide activity can also be determined by structural analysis, such as crystallization, nuclear magnetic resonance, or photoaffinity labeling (See Smith et al., J. Mol. Biol., 224: 899-904 (1992); and de Vos et al. Science, 255: 306-312 (1992)).

Further disclosed herein are compositions which comprise a substantially pure polypeptide comprising or consisting of a IL13CAR protein described herein as the sequence of amino acids 1-146 of SEQ ID NO:4, 5 or 6 and a polypeptide having preferably at least 75%, 80%, 82%, 85%, 90%, 92%, 94%, 95%, 96%, 97%, 98% or 99% sequence identity to the sequence of amino acids 1-146 of SEQ ID NO:4, 5 or 6, and a P140KMGMT variant described herein as the sequence of amino acids 400-606 of SEQ ID NO:1 and a polypeptide having preferably at least 75%, 80%, 82%, 85%, 90%, 92%, 94%, 95%, 96%, 97%, 98% or 99% sequence identity to the sequence of amino acids 400-606 of SEQ ID NO:1 as determined using the BLAST program and parameters described herein. In another embodiment, examples of polypeptides include a substantially pure polypeptide comprising or consisting of SEQ ID NOs: 4, 5 and/or 6; and a polypeptide having preferably at least 75%, 80%, 82%, 85%, 90%, 92%, 94%, 95%, 96%, 97%, 98% or 99% sequence similarity to SEQ ID NO:4, as determined using the BLAST program and parameters described herein.

In particular aspects, the disclosure is directed to an isolated polypeptide encoded by SEQ ID NO: 1 (IL13 CAR-P140KMGMT), SEQ ID NO: 2 (IL-13(E13Y) CAR-P140KMGMT), SEQ ID NO: 3 (IL-13(E13K R109K) CAR-P140KMGMT) or a combination thereof. In other aspects, the disclosure is directed to a polypeptide (an isolated polypeptide comprising an amino acid sequence of SEQ ID NO:4, SEQ ID NO:5, SEQ ID NO:6, SEQ ID NO:45, SEQ ID NO:46, SEQ ID N0:47 or a combination thereof.

A CAR polypeptide comprising a T cell receptor comprising one or more ligands (e.g., an antibody) to one or tumor antigens of a brain cancer is also contemplated. In a particular aspect, the CAR polypeptide further comprises one or more additional agents useful for treating a brain cancer. In other aspects, the invention is directed to isolated polypeptides, and fragments, derivatives, and variants thereof, as well as polypeptides encoded by nucleotide sequences described herein (e.g., other variants). As used herein, the term "polypeptide" refers to a polymer of amino acids, and not to a specific length; thus, peptides, oligopeptides, and proteins are included within the definition of a polypeptide.

The polypeptides can be synthesized using known protein synthesis methods. In one embodiment, the polypeptide is produced by recombinant DNA and recombinant protein expression and purification techniques. For example, a nucleic acid molecule encoding the polypeptide is cloned into an expression vector, the expression vector is introduced into a host cell, the polypeptide is expressed in the host cell and the desired protein is purified and formulated for packaging and administration.

As used herein, a polypeptide is said to be "isolated," "substantially pure," or "substantially pure and isolated" when it is substantially free of material, when it is isolated from recombinant or non-recombinant cells, or free of chemical precursors or other chemicals when it is chemically synthesized. In addition, a polypeptide can be joined to another polypeptide with which it is not normally associated in a cell (e.g., in a "fusion protein") and still be "isolated," "substantially pure," or "substantially pure and isolated." An isolated, substantially pure, or substantially pure and isolated polypeptide may be obtained, for example, using affinity purification techniques described herein, as well as other techniques described herein and known to those skilled in the art.

A polypeptide of the invention can be purified to homogeneity. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of material" includes preparations of the polypeptide having less than about 30% (by dry weight) other proteins (i.e., contaminating protein), less than about 20% other proteins, less than about 10% other proteins, less than about 5%, or less than about 1% other proteins.

When a polypeptide is recombinantly produced, it can also be substantially free of culture medium', i.e., culture medium represents less than about 20%, less than about 10%, or less than about 5% of the volume of the polypeptide preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide of the invention comprises an amino acid sequence encoded by a nucleic acid molecule of SEQ ID NOs: 1, 3 and/or 5 and complements and portions thereof. The polypeptides of the invention also encompasses fragments and sequence variants having substantial homology to a polypeptide encoded by a nucleic acid molecule comprising the nucleotide sequence of SEQ ID NOs: 1, 3, and/or 5 and complements and portions thereof.

Nucleic Acid Expression Constructs

Another aspect of the disclosure pertains to nucleic acid expression constructs or vectors, retroviral vectors and/or retroviral particles and their use. Recombinant DNA technology methods known to the ordinarily skilled artisan are used to design and generate the chimeric nucleic acid sequences which encode an IL13CAR, self-cleaving peptide, and an MGMT variant as described in detail herein. The chimeric nucleic acid construct is then cloned into a plasmid vector to allow, for example, sequencing to confirm the sequence of the construct. Once the desired sequence is confirmed, the chimeric nucleic acid construct is used to produce retroviral particles for transfection of a mammalian cell. Accordingly, chimeric constructs comprising nucleic acid sequences of SEQ ID NOS:1-3 and combinations of SEQ ID NOS:7-24, 34 and/or 34-35 as described herein are cloned into such plasmid vectors for later packaging into retroviral particles. In a particular aspect, the chimeric constructs and plasmid vectors comprise one or more nucleic acid sequences comprising SEQ ID NO:1, SEQ ID NO:2 and/or SEQ ID NO:3 as described above. A plasmid vector containing the IL13(WT)CAR-P140KMGMT sequence (SEQ ID NO:1), the IL13(E13Y)CAR-P140KMGMT (SEQ ID NO:2), or IL13(E13K.R109K)CAR-2A-P140KMGMT sequence (SEQ ID NO:3) was generated by cloning fragments described herein into a pUC57 vector then into a pMFG vector as described in Example 1 prior to producing retroviral particles (Example 2).

FIG. 1B illustrates a plasmid vector comprising an IL13CAR construct wherein the MGMT gene has not yet been introduced. FIG. 2B illustrates the same plasmid backbone containing an IL13CAR construct and also containing an P140KMGMT coding sequence downstream of the IL13CAR coding sequence.

In an alternative embodiment, the nucleic acid encoding an IL13CAR as described herein is cloned into a first vector and the nucleic acid encoding an MGMT protein as described herein is cloned into a second vector. Accordingly, the present disclosure also describes a first vector (plasmid, expression, viral, retroviral, lentiviral, adenoviral, etc.) comprising a nucleic acid encoding an IL13CAR as described herein and a second vector (plasmid, expression, viral, retroviral, lentiviral, adenoviral, etc.) comprising a nucleic acid encoding an MGMT protein as described herein.

Examples of suitable nucleic acid constructs include a plasmid (e.g., a circular double stranded DNA loop) and a viral vector (e.g., a retroviral vector, a lentiviral vector, an adenoviral vector). Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of nucleic acid to which they are operably linked. In general, expression constructs in recombinant DNA techniques are often in the form of plasmids. However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences).

It will be appreciated by those skilled in the art that the design of the expression vector can depend on such factors as the choice of the host cell to be transformed and the level of expression of polypeptide desired. The expression vectors of the invention can be introduced into host cells to thereby produce polypeptides, including fusion polypeptides, encoded by nucleic acid molecules as described herein.

The recombinant expression vectors of the invention can be designed for expression of a polypeptide of the invention in prokaryotic or eukaryotic cells, e.g., bacterial cells, such as E. coli, insect cells (using baculovirus expression vectors), yeast cells or mammalian cells (primate (e.g., human), murine (e.g., mouse), feline, canine, rodent, ovine, bovine cells).

Figure 3B:
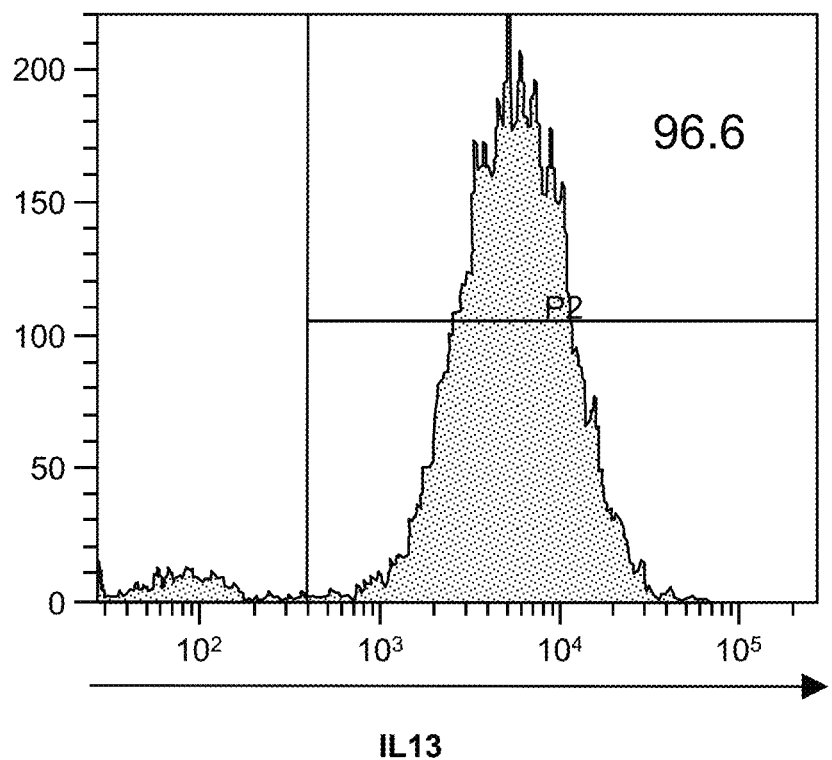
Figure 3C:
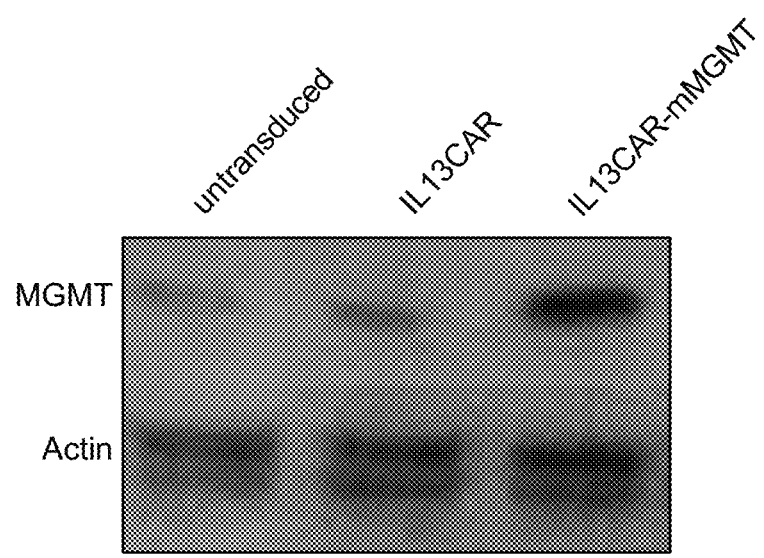

Production of retroviral particles containing the chimeric nucleic acid constructs were successfully generated to contain the chimeric nucleic acid sequence encoding IL13 (E13K.R109K)CAR-P140KMGMT as described in Examples 1 and 2. The methods described in the examples and throughout the specification and in combination with methods known to the ordinarily skilled artisan can be used to produce retroviral particles containing any of the chimeric nucleic acid constructs as described herein. Transfection efficiency through the process can be monitored by measuring cell surface expression of the IL13 ligand by flow cytometry. Cells transduced with the IL13CAR-P140KMGMT construct can be enriched, for example, using a fluorescence activated cell sorter. FIGS. 3A and 3B show enrichment of PG13 cells transfected with the IL13 (E13K.R109K)CAR-A2-P140KMGMT construct. FIG. 3A shows the relative number of cells expressing IL13 after the first transduction with the ecotropic retrovirus (e.g., 4.0%). FIG. 3B shows the relative number of cells expressing IL13 after the enrichment of cells transduced with the ecotropic retrovirus (e.g., 96.6%). Western blot analysis of cell lysates can be performed using routine methods to confirm and measure expression of the P140KMGMT protein by the host cell. As shown in FIG. 3C, enrichment of cells transduced with an IL13CAR-A2-P140KMGMT construct overexpresses the P140KMGMT protein as compared to untransduced cells or cells transduced with a construct only expressing an IL13CAR construct as depicted in FIGS. 1A-1B.

FIGS. 1A and 2A provide schematics of the IL13 (E13K.R109K)CAR-P140KMGMT cloned into a plasmid vector while FIGS. 1B and 2B show a linear depiction of the chimera flanked by the 5' LTR and 3'LTR for integration into the host cell genome.

The nucleic acid constructs described herein are introduced into host mammalian cells to impart to the cell both a tumor cell killing function and resistance to a chemotherapeutic drug which is a DNA methylating agent such as TMZ. Introduction of the nucleic acid into the mammalian host cell is accomplished, for example, using a retroviral vector, for example, as described in Example 3. Retroviral vectors for transiently or stably transducing mammalian cells are well known in the art and described below as they are used in the presently described protein expression and therapeutic systems.

Certain embodiments employ viral vectors to transduce plasma cells such as T cells with the expression systems described herein. Examples of viral vectors include, without limitation, MFG vectors, adenovirus-based vectors, adeno-associated virus (AAV)-based vectors, retroviral vectors, retroviral-adenoviral vectors, and vectors derived from herpes simplex viruses (HSVs).

Typically, a minimal retroviral vector comprises certain 5'LTR and 3'LTR sequences, one or more genes of interest (to be expressed in the target cell), one or more promoters, and a cis-acting sequence for packaging of the RNA. Other regulatory sequences can be included, as described herein and known in the art. The viral vector is typically cloned into a plasmid that may be transfected into a packaging cell line, such as a eukaryotic cell (e.g., PG13 mouse fibroblast), and also typically comprises sequences useful for replication of the plasmid in bacteria. Certain viral vectors such as retroviral vectors employ one or more heterologous promoters, enhancers, or both. Certain embodiments employ an "internal" promoter/enhancer that is located between the 5' LTR and 3' LTR sequences of the viral vector, and is operably linked to the gene of interest. A "functional relationship" and "operably linked" mean, without limitation, that the gene is in the correct location and orientation with respect to the promoter and/or enhancer, such that expression of the gene will be affected when the promoter and/or enhancer is contacted with the appropriate regulatory molecules. Any enhancer/promoter combination may be used that either regulates (e.g., increases, decreases) expression of the viral RNA genome in the packaging cell line, regulates expression of the selected gene of interest in an infected target cell, or both.

A promoter is an expression control element formed by a DNA sequence that permits binding of RNA polymerase and transcription to occur. Promoters are untranslated sequences that are located upstream (5') of the start codon of a selected gene of interest (typically within about 100 to 1000 bp) and control the transcription and translation of the coding polynucleotide sequence to which they are operably linked. Promoters may be inducible or constitutive. Inducible promoters initiate increased levels of transcription from DNA under their control in response to some change in culture conditions, such as a change in temperature.

A variety of promoters are known in the art, as are methods for operably linking the promoter to the polynucleotide coding sequence. Both native promoter sequences and many heterologous promoters may be used to direct expression of the selected gene of interest. Certain embodiments employ heterologous promoters, because they generally permit greater transcription and higher yields of the desired protein as compared to the native promoter.

Certain viral vectors contain cis-acting packaging sequences to promote incorporation of the genomic viral RNA into the viral particle. Examples include psi-sequences. Such cis-acting sequences are known in the art.

Generation of viral vectors can be accomplished using any suitable genetic engineering techniques known in the art, including, without limitation, the standard techniques of restriction endonuclease digestion, ligation, transformation, plasmid purification, PCR amplification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

Any variety of methods known in the art may be used to produce suitable retroviral particles whose genome comprises an RNA copy of the viral vector. As one method, the viral vector may be introduced into a packaging cell line that packages the viral genomic RNA based on the viral vector into viral particles with a desired target cell specificity. The packaging cell line typically provides in trans the viral proteins that are required for packaging the viral genomic RNA into viral particles and infecting the target cell, including the structural gag proteins, the enzymatic pal proteins, and the envelope glycoproteins.

In certain embodiments, the packaging cell line may stably express certain of the necessary or desired viral proteins (e.g., gag, pol) (see, e.g., U.S. Pat. No. 6,218,181). In certain embodiments, the packaging cell line may be transiently transfected with plasmids that encode certain of the necessary or desired viral proteins (e.g., gag, pol, glycoprotein), including the measles virus glycoprotein sequences described herein. In one exemplary embodiment, the packaging cell line stably expresses the gag and pol sequences, and the cell line is then transfected with a plasmid encoding the viral vector and a plasmid encoding the glycoprotein. Following introduction of the desired plasmids, viral particles are collected and processed accordingly, such as by ultracentrifugation to achieve a concentrated stock of viral particles. Exemplary packaging cell lines include PG13 (ATCC CRL-10686), 293 (ATCC CCL X), HeLa (ATCC CCL 2), D17 (ATCC CCL 183), MDCK (ATCC CCL 34), BHK (ATCC CCL-10) and Cf2Th (ATCC CRL 1430) cell lines.

Host Cells

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid molecule of the invention can be expressed in bacterial cells (e.g., *E. coli*), insect cells, yeast, or mammalian cells. In one aspect, the host cell is a mammalian cell (primate (e.g., human), murine (e.g., mouse), feline, canine, rodent, ovine, bovine cells). In a particular aspect, the mammalian cell is an immune cell. In yet another aspect, the mammalian cell is a T cell. Other suitable host cells are apparent to those skilled in the art.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), peripheral blood mononuclear cells (PBMCs), peripheral blood leukocytes (PBLs), tumor infiltrating cells, memory T cells, naive T cells, and the like. The T cell may be a CD8+ T cell or a CD4$^+$ T cell.

In one embodiment, the host cell used in the compositions and methods of the invention is an NK-92 cell (NK-92 cell line ATCC Deposit No. PTA-6672).

Nucleic acid constructs can be introduced into prokaryotic or eukaryotic cells via conventional transformation or transfection techniques. As used herein, the terms "infection", "transformation", "transduction", and "transfection" are intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells can be found in, for example, Sambrook et al., Molecular Cloning, A Laboratory Manual (2nd Ed., CSHP, New York (1989) and other laboratory manuals.

A host cell of the invention, such as a prokaryotic or eukaryotic host cell in culture, can be used to produce (express) one or more CARs of the present disclosure. Accordingly, the present disclosure further provides methods for producing a CAR using the host cells of the invention. In one embodiment, the method comprises culturing the host cell of the present disclosure (into which a recombinant expression vector encoding a polypeptide of the present disclosure has been introduced) in a suitable medium such that the one or more CARs are produced (e.g., expressed on the surface of the host cell).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene will survive, while the other cells die).

As exemplified herein, contemplated is an immune cell, such as but not limited to a T cell, that expresses a IL13CAR and which is resistant to exposure to the chemotherapeutic agent temozolomide. Specifically, shown herein is that T cells transduced with a nucleic acid sequence encoding and expressing IL13CAR (SEQ ID NO:4, SEQ ID NO:5 or SEQ ID NO:6) and the P140KMGMT mutant (SEQ ID NO:33) as detailed above have a higher survival rate compared to T cells expressing a CAR expressing only IL13 in the presence of TMZ. Thus, in a particular aspect, the invention is directed to a CAR expressing IL13 and/or a variant of IL13 (e.g., SEQ ID NO:4 (WT IL13 CAR), SEQ ID NO:5 (IL13E13YCAR) or SEQ ID NO:6 (IL13E13K.R109KCR) and/or R109K IL13CAR) and a MGMT mutant that chemoprotects a cell (e.g., a P140KMGMT mutant (SEQ ID NO:33, SEQ ID NO:38, SE ID NO:39, SEQ ID NO:40, SEQ ID NO:41). In one embodiment, the cell is transduced with an IL13CAR-A2-MGMT construct wherein the MGMT protein is not a wildtype MGMT protein (SEQ ID NO:49).

Harvesting and Transfection of Host T Cells

T cells engineered with chimeric antigen receptors (CAR) to enable highly specific tumor recognition and killing have gained considerable attention following promising clinical results (Grupp et al., 2013, N Eng J Med, 368:1509-1518; Porter et al., 2011, N Eng J Med, 365:725-733; Sadelain et al., 2009, Curr Opin Immunol, 21:215-223). Reprogramming T cells with CAR genes provides an MHC-independent mechanism for docking with and lysing tumor cells. Such modified T cells have been alternatively termed "designer T cells," "T-bodies," or "CAR-T cells" (Ma et al., 2002, Cancer Chemotherapy & Biological Response Modifiers: Elsevier Science, pp. 319-345; Park et al., 2011, Trends Biotech, 29:550-557; Ma et al., 2014, Prostate, 74:286-296).

In another aspect, the disclosure is directed to a method of producing a cell which expresses a CAR comprising a T cell receptor comprising one or more ligands (e.g., an antibody) to one or tumor antigens of a brain cancer and an MGMT protein which increases viability of a cell transduced with the nucleic acid encoding the CAR and MGMT protein and exposed to a DNA methylating agent such as TMZ. In a particular aspect, the disclosure is directed to a method of producing a cell which expresses a CAR having an amino acid sequence of SEQ ID NO: 4 (IL13 CAR-P140KMGMT), SEQ ID NO:5 (IL-13(E13Y) CAR-P140KMGMT), SEQ ID NO:6 (IL-13(E13K R109K) CAR-P140KMGMT) or a combination thereof. The method comprises introducing a nucleic acid sequence comprising SEQ ID NO:1 (IL13(WT)CAR-P140KMGMT), SEQ ID NO:2(IL-13(E13Y) CAR-P140KMGMT) or SEQ ID NO:3 (IL-13(E13K R109K) CAR-P140KMGMT) into the cell; and maintaining the cell under conditions in which the CAR is expressed by the cell, thereby producing a cell which expresses a chimeric antigen receptor having an amino acid sequence of SEQ ID NO:4 (IL13(WT)CAR-P140KMGMT), SEQ ID NO:5 (IL-13(E13Y) CAR-P140KMGMT), SEQ ID NO:6 (IL-13(E13K R109K) CAR-P140KMGMT) or a combination thereof.

In a particular aspect, the nucleic acid sequence is introduced into the cell using a viral vector (e.g., a retroviral vector, a lentiviral vector, an adenoviral vector or a combination thereof). In another aspect, the cell is a mammalian cell, such as a mammalian T cell (e.g., a human T cell or a mouse T cell). In a particular aspect, the cell is an autologous cell or a human leukocyte antigen (HLA)-matched cell. In yet another aspect, the cell is obtained from one or more individuals with brain cancer (e.g., a high-grade malignant glioma such as a glioblastoma multiforme (GBM), an anaplastic astrocytoma or a pediatric glioma).

Therefore, an additional aspect relates to a recombinant T-cell that expresses at least one CAR and drug-resistance polypeptide according to the present disclosure. A particularly preferred transformed host cell is a transgenic T-precursor cell or a stem cell that is characterized in that it comprises a nucleic acid construct according to the present disclosure. Methods for transformation or transduction of host cells and/or stem cells are well known to the person of skill, and, for example, include electroporation or microinjection. A particularly preferred transformed host cell is a patient-unique T-cell, which is after the extraction transfected with a nucleic acid construct according to this disclosure. According to the disclosure, host cells in particular can be obtained by extracting one or several cells, preferably T-cells, in particular $CD8^+$-T-cells that are subsequently transfected or transduced ex vivo with one or more nucleic acid constructs according to the present disclosure, in order to thereby obtain host cells according to the present disclosure.

Prior to expansion and genetic modification, a source of T cells is obtained from a subject. The term "subject" is intended to include living organisms in which an immune response can be elicited (e.g., mammals). Examples of subjects include humans and other primates dogs, cats, mice, rats, and transgenic rodent species. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention, any number of T cell lines available in the art, may be used. In certain aspects of the present disclosure, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge according to the manufacturer's instructions. After washing, the cells may be resuspended in a variety of biocompatible buffers or other saline solution with or without buffer. Alternatively, the undesirable components of the apheresis sample may be removed and the cells directly resuspended in culture media.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+T cells, can be further isolated by positive or negative selection techniques. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Once it is established that the transfected or transduced T cell is capable of expressing the IL13CAR as a surface membrane protein with the desired regulation and at a desired level, it can be determined whether the chimeric receptor is functional in the host cell to provide for the desired signal induction. Subsequently, the transduced T cells are reintroduced or administered to the subject to activate anti-tumor responses in the subject.

Pharmaceutical Compositions

In yet another aspect, the disclosure is directed to pharmaceutical compositions to facilitate administration of transduced T cells as described herein to a subject in need. The transduced T cells according to the disclosure can be made into a pharmaceutical composition or made implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed which does not ineffectuate the cells expressing the chimeric receptor. Thus, desirably the transduced T cells can be made into a pharmaceutical composition containing a balanced salt solution, preferably Hanks' balanced salt solution, or normal saline. For instance, the compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

Methods of introduction of these compositions include, but are not limited to, intracranial, intramedullary, intradermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other compounds.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Kits

The disclosure also provides a pharmaceutical pack or kit comprising one or more containers filled with one or more of the ingredients of the pharmaceutical compositions of the present disclosure. Optionally associated with such container(s) can be a notice in the form prescribed by a governmental agency regulating the manufacture, use or sale of pharmaceuticals or biological products, that notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the compounds can be separated, mixed together in any combination, present in a single vial or tablet. Compounds assembled in a blister pack or other dispensing means is preferred. For the purpose of this invention, unit dosage is intended to mean a dosage that is dependent on the individual pharmacodynamics of each compound and administered in FDA approved dosages in standard time courses.

Methods of Treatment

In another aspect, the disclosure is directed to a method of treating a malignancy in an individual in need thereof comprising administering one or more T cells that express an IL13CAR which comprises one or more ligands (e.g., an antibody) to the IL13Rα2 protein, and an MGMT protein. In a particular aspect, the disclosure is directed to a method of treating brain cancer in an individual in need thereof comprising administering one or more T cells that harbor and express a nucleic acid sequence encoding a protein comprising SEQ ID NO:26, SEQ ID NO:36 or SEQ ID NO:37 (ligand), SEQ ID NO:28 (TM), SEQ ID NOS:29 and 30 (CD28 and CD3-zeta signaling domains), and optionally further comprising SEQ ID NO:27 (hinge). In another embodiment the nucleic acid sequence comprises SEQ ID NO:1 (IL13 CAR-P140KMGMT), SEQ ID NO:2 (IL-13 (E13Y) CAR-P140KMGMT), SEQ ID NO:3 (IL-13(E13K R109K) CAR-P140KMGMT) or a combination thereof. In one aspect, the T cells are autologous T cells or a human leukocyte antigen (HLA)-matched cell. In another aspect, the brain cancer is a high-grade malignant glioma such as high-grade malignant glioma is a glioblastoma multiforme (GBM), an anaplastic astrocytoma or a pediatric glioma. In one embodiment, the methods disclosed herein are used to treat cancer associated with detrimental IL13Rα2 expression.

Other cancers which have been demonstrated to have cells over-expressing IL13Rα2 include but are not limited to breast, pancreatic, head and neck, ovarian and colorectal. In another embodiment, the cancer is one that has metastasized. Accordingly, also contemplated are methods for treating one or more of these cancers by administering to the subject one or more T cells transduced with one or more of the IL13CAR-MGMT constructs as described above.

Since the T cells express a CAR and expresses a mutant MGMT that confers protection against the drug resistance of MGMT overexpression or of an MGMT variant (e.g., P140K), the method of treating brain cancer can further comprise administering one or more chemotherapeutic agents to the individual (the brain cancer patient) sequentially or simultaneously. In other words, the modified T cell is administered before, during or after administration of the chemotherapeutic agent. Examples of chemotherapeutic agents include temozolomide (TMZ), 1,3-bis(2-chloroethyl)-1-nitrosurea (BCNU or carmustine), fotemustine and lomustine. In a particular aspect, the one or more T cells express a nucleic acid sequence comprising SEQ ID NO:1 (IL13 CAR-P140KMGMT), SEQ ID NO:2(IL-13(E13Y) CAR-P140KMGMT), SEQ ID NO:3 (IL-13(E13K R109K) CAR-P140KMGMT) or a combination thereof and the one or more chemotherapeutic agents are administered to the individual simultaneously. In a particular aspect, the individual is a mammal such as a human or other primate, or a rodent such as a mouse or rat.

The efficacy of T cells transduced with a construct encoding and expressing an IL13CAR-MGMT chimera is illustrated in part by Examples 4 and 5 below. Example 4 shows that isolated T cells transduced with a vector encoding the IL13CAR-2A-P140KMGMT protein have increased resistance (increased viability) when exposed to TMZ as compared to T cells transduced with a vector encoding the IL13CAR without co-expression of the P140KMGMT protein (e.g., see FIG. 5). Accordingly, envisioned is a method for increasing viability of an immune cell transduced with an IL13CAR-MGMT construct such as that described herein. In an exemplary embodiment, a T cell transduced with a retrovirus comprising the nucleic acid sequence of SEQ ID NO:1, SEQ ID NO:2 or SEQ ID NO:3 is provided as is a method for treating a subject diagnosed with a brain cancer receiving either sequentially or simultaneously, treatment with TMZ.

Additional studies show that the IL13CAR-MGMT constructs disclosed herein are also effective in modifying T cells which can be administered to a subject, and which can increase survival of the subject. As shown by Example 5 and illustrated in FIG. 6, mice injected with 0251 MG glioma cells were treated with TMZ and with T cells transduced with a construct encoding an IL13CAR (with no MGMT) or an IL13CAR-A2-P140KMGMT construct. While expression of the IL13CAR in the absence of the P140KMGMT increased survival as compared to no administration of a CAR T cell, animals which were administered TMZ with a T cell transduced with a nucleic acid sequence encoding the IL13CAR-A2-P140KMGMT chimera has the highest rate of survival (FIG. 6). Accordingly, contemplated herein is a method for treating a subject diagnosed with a brain cancer comprising administering to the subject an immune cell expressing an IL13CAR-MGMT protein as described herein.

The T cells and/or chemotherapeutic agent can be administered to the individual using any suitable route of administration. Examples of suitable routes of administration include, but are not limited to, intracranial, intramedullary, intradermal, intramuscular, intraperitoneal, intraocular, intravenous, subcutaneous, topical, oral and intranasal delivery.

In one aspect, the method further comprises obtaining one or more T cells from the individual and introducing a chimeric nucleic acid sequence of the invention, e.g., the nucleic acid sequence comprising SEQ ID NO:1 (IL13 CAR-P140KMGMT), SEQ ID NO:2 (IL-13(E13Y) CAR-P140KMGMT), SEQ ID NO:3 (IL-13(E13K R109K) CAR-P140KMGMT) or a combination thereof, into the T cells. Methods of obtaining T cells from an individual are known in the art and include, for example, plasmapheresis. In some aspects, the CAR T cells are grown (expanded) in the laboratory until they number e.g., in the billions. The expanded population of CAR T cells can then be infused into the patient. After the infusion, the T cells multiply in the patient's body and, with guidance from their engineered receptor, recognize and kill cancer cells that harbor the antigen on their surfaces.

Host cells expressing IL13CAR and mutant MGMT described herein, are administered in a therapeutically effective amount (i.e., an amount that is sufficient to treat the disease, such as by ameliorating symptoms associated with the disease, preventing or delaying the onset of the disease, and/or also lessening the severity or frequency of symptoms of the disease). The amount that will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

Desirably an effective amount or sufficient number of the isolated transfected or modified T cells is present in the composition and introduced into the subject such that longterm, specific, anti-tumor responses are established to reduce the size of a tumor or eliminate tumor growth or regrowth than would otherwise result in the absence of such treatment. Desirably, the amount of modified T cells administered to the subject causes a 10%, 20%, 30%, 40%, 50%, 60%, 70%, 80%, 90%, 95%, 98%, or 100% decrease in tumor size when compared to otherwise same conditions wherein the modified T cells are not present.

Accordingly, the amount of modified T cells administered should take into account the route of administration and should be such that a sufficient number of the transduced T cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of modified T cells desirably should be sufficient to provide in the subject being treated at least from about $1 \times 10^6$ to about $1 \times 10^9$ transduced T cells, even more desirably, from about $1 \times 10^7$ to about $5 \times 10^8$ transduced T cells, although any suitable amount can be utilized either above, e.g., greater than $5 \times 10^8$ cells, or below, e.g., less than $1 \times 10^7$ cells. The dosing schedule can be based on well-established cell-based therapies (see, e.g., Topalian and Rosenberg (1987) Acta Haematol. 78 Suppl 1:75-6; U.S. Pat. No. 4,690,915) or an alternate continuous infusion strategy can be employed.

EXAMPLES

IL13CAR-P140KMGMT for Temozolomide-Resistant Glioblastoma Immunotherapy

Example 1

Expression Plasmid Construction

A cDNA encoding an IL13(WT)CAR construct, a cDNA encoding an IL13(E13Y) CAR construct, and cDNA encoding an IL13(E13K.R109K)CAR construct was inserted into the BamHI and NotI cloning sites of the MFG retroviral vector, as illustrated in FIGS. 1A and 1B for the IL13(WT) CAR construct, to generate the host plasmids IL13(WT) CAR-pMFG, IL13(E13Y)CAR-pMFG, and IL13 (E13K.R109K)CAR-pMFG plasmids. (See Kong et al., (Clin Cancer Res, 2012, 18(21):5949-5960)). To generate a monocistronic transcript having both the IL13CAR and P140K.MGMT cDNA sequences, a 2A-P140KMGMT fragment with 5' NotI and 3' EagI ends was synthesized by Genscript USA (Piscataway, N.J.). The 2.3 Kb fragment was cloned into a pUC57 cloning vector for confirming the sequence. Once confirmed, it was transferred en bloc into the IL13CAR-pMFG retroviral vector at the 3' NotI site to generate each of the IL13(WT)CAR-2A-P140K.MGMT-pMFG, IL13(E13Y)CAR-2A-P140K.MGMT-pMFG, and IL13(E13K.R109K)CAR-2A-P140K.MGMT-pMFG plasmids. FIGS. 2A and 2B illustrate the IL13(E13K.R109K) CAR and IL13(E13K.R109K)CAR-2A-P140K.MGMT constructs and pMFG plasmid constructs.

Example 2

Production of Retroviral Particles

MFG retroviral particles containing a constructs encoding the IL13(E13K.R109K)CAR and IL13(E13K.R109K)CAR-2A-P140KMGMT constructs described in Example 1 were generated by using the "ping-pong" method. Each host plasmid from Example 1 was first transfected into phoenix-eco cells to generate the ecotropic retrovirus. The transfection efficiency was measured by flow cytometry of IL13 expression. Culture supernatant was saved and used to transduce amphotropic virus-encoding mouse fibroblast cell line PG13 (ATCC, Manassas, Va.). Transduced PG13 cells were tested for IL13, and IL13 positive cells were enriched by fluorescence activated cell sorter (FIGS. 3A-3B). Overexpression of MGMT in IL13-enriched cells was also tested by western blot analysis of cell lysates (FIG. 3C).

As shown in FIGS. 3A and 3B, transduced cells expressed IL13 and were enriched such that about 97% of the cells expressed the IL13(E13K.R109K)CAR-2A-P140KMGMT construct. FIG. 3C further shows increased expression of the P140KMGMT in cells transfected with the IL13 (E13K.R109K)CAR-2A-P140KMGMT as compared to untransfected cells or cells transfected with the IL13CAR-only construct.

Enriched cells were expanded under tissue culture conditions to harvest culture supernatant that contained high-titers of CAR-encoding amphotropic retrovirus.

Example 3

Genetic Modification of Human T Cells

The retroviral particles comprising the IL13 (E13K.R109K)CAR and IL13(E13K.R109K)CAR-2A-P140KMGMT constructs as generated according to the method of Example 2 were used to transduce human T cells. Human PBMCs were isolated from blood-filter discards (Rhode Island Blood Center, Providence, R.I.). PBMCs were cultured in the presence of OKT3 (10 μg/ml) and IL2 (3000 U/ml) for 36-48 h to enrich T cell populations. Enriched T cells were spinfected with retrovirus containing culture supernatants, in the presence of protamine and IL2, in a retronectin-coated plate for 1 h at room temperature. This step was repeated 3 times in the following 24 h. After 3 rounds of infection, the cells were allowed to grow in the retrovirus-containing medium for another 24 h, and then transferred to fresh RPMI-1640 medium containing 10% fetal bovine serum, antibiotics, and IL2 for future experiments. T cells, successfully transduced with the IL13 (E13K.R109K)CAR (without P140KMGMT) and untransduced T cells were used as control group in all experiments. Approximately, 20-25% of T cells transfected with the retroviral particles comprising the IL13(E13K.R109K) CAR-2A-P140KMGMT construct were positive for the IL13(E13K.R109K)CAR-2A-P140KMGMT as measured by flow cytometry to detect IL13 on the cell surface (data not shown). The transduction efficiency for IL13(E13K.R109K) CAR-2A-P140KMGMT was about 69.2%, where untransduced T cells were used as the control.

Example 4

Temozolomide Resistance in Transduced T Cells

Figure 4:
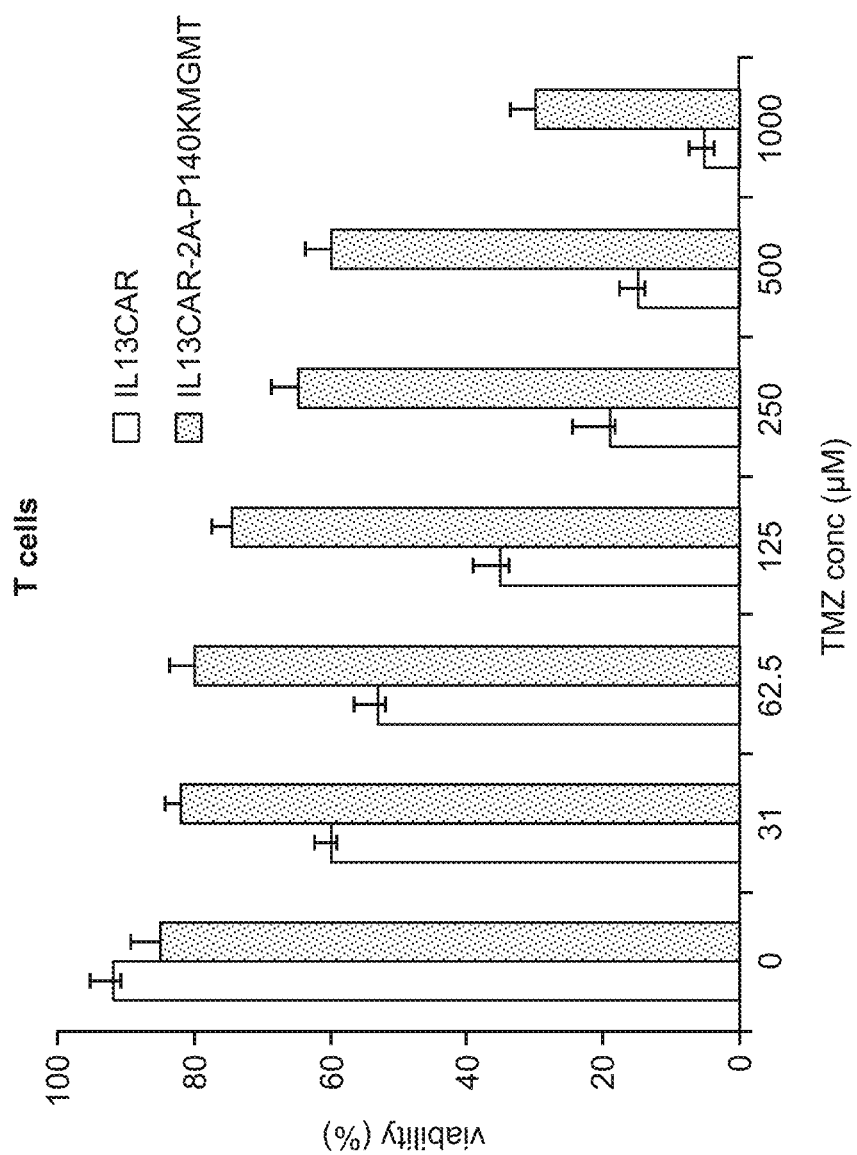
FIG. 4 provides a graph showing viability of T cells transduced with a retrovirus comprising an IL13CAR-2A-P140KMGMT construct and exposed to TMZ.

T cells transduced with IL13(E13K.R109K)CAR (FIG. 1A) or IL13(E13K.R109K)CAR-2A-P140KMGMT (FIG. 2A) as described above were incubated separately with increasing concentration of temozolomide (TMZ; 0-1000 μM) for 48 hrs. Culture media were changed every 24 h and supplemented with fresh TMZ. After treatment with TMZ, viability of the cells was analyzed by Trypan blue exclusion principle, as well as Annexin V/7AAD staining method. Frequency of Annexin V/7-AAD negative cells were measured by flow cytometry and the results represented cell viability. A survival curve was constructed to extrapolate the viability and concentration of TMZ activity. As shown in FIG. 4, T cells transduced with IL13(E13K.R109K)CAR-2A-P140KMGMT survived better as compared to IL13 (E13K.R109K)CAR-transduced T cells after exposure to TMZ. This observation indicates that genetic modification of T cells with P140KMGMT-expressing CARs rendered chemoprotection to the modified T cells.

Example 5

Functional Characterization of IL13CAR-2A-P140KMGMT

Immunoregulatory function of the transduced cells was also analyzed by measuring secretion of the cytokines IL2 and IFNγ by the transduced cells when co-cultured with glioma cells. T cells which had been transduced with IL13 (E13K.R109K)CAR-2A-P140KMGMT retrovirus were cultured with or without 200 μM of TMZ for 48-72 hrs under normal tissue culture conditions (using RPMI1640 medium with 5% serum and IL2 (3000 U/ml) and 200 μM TMZ). Next, the cells were cultured with U251MG glioma cells for 72 hrs (as described herein regarding U251MG co-culture). The culture supernatants were tested for cytokine secretion by ELISA.

Figure 5A:
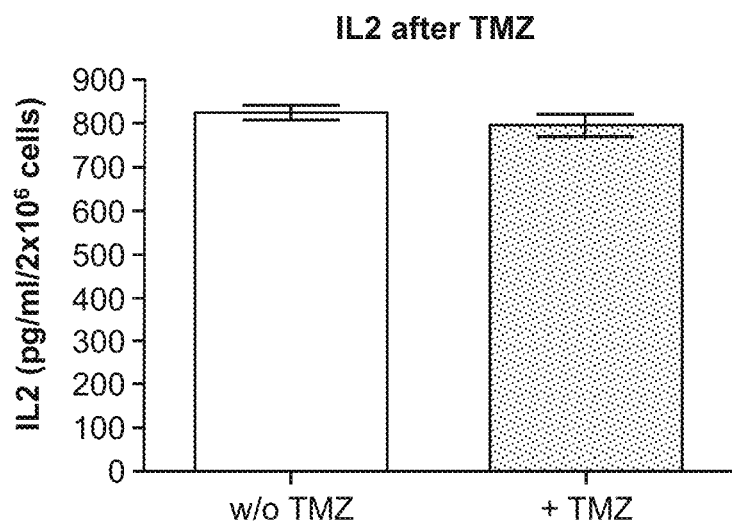
FIGS. 5A and 5B illustrate section of IL2 (FIG. 5A) and IFNγ (FIG. 5B) in cells transfected with an IL13CAR-2A-MGMT construct as described herein.
Figure 5B:
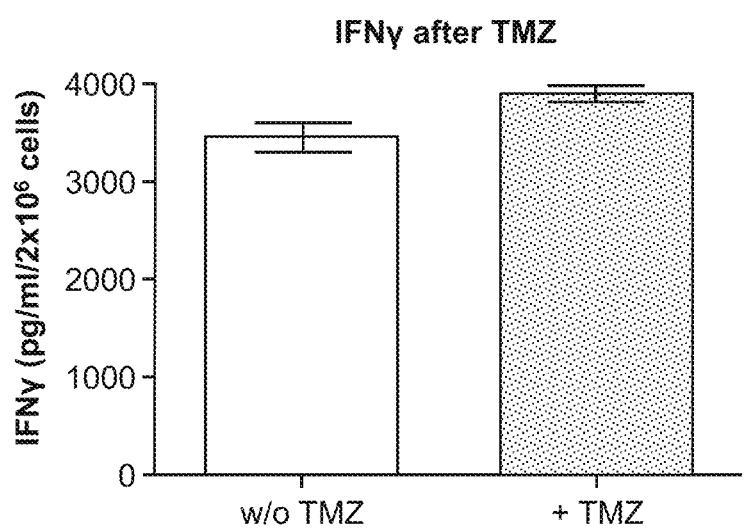

Interleukin-2 (IL2) is a marker for T cell viability and proliferation, while Interferon-gamma (IFNγ) is a marker of functionality of cytotoxic T cells. As seen in FIGS. 5A and 5B, transduced cells secreted both IL2 and IFNγ in the absence or presence of TMZ. Moreover, the presence of TMZ did not significantly decrease the secretion of either cytokine by the transduced cells. TMZ-resistant T cells were able to maintain their normal cytotoxic function after exposure to TMZ, indicating that these genetic modification indeed rendered these cells resistant to TMZ-induced leukopenic cytotoxicity.

Example 6

In Vivo Efficacy of IL13CAR-2A-MGMT

The in vivo efficacy of the IL13E13K.R109K-2A-P140KMGMT construct was tested in mice using the viral particles generated as described in Example 2. Fifty athymic nude mice were injected subcutaneously (left flank) with U251MG glioma cells (40 mice; Groups I-IV) or PBS (10 mice). Four days after glioma implantation, 3 groups of mice (Groups I, II and III, 10 mice/group) were treated orally with TMZ (64 mg/kg/day by oral gavage) for 4 days. On the 5th day after glioma implantation, the 3 groups of mice that had been treated orally with TMZ were treated as follows: Group I: an intra-tumoral injection of the IL13E13K.R109KCAR-2A-P140KMGMT construct (TMZ-resistant); Group II: the IL13 IL13E13K.R109K construct with no MGMT (TMZ sensitive); Group III: treatment with PBS only (no injection of T cells). Group IV received no T cells or TMZ treatment. The mice were monitored for visual tumor growth, behavioral changes, and morbidity until day 90 after injection of the T cells at which time the mice were sacrificed as required by IACUC restrictions.

A survival curve drawn from the results of the mouse experiment showed that tumor-bearing mice that were treated with the IL13(E13K.R109K)CAR-2A-P140KMGMT T cells and TMZ (Group I) had a median survival of 73 days and 40% of animals survived in comparison to 61 days and 14% survival in Group II animals that had been treated with TMZ-sensitive the IL13 (E13K.R109K)CAR T cells with no MGMT and TMZ. Tumor-bearing mice that received no treatment (Group IV) had a median survival of 29 days. Group III tumor-bearing animals that did not receive T cells but were orally treated with TMZ alone showed 20% survival rate but also demonstrated a lower median survival time of 36 days only, which was considered to be a background anti-tumor effect of TMZ treatment (FIGS. 9 & 10). This observation indicate that Group I animals that receive 3G TMZ-resistant CARs were most efficient in eliminating tumors by synergistic effects of CAR immunotherapy and TMZ chemotherapy.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

The invention claimed is:

1. A nucleic acid sequence encoding an IL13 chimeric antigen receptor (IL13CAR) protein, wherein the IL13CAR protein comprises amino acids 33 to 606 of SEQ ID NO:4 SEQ ID NO:5 or SEQ ID NO:6.

2. The chimeric nucleic acid sequence according to claim 1, wherein the IL13CAR protein further comprises a signal peptide.

3. The nucleic acid sequence according to claim 1, selected from the group consisting of SEQ ID NO:1 nucleotides 109 to 1839, SEQ ID NO:2 nucleotides 109 to 1839, and SEQ ID NO:3 nucleotides 109 to 1839.

4. A nucleic acid sequence comprising SEQ ID NO:1 (IL13 CAR-P140KMGMT), SEQ ID NO:2 (IL-13(E13Y) CAR-P140KMGMT), or SEQ ID NO:3 (IL-13(E13K R109K) CAR-P140KMGMT).

5. A vector comprising the chimeric nucleic acid sequence according to claim 1.

6. The vector according to claim 5, wherein the vector is a viral vector.

7. The vector according to claim 6, wherein the viral vector is a retroviral vector.

8. An isolated host cell comprising the nucleic acid sequence according to claim 1.

9. The host cell according to claim 8, wherein the cell is a mammalian cell.

10. The host cell according to claim 8, wherein the host cell is a T cell.

11. The host cell according to claim 8, wherein the cell was isolated from one or more individuals with brain cancer.

12. A pharmaceutical composition comprising the host cell according to claim 8.

13. A pharmaceutical composition comprising the nucleic acid sequence according to claim 1.

14. The chimeric nucleic acid sequence according to claim 2, wherein the signal peptide comprises the amino acid sequence of SEQ ID NO:25.

15. A nucleic acid sequence comprising nucleotides 109 to 1839 of SEQ ID NO:3.

16. The nucleic acid sequence according to claim 15, wherein the nucleic acid sequence comprises SEQ ID NO:3 (IL-13(E13K R109K) CAR-P140KMGMT).

17. A vector comprising the chimeric nucleic acid sequence according to claim 15.

18. The vector according to claim 17, wherein the vector is a viral vector.

19. The vector according to claim 18, wherein the viral vector is a retroviral vector.

20. An isolated host cell comprising the nucleic acid sequence according to claim 15.

21. The host cell according to claim 20, wherein the cell is a mammalian cell.

22. The host cell according to claim 20, wherein the host cell is a T cell.

23. The method according to claim 9, wherein the one or more immune cells is an autologous cell or a human leukocyte antigen (HLA)-matched cell.

24. A method for treating brain cancer in a subject in need thereof comprising administering to the subject one or more immune cells that express an IL13 chimeric antigen receptor protein encoded by a nucleic acid sequence selected from the SEQ ID NO:1 nucleotides 109 to 1839, SEQ ID NO:2 nucleotides 109 to 1839, and SEQ ID NO:3 nucleotides 109 to 1839.

25. A method for producing a mammalian cell which expresses an IL13CAR protein and an MGMT protein comprising:
  a) introducing into the cell the nucleic acid sequence according to claim 1; and
  b) maintaining the cell under conditions in which the IL13CAR protein and the MGMT protein are expressed by the cell.

26. The method according to claim 25, wherein the nucleic acid sequence is introduced into the cell using a viral vector.

27. The method of claim 25, wherein the viral vector is selected from the group consisting of a retroviral vector, a lentiviral vector, an adenoviral vector or an adeno-associated viral vector.

28. The method of claim 24, wherein the IL13 chimeric antigen receptor protein amino acids 33-606 of SEQ ID NO:6.

29. The method according to claim 24, wherein the brain cancer is a high-grade malignant glioma.

30. The method according to claim 24, wherein the subject is being treated with, has been treated with, or will be treated with a DNA-methylating chemotherapeutic agent.

31. The method according to claim 30, wherein the DNA-methylating chemotherapeutic agent is TMZ.

32. The method according to claim 30, wherein the DNA-methylating chemotherapeutic agent is administered before, during, or after the administering of the dose of the immune cell.

* * * * *

SEQUENCE LISTING

```
<160> NUMBER OF SEQ ID NOS: 49

<210> SEQ ID NO 1
<211> LENGTH: 1848
<212> TYPE: DNA
<213> ORGANISM: Artificial Sequence
<220> FEATURE:
<223> OTHER INFORMATION: Synthetic construct

<400> SEQUENCE: 1
ggatccgcca ccatgcatcc gctcctcaat cctctcctgt tggcactggg cctcatggcg     60
cttttgttga ccacggtcat tgctctcact tgccttggcg gctttgcctc cccaggccct    120
gtgcctccct ctacagccct cagggagctc attgaggagc tggtcaacat cacccagaac    180
cagaaggctc cgctctgcaa tggcagcatg gtatggagca tcaacctgac agctggcatg    240
tactgtgcag ccctggaatc cctgatcaac gtgtcaggct gcagtgccat cgagaagacc    300
```

| | |
|---|---|
| cagaggatgc tgagcggatt ctgcccgcac aaggtctcag ctgggcagtt ttccagcttg | 360 |
| catgtccgag acaccaaaat cgaggtggcc cagtttgtaa aggacctgct cttacattta | 420 |
| aagaaacttt ttcgcgaggg acagttcaac cctaggaagc ccaccacgac gccagcgccg | 480 |
| cgaccaccaa caccggcgcc caccatcgcg tcgcagcccc tgtccctgcg cccagaggcg | 540 |
| tgccggccag cggcgggggg cgcagtgcac acgagggggc tggacttcgc ccaattgctc | 600 |
| tgctacctgc tggatggaat cctcttcatc tatggtgtca ttctcactgc cttgttcctg | 660 |
| agagtggtta acttctgggt gaggagtaag aggagcaggc tcctgcacag tgactacatg | 720 |
| aacatgactc cccgccgccc cgggcccacc cgcaagcatt accagcccta tgccccacca | 780 |
| cgcgacttcg cagcctatcg ctccacgcgt aagttcagca ggagcgcaga cgcccccgcg | 840 |
| taccagcagg gccagaacca gctctataac gagctcaatc taggacgaag agaggagtac | 900 |
| gatgttttgg acaagagacg tggccgggac cctgagatgg ggggaaagcc gagaaggaag | 960 |
| aaccctcagg aaggcctgta caatgaactg cagaaagata gatggcggga ggcctacagt | 1020 |
| gagattggga tgaaaggcga gcgccggagg ggcaaggggc acgatggcct ttaccagggt | 1080 |
| ctcagtacag ccaccaagga cacctacgac gcccttcaca tgcaggccct gccccctcgc | 1140 |
| taacagccag cggccgcaga gggcagagga agtcttctaa catgcggtga cgtggaggag | 1200 |
| aatcccggcc ctccatggat ggacaaagat tgcgagatga agcggaccac actggactcc | 1260 |
| cccctgggca aactggagct gtctggctgt gaacaggggc tgcacgagat caaactgctg | 1320 |
| ggaaagggca ctagcgccgc tgatgctgtg aagtgccag ctccagctgc tgtgctggga | 1380 |
| ggacctgagc cactgatgca gtgcaccgcc tggctgaacg cttacttcca tcagcctgaa | 1440 |
| gccatcgagg aatttcccgt gcctgccctg caccatccag tgttccagca ggagagtttt | 1500 |
| acaaggcagg tgctgtggaa gctgctgaaa gtggtgaagt tcggggaagt gatttcctac | 1560 |
| cagcagctgg ctgctctggc tggaaaccca aaagctgctc gggccgtggg aggagctatg | 1620 |
| agaggcaatc cagtgaaaat cctgattccc tgccacaggg tggtgtgtag ctccggagct | 1680 |
| gtggggaact attctggggg actggccgtg aaagaatggc tgctggctca cgagggacat | 1740 |
| aggctgggaa agcctggcct gggagggtct agtggactgg ctggagcttg gctgaaggga | 1800 |
| gctggagcta cctcaggaag cccacctgcc ggccggaatt gacggccg | 1848 |

<210> SEQ ID NO 2
<211> LENGTH: 1848
<212> TYPE: DNA
<213> ORGANISM: Artificial Sequence
<220> FEATURE:
<223> OTHER INFORMATION: Synthetic construct

<400> SEQUENCE: 2

| | |
|---|---|
| ggatccgcca ccatgcatcc gctcctcaat cctctcctgt tggcactggg cctcatggcg | 60 |
| cttttgttga ccacggtcat tgctctcact tgccttggcg gctttgcctc cccaggccct | 120 |
| gtgcctccct ctacagccct caggtacctc attgaggagc tggtcaacat cacccagaac | 180 |
| cagaaggctc cgctctgcaa tggcagcatg gtatggagca tcaacctgac agctggcatg | 240 |
| tactgtgcag ccctggaatc cctgatcaac gtgtcaggct gcagtgccat cgagaagacc | 300 |
| cagaggatgc tgagcggatt ctgcccgcac aaggtctcag ctgggcagtt ttccagcttg | 360 |
| catgtccgag acaccaaaat cgaggtggcc cagtttgtaa aggacctgct cttacattta | 420 |
| aagaaacttt ttcgcgaggg acagttcaac cctaggaagc ccaccacgac gccagcgccg | 480 |

```
cgaccaccaa caccggcgcc caccatcgcg tcgcagcccc tgtccctgcg cccagaggcg    540
tgccggccag cggcggggggg cgcagtgcac acgaggggggc tggacttcgc ccaattgctc    600
tgctacctgc tggatggaat cctcttcatc tatggtgtca ttctcactgc cttgttcctg    660
agagtggtta acttctgggt gaggagtaag aggagcaggc cctgcacag tgactacatg     720 aacatgactc cccgccgccc cgggcccacc cgcaagcatt accagcccta tgccccacca    780
cgcgacttcg cagcctatcg ctccacgcgt aagttcagca ggagcgcaga cgccccgcg    840 taccagcagg gccagaacca gctctataac gagctcaatc taggacgaag agaggagtac    900
gatgttttgg acaagagacg tggccggac cctgagatgg ggggaaagcc gagaaggaag     960
aaccctcagg aaggcctgta caatgaactg cagaaagata agatggcgga ggcctacagt    1020
gagattggga tgaaaggcga cgccggagg ggcaaggggc acgatggcct ttaccagggt     1080
ctcagtacag ccaccaagga cacctacgac gcccttcaca tgcaggccct gccccctcgc    1140
taacagccag cggccgcaga gggcagagga agtcttctaa catgcggtga cgtggaggag    1200
aatcccggcc ctccatggat ggacaaagat tgcgagatga agcggaccac actggactcc    1260
cccctgggca aactggagct gtctggctgt gaacaggggc tgcacgagat caaactgctg    1320
ggaaagggca ctagccgccg ctgatgctgtg aagtgccag ctccagctgc tgtgctggga    1380
ggacctgagc cactgatgca gtgcaccgcc tggctgaacg cttacttcca tcagcctgaa    1440
gccatcgagg aatttcccgt gcctgccctg caccatccag tgttccagca ggagagtttt    1500
acaaggcagg tgctgtggaa gctgctgaaa gtggtgaagt tcggggaagt gatttcctac    1560
cagcagctgg ctgctctggc tggaaaccca aaagctgctc gggccgtggg aggagctatg    1620
agaggcaatc cagtgaaaat cctgattccc tgccacaggg tggtgtgtag ctccggagct    1680
gtggggaact attctggggg actggccgtg aagaatggc tgctggctca cgagggacat    1740
aggctgggaa agcctggcct gggagggtct agtggactgg ctggagcttg gctgaaggga    1800
gctggagcta cctcaggaag cccacctgcc ggccggaatt gacggccg                  1848
```

<210> SEQ ID NO 3
<211> LENGTH: 1848
<212> TYPE: DNA
<213> ORGANISM: Artificial Sequence
<220> FEATURE:
<223> OTHER INFORMATION: Synthetic construct

<400> SEQUENCE: 3

```
ggatccgcca ccatgcatcc gctcctcaat cctctcctgt tggcactggg cctcatggcg     60
cttttgttga ccacggtcat tgctctcact tgccttggcg gctttgcctc cccaggccct    120
gtgcctccct ctacagccct caggaagctc attgaggagc tggtcaacat cacccagaac    180
cagaaggctc cgctctgcaa tggcagcatg gtatggagca tcaacctgac agctggcatg    240
tactgtgcag ccctggaatc cctgatcaac gtgtcaggct gcagtgccat cgagaagacc    300
cagaggatgc tgagcggatt ctgccgcac aaggtctcag ctgggcagtt ttccagcttg    360
catgtccgag acaccaaaat cgaggtggcc cagtttgtaa aggacctgct cttacattta    420 aagaaactt ttaaggaggg acagttcaac cctaggaagc ccaccacgac gccagcgccg    480
cgaccaccaa caccggcgcc caccatcgcg tcgcagcccc tgtccctgcg cccagaggcg    540
tgccggccag cggcggggggg cgcagtgcac acgagggggc tggacttcgc ccaattgctc    600
tgctacctgc tggatggaat cctcttcatc tatggtgtca ttctcactgc cttgttcctg    660
agagtggtta acttctgggt gaggagtaag aggagcaggc cctgcacag tgactacatg     720
```

```
aacatgactc cccgccgccc cgggcccacc cgcaagcatt accagcccta tgccccacca     780
cgcgacttcg cagcctatcg ctccacgcgt aagttcagca ggagcgcaga cgcccccgcg     840
taccagcagg gccagaacca gctctataac gagctcaatc taggacgaag agaggagtac    900
gatgttttgg acaagagacg tggccgggac cctgagatgg ggggaaagcc gagaaggaag    960
aaccctcagg aaggcctgta caatgaactg cagaaagata agatggcgga ggcctacagt   1020
gagattggga tgaaaggcga cgccggagg ggcaaggggc acgatggcct ttaccagggt    1080
ctcagtacag ccaccaagga cacctacgac gcccttcaca tgcaggccct gcccccctcgc  1140
taacagccag cggccgcaga gggcagagga agtcttctaa catgcggtga cgtggaggag   1200
aatcccggcc ctccatggat ggacaaagat tgcgagatga agcggaccac actggactcc    1260
cccctgggca aactggagct gtctggctgt gaacagggc tgcacgagat caaactgctg     1320
ggaagggca ctagcgccgc tgatgctgtg aagtgccag ctccagctgc tgtgctggga      1380
ggacctgagc cactgatgca gtgcaccgcc tggctgaacg cttacttcca tcagcctgaa   1440
gccatcgagg aatttcccgt gcctgccctg caccatccag tgttccagca ggagagtttt   1500
acaaggcagg tgctgtggaa gctgctgaaa gtggtgaagt tcggggaagt gatttcctac   1560
cagcagctgg ctgctctggc tggaaaccca aaagctgctc gggccgtggg aggagctatg   1620
agaggcaatc cagtgaaaat cctgattccc tgccacaggg tggtgtgtag ctccggagct   1680
gtggggaact attctggggg actggccgtg aaagaatggc tgctggctca cgagggacat   1740
aggctgggaa agcctggcct gggagggtct agtggactgg ctggagcttg gctgaaggga  1800
gctggagcta cctcaggaag cccacctgcc ggccggaatt gacggccg                 1848
```

<210> SEQ ID NO 4
<211> LENGTH: 606
<212> TYPE: PRT
<213> ORGANISM: Artificial Sequence
<220> FEATURE:
<223> OTHER INFORMATION: Synthetic construct

<400> SEQUENCE: 4

```
Met His Pro Leu Leu Asn Pro Leu Leu Ala Leu Gly Leu Met Ala
1               5                   10                  15

Leu Leu Leu Thr Thr Val Ile Ala Leu Thr Cys Leu Gly Gly Phe Ala
                20                  25                  30

Ser Pro Gly Pro Val Pro Pro Ser Thr Ala Leu Arg Glu Leu Ile Glu
            35                  40                  45

Glu Leu Val Asn Ile Thr Gln Asn Gln Lys Ala Pro Leu Cys Asn Gly
        50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Gln
    130                 135                 140

Phe Asn Pro Arg Lys Pro Thr Thr Thr Pro Ala Pro Arg Pro Pro Thr
145                 150                 155                 160
```

```
Pro Ala Pro Thr Ile Ala Ser Gln Pro Leu Ser Leu Arg Pro Glu Ala
            165                 170                 175

Cys Arg Pro Ala Ala Gly Gly Ala Val His Thr Arg Gly Leu Asp Phe
        180                 185                 190

Ala Gln Leu Leu Cys Tyr Leu Leu Asp Gly Ile Leu Phe Ile Tyr Gly
        195                 200                 205

Val Ile Leu Thr Ala Leu Phe Leu Arg Val Val Thr Phe Trp Val Arg
        210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Thr Arg Lys Phe Ser Arg Ser Ala
            260                 265                 270

Asp Ala Pro Ala Tyr Gln Gln Gly Gln Asn Gln Leu Tyr Asn Glu Leu
        275                 280                 285

Asn Leu Gly Arg Arg Glu Glu Tyr Asp Val Leu Asp Lys Arg Arg Gly
        290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
            340                 345                 350

Leu Tyr Gln Gly Leu Ser Thr Ala Thr Lys Asp Thr Tyr Asp Ala Leu
        355                 360                 365

His Met Gln Ala Leu Pro Pro Arg Gln Pro Ala Ala Ala Glu Gly Arg
        370                 375                 380

Gly Ser Leu Leu Thr Cys Gly Asp Val Glu Glu Asn Pro Gly Pro Met
385                 390                 395                 400

Asp Lys Asp Cys Glu Met Lys Arg Thr Thr Leu Asp Ser Pro Leu Gly
                405                 410                 415

Lys Leu Glu Leu Ser Gly Cys Glu Gln Gly Leu His Glu Ile Lys Leu
            420                 425                 430

Leu Gly Lys Gly Thr Ser Ala Ala Asp Ala Val Glu Val Pro Ala Pro
        435                 440                 445

Ala Ala Val Leu Gly Gly Pro Glu Pro Leu Met Gln Cys Thr Ala Trp
        450                 455                 460

Leu Asn Ala Tyr Phe His Gln Pro Glu Ala Ile Glu Glu Phe Pro Val
465                 470                 475                 480

Pro Ala Leu His His Pro Val Phe Gln Gln Glu Ser Phe Thr Arg Gln
                485                 490                 495

Val Leu Trp Lys Leu Leu Lys Val Val Lys Phe Gly Glu Val Ile Ser
            500                 505                 510

Tyr Gln Gln Leu Ala Ala Leu Ala Gly Asn Pro Lys Ala Ala Arg Ala
        515                 520                 525

Val Gly Gly Ala Met Arg Gly Asn Pro Val Lys Ile Leu Ile Pro Cys
        530                 535                 540

His Arg Val Val Cys Ser Ser Gly Ala Val Gly Asn Tyr Ser Gly Gly
545                 550                 555                 560

Leu Ala Val Lys Glu Trp Leu Leu Ala His Glu Gly His Arg Leu Gly
                565                 570                 575

Lys Pro Gly Leu Gly Gly Ser Ser Gly Leu Ala Gly Ala Trp Leu Lys
```

```
                    580                 585                 590
Gly Ala Gly Ala Thr Ser Gly Ser Pro Pro Ala Gly Arg Asn
            595                 600                 605

<210> SEQ ID NO 5
<211> LENGTH: 606
<212> TYPE: PRT
<213> ORGANISM: Artificial Sequence
<220> FEATURE:
<223> OTHER INFORMATION: Synthetic construct

<400> SEQUENCE: 5

Met His Pro Leu Leu Asn Pro Leu Leu Ala Leu Gly Leu Met Ala
1               5                   10                  15

Leu Leu Leu Thr Thr Val Ile Ala Leu Thr Cys Leu Gly Phe Ala
                20                  25                  30

Ser Pro Gly Pro Val Pro Ser Thr Ala Leu Arg Tyr Leu Ile Glu
            35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
            115                 120                 125

Val Lys Asp Leu Leu Leu His Leu Lys Lys Leu Phe Arg Glu Gly Gln
    130                 135                 140

Phe Asn Pro Arg Lys Pro Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Gln Leu Leu Cys Tyr Leu Leu Asp Gly Ile Leu Phe Ile Tyr Gly
            195                 200                 205

Val Ile Leu Thr Ala Leu Phe Leu Arg Val Val Thr Phe Trp Val Arg
    210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Thr Arg Lys Phe Ser Arg Ser Ala
            260                 265                 270

Asp Ala Pro Ala Tyr Gln Gln Gly Gln Asn Gln Leu Tyr Asn Glu Leu
            275                 280                 285

Asn Leu Gly Arg Arg Glu Glu Tyr Asp Val Leu Asp Lys Arg Gly
    290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
```

```
              340                 345                 350
Leu Tyr Gln Gly Leu Ser Thr Ala Thr Lys Asp Thr Tyr Asp Ala Leu
            355                 360                 365
His Met Gln Ala Leu Pro Pro Arg Gln Pro Ala Ala Ala Glu Gly Arg
        370                 375                 380
Gly Ser Leu Leu Thr Cys Gly Asp Val Glu Glu Asn Pro Gly Pro Met
385                 390                 395                 400
Asp Lys Asp Cys Glu Met Lys Arg Thr Thr Leu Asp Ser Pro Leu Gly
                405                 410                 415
Lys Leu Glu Leu Ser Gly Cys Glu Gln Gly Leu His Glu Ile Lys Leu
            420                 425                 430
Leu Gly Lys Gly Thr Ser Ala Ala Asp Ala Val Glu Val Pro Ala Pro
        435                 440                 445
Ala Ala Val Leu Gly Gly Pro Glu Pro Leu Met Gln Cys Thr Ala Trp
    450                 455                 460
Leu Asn Ala Tyr Phe His Gln Pro Glu Ala Ile Glu Glu Phe Pro Val
465                 470                 475                 480
Pro Ala Leu His His Pro Val Phe Gln Gln Glu Ser Phe Thr Arg Gln
                485                 490                 495
Val Leu Trp Lys Leu Leu Lys Val Val Lys Phe Gly Glu Val Ile Ser
            500                 505                 510
Tyr Gln Gln Leu Ala Ala Leu Ala Gly Asn Pro Lys Ala Ala Arg Ala
        515                 520                 525
Val Gly Gly Ala Met Arg Gly Asn Pro Val Lys Ile Leu Ile Pro Cys
    530                 535                 540
His Arg Val Val Cys Ser Ser Gly Ala Val Gly Asn Tyr Ser Gly Gly
545                 550                 555                 560
Leu Ala Val Lys Glu Trp Leu Leu Ala His Glu Gly His Arg Leu Gly
                565                 570                 575
Lys Pro Gly Leu Gly Gly Ser Ser Gly Leu Ala Gly Ala Trp Leu Lys
            580                 585                 590
Gly Ala Gly Ala Thr Ser Gly Ser Pro Pro Ala Gly Arg Asn
        595                 600                 605

<210> SEQ ID NO 6
<211> LENGTH: 606
<212> TYPE: PRT
<213> ORGANISM: Artificial Sequence
<220> FEATURE:
<223> OTHER INFORMATION: Synthetic construct

<400> SEQUENCE: 6

Met His Pro Leu Leu Asn Pro Leu Leu Leu Ala Leu Gly Leu Met Ala
1               5                   10                  15
Leu Leu Leu Thr Thr Val Ile Ala Leu Thr Cys Leu Gly Gly Phe Ala
            20                  25                  30
Ser Pro Gly Pro Val Pro Pro Ser Thr Ala Leu Arg Lys Leu Ile Glu
        35                  40                  45
Glu Leu Val Asn Ile Thr Gln Asn Gln Lys Ala Pro Leu Cys Asn Gly
    50                  55                  60
Ser Met Val Trp Ser Ile Asn Leu Thr Ala Gly Met Tyr Cys Ala Ala
65                  70                  75                  80
Leu Glu Ser Leu Ile Asn Val Ser Gly Cys Ser Ala Ile Glu Lys Thr
                85                  90                  95
Gln Arg Met Leu Ser Gly Phe Cys Pro His Lys Val Ser Ala Gly Gln
```

-continued

```
                100                 105                 110
Phe Ser Ser Leu His Val Arg Asp Thr Lys Ile Glu Val Ala Gln Phe
            115                 120                 125
Val Lys Asp Leu Leu Leu His Leu Lys Lys Leu Phe Lys Glu Gly Gln
        130                 135                 140
Phe Asn Pro Arg Lys Pro Thr Thr Thr Pro Ala Pro Arg Pro Pro Thr
145                 150                 155                 160
Pro Ala Pro Thr Ile Ala Ser Gln Pro Leu Ser Leu Arg Pro Glu Ala
                165                 170                 175
Cys Arg Pro Ala Ala Gly Gly Ala Val His Thr Arg Gly Leu Asp Phe
            180                 185                 190
Ala Gln Leu Leu Cys Tyr Leu Leu Asp Gly Ile Leu Phe Ile Tyr Gly
        195                 200                 205
Val Ile Leu Thr Ala Leu Phe Leu Arg Val Val Thr Phe Trp Val Arg
    210                 215                 220
Ser Lys Arg Ser Arg Leu Leu His Ser Asp Tyr Met Asn Met Thr Pro
225                 230                 235                 240
Arg Arg Pro Gly Pro Thr Arg Lys His Tyr Gln Pro Tyr Ala Pro Pro
                245                 250                 255
Arg Asp Phe Ala Ala Tyr Arg Ser Thr Arg Lys Phe Ser Arg Ser Ala
            260                 265                 270
Asp Ala Pro Ala Tyr Gln Gln Gly Gln Asn Gln Leu Tyr Asn Glu Leu
        275                 280                 285
Asn Leu Gly Arg Arg Glu Glu Tyr Asp Val Leu Asp Lys Arg Gly
    290                 295                 300
Arg Asp Pro Glu Met Gly Gly Lys Pro Arg Arg Lys Asn Pro Gln Glu
305                 310                 315                 320
Gly Leu Tyr Asn Glu Leu Gln Lys Asp Lys Met Ala Glu Ala Tyr Ser
                325                 330                 335
Glu Ile Gly Met Lys Gly Glu Arg Arg Arg Gly Lys Gly His Asp Gly
            340                 345                 350
Leu Tyr Gln Gly Leu Ser Thr Ala Thr Lys Asp Thr Tyr Asp Ala Leu
        355                 360                 365
His Met Gln Ala Leu Pro Pro Arg Gln Pro Ala Ala Ala Glu Gly Arg
    370                 375                 380
Gly Ser Leu Leu Thr Cys Gly Asp Val Glu Glu Asn Pro Gly Pro Met
385                 390                 395                 400
Asp Lys Asp Cys Glu Met Lys Arg Thr Thr Leu Asp Ser Pro Leu Gly
                405                 410                 415
Lys Leu Glu Leu Ser Gly Cys Glu Gln Gly Leu His Glu Ile Lys Leu
            420                 425                 430
Leu Gly Lys Gly Thr Ser Ala Ala Asp Ala Val Glu Val Pro Ala Pro
        435                 440                 445
Ala Ala Val Leu Gly Gly Pro Glu Pro Leu Met Gln Cys Thr Ala Trp
    450                 455                 460
Leu Asn Ala Tyr Phe His Gln Pro Glu Ala Ile Glu Glu Phe Pro Val
465                 470                 475                 480
Pro Ala Leu His His Pro Val Phe Gln Gln Glu Ser Phe Thr Arg Gln
                485                 490                 495
Val Leu Trp Lys Leu Leu Lys Val Val Lys Phe Gly Glu Val Ile Ser
            500                 505                 510
Tyr Gln Gln Leu Ala Ala Leu Ala Gly Asn Pro Lys Ala Ala Arg Ala
        515                 520                 525
```

```
Val Gly Gly Ala Met Arg Gly Asn Pro Val Lys Ile Leu Ile Pro Cys
        530                 535                 540

His Arg Val Val Cys Ser Ser Gly Ala Val Gly Asn Tyr Ser Gly Gly
545                 550                 555                 560

Leu Ala Val Lys Glu Trp Leu Leu Ala His Glu Gly His Arg Leu Gly
                565                 570                 575

Lys Pro Gly Leu Gly Gly Ser Ser Gly Leu Ala Gly Ala Trp Leu Lys
            580                 585                 590

Gly Ala Gly Ala Thr Ser Gly Ser Pro Pro Ala Gly Arg Asn
            595                 600                 605

<210> SEQ ID NO 7
<211> LENGTH: 6
<212> TYPE: DNA
<213> ORGANISM: Artificial Sequence
<220> FEATURE:
<223> OTHER INFORMATION: Synthetic construct

<400> SEQUENCE: 7 ggatcc                                                                      6

<210> SEQ ID NO 8
<211> LENGTH: 6
<212> TYPE: DNA
<213> ORGANISM: Artificial Sequence
<220> FEATURE:
<223> OTHER INFORMATION: Synthetic construct

<400> SEQUENCE: 8 gccacc                                                                      6

<210> SEQ ID NO 9
<211> LENGTH: 96
<212> TYPE: DNA
<213> ORGANISM: Homo sapiens

<400> SEQUENCE: 9
atgcatccgc tcctcaatcc tctcctgttg gcactgggcc tcatggcgct tttgttgacc          60
acggtcattg ctctcacttg ccttggcggc tttgcc                                    96

<210> SEQ ID NO 10
<211> LENGTH: 342
<212> TYPE: DNA
<213> ORGANISM: Homo sapiens

<400> SEQUENCE: 10
tccccaggcc ctgtgcctcc ctctacagcc ctcagggagc tcattgagga gctggtcaac          60
atcacccaga accagaaggc tccgctctgc aatggcagca tggtatggag catcaacctg         120
acagctggca tgtactgtgc agccctggaa tccctgatca acgtgtcagg ctgcagtgcc         180
atcgagaaga cccagaggat gctgagcgga ttctgcccgc acaaggtctc agctgggcag         240
ttttccagct tgcatgtccg agacaccaaa atcgaggtgg cccagtttgt aaaggacctg         300
ctcttacatt taaagaaact ttttcgcgag ggacagttca ac                            342

<210> SEQ ID NO 11
<211> LENGTH: 6
<212> TYPE: DNA
<213> ORGANISM: Artificial Sequence
<220> FEATURE:
<223> OTHER INFORMATION: Synthetic construct
```

```
<400> SEQUENCE: 11 cctagg                                                                6

<210> SEQ ID NO 12
<211> LENGTH: 135
<212> TYPE: DNA
<213> ORGANISM: Homo sapiens

<400> SEQUENCE: 12
aagcccacca cgacgccagc gccgcgacca ccaacaccgg cgcccaccat cgcgtcgcag      60
cccctgtccc tgcgcccaga ggcgtgccgg ccagcggcgg ggggcgcagt gcacacgagg     120
gggctggact tcgcc                                                     135

<210> SEQ ID NO 13
<211> LENGTH: 6
<212> TYPE: DNA
<213> ORGANISM: Artificial Sequence
<220> FEATURE:
<223> OTHER INFORMATION: Synthetic construct

<400> SEQUENCE: 13 caattg                                                                6

<210> SEQ ID NO 14
<211> LENGTH: 69
<212> TYPE: DNA
<213> ORGANISM: Homo sapiens

<400> SEQUENCE: 14
ctctgctacc tgctggatgg aatcctcttc atctatggtg tcattctcac tgccttgttc     60
ctgagagtg                                                             69

<210> SEQ ID NO 15
<211> LENGTH: 6
<212> TYPE: DNA
<213> ORGANISM: Artificial Sequence
<220> FEATURE:
<223> OTHER INFORMATION: Synthetic construct

<400> SEQUENCE: 15 gttaac                                                                6

<210> SEQ ID NO 16
<211> LENGTH: 132
<212> TYPE: DNA
<213> ORGANISM: Homo sapiens

<400> SEQUENCE: 16
ttctgggtga ggagtaagag gagcaggctc ctgcacagtg actacatgaa catgactccc     60
cgccgccccg ggcccacccg caagcattac cagccctatg ccccaccacg cgacttcgca    120
gcctatcgct cc                                                        132

<210> SEQ ID NO 17
<211> LENGTH: 6
<212> TYPE: DNA
<213> ORGANISM: Artificial Sequence
<220> FEATURE:
<223> OTHER INFORMATION: Synthetic construct

<400> SEQUENCE: 17
```

```
                                            acgcgt                                                     6

<210> SEQ ID NO 18
<211> LENGTH: 330
<212> TYPE: DNA
<213> ORGANISM: Homo sapiens

<400> SEQUENCE: 18
aagttcagca ggagcgcaga cgcccccgcg taccagcagg gccagaacca gctctataac      60
gagctcaatc taggacgaag agaggagtac gatgttttgg acaagagacg tggccgggac     120
cctgagatgg ggggaaagcc gagaaggaag aaccctcagg aaggcctgta caatgaactg     180
cagaaagata agatggcgga ggcctacagt gagattggga tgaaaggcga gcgccggagg     240
ggcaaggggc acgatggcct ttaccagggt ctcagtacag ccaccaagga cacctacgac     300
gcccttcaca tgcaggccct gccccctcgc                                      330

<210> SEQ ID NO 19
<211> LENGTH: 3
<212> TYPE: DNA
<213> ORGANISM: Homo sapiens

<400> SEQUENCE: 19 taa                                                                     3

<210> SEQ ID NO 20
<211> LENGTH: 15
<212> TYPE: DNA
<213> ORGANISM: Artificial Sequence
<220> FEATURE:
<223> OTHER INFORMATION: Synthetic construct

<400> SEQUENCE: 20
cagccagcgg ccgca                                                       15

<210> SEQ ID NO 21
<211> LENGTH: 54
<212> TYPE: DNA
<213> ORGANISM: Artificial Sequence
<220> FEATURE:
<223> OTHER INFORMATION: Synthetic construct

<400> SEQUENCE: 21
gagggcagag gaagtcttct aacatgcggt gacgtggagg agaatcccgg ccct            54

<210> SEQ ID NO 22
<211> LENGTH: 621
<212> TYPE: DNA
<213> ORGANISM: Artificial Sequence
<220> FEATURE:
<223> OTHER INFORMATION: Synthetic construct

<400> SEQUENCE: 22
atggacaaag attgcgagat gaagcggacc acactggact cccccctggg caaactggag      60
ctgtctggct gtgaacaggg gctgcacgag atcaaactgc tgggaaaggg cactagcgcc     120
gctgatgctg tggaagtgcc agctccagct gctgtgctgg gaggacctga gccactgatg     180
cagtgcaccg cctggctgaa cgcttacttc catcagcctg aagccatcga ggaatttccc     240
gtgcctgccc tgcaccatcc agtgttccag caggagagtt ttacaaggca ggtgctgtgg     300
aagctgctga aagtggtgaa gttcggggaa gtgatttcct accagcagct ggctgctctg     360
gctggaaacc caaaagctgc tcgggccgtg ggaggagcta tgagaggcaa tccagtgaaa     420
```

```
atcctgattc cctgccacag ggtggtgtgt agctccggag ctgtggggaa ctattctggg      480
ggactggccg tgaaagaatg gctgctggct cacgagggac ataggctggg aaagcctggc      540
ctgggagggt ctagtggact ggctggagct tggctgaagg gagctggagc tacctcagga      600
agcccacctg ccggccggaa t                                                621
```

<210> SEQ ID NO 23
<211> LENGTH: 3
<212> TYPE: DNA
<213> ORGANISM: Artificial Sequence
<220> FEATURE:
<223> OTHER INFORMATION: Synthetic construct

<400> SEQUENCE: 23

```
tga                                                                    3
```

<210> SEQ ID NO 24
<211> LENGTH: 6
<212> TYPE: DNA
<213> ORGANISM: Artificial Sequence
<220> FEATURE:
<223> OTHER INFORMATION: Synthetic construct

<400> SEQUENCE: 24

```
cggccg                                                                 6
```

<210> SEQ ID NO 25
<211> LENGTH: 32
<212> TYPE: PRT
<213> ORGANISM: Homo sapiens

<400> SEQUENCE: 25

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

<210> SEQ ID NO 26
<211> LENGTH: 114
<212> TYPE: PRT
<213> ORGANISM: Homo sapiens

<400> SEQUENCE: 26

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Gln
            100                 105                 110

Phe Asn

```
<210> SEQ ID NO 27
<211> LENGTH: 45
<212> TYPE: PRT
<213> ORGANISM: Homo sapiens

<400> SEQUENCE: 27

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala
            35                  40                  45

<210> SEQ ID NO 28
<211> LENGTH: 23
<212> TYPE: PRT
<213> ORGANISM: Homo sapiens

<400> SEQUENCE: 28

Leu Cys Tyr Leu Leu Asp Gly Ile Leu Phe Ile Tyr Gly Val Ile Leu
1               5                   10                  15

Thr Ala Leu Phe Leu Arg Val
            20

<210> SEQ ID NO 29
<211> LENGTH: 44
<212> TYPE: PRT
<213> ORGANISM: Homo sapiens

<400> SEQUENCE: 29

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Pro
                20                  25                  30

Tyr Ala Pro Pro Arg Asp Phe Ala Ala Tyr Arg Ser
            35                  40

<210> SEQ ID NO 30
<211> LENGTH: 110
<212> TYPE: PRT
<213> ORGANISM: Homo sapiens

<400> SEQUENCE: 30

Lys Phe Ser Arg Ser Ala Asp Ala Pro Ala Tyr Gln Gln Gly Gln Asn
1               5                   10                  15

Gln Leu Tyr Asn Glu Leu Asn Leu Gly Arg Arg Glu Glu Tyr Asp Val
                20                  25                  30

Leu Asp Lys Arg Arg Gly Arg Asp Pro Glu Met Gly Gly Lys Pro Arg
            35                  40                  45

Arg Lys Asn Pro Gln Glu Gly Leu Tyr Asn Glu Leu Gln Lys Asp Lys
        50                  55                  60

Met Ala Glu Ala Tyr Ser Glu Ile Gly Met Lys Gly Glu Arg Arg Arg
65                  70                  75                  80

Gly Lys Gly His Asp Gly Leu Tyr Gln Gly Leu Ser Thr Ala Thr Lys
                85                  90                  95

Asp Thr Tyr Asp Ala Leu His Met Gln Ala Leu Pro Pro Arg
            100                 105                 110

<210> SEQ ID NO 31
<211> LENGTH: 5
```

```
<212> TYPE: PRT
<213> ORGANISM: Artificial Sequence
<220> FEATURE:
<223> OTHER INFORMATION: Synthetic construct

<400> SEQUENCE: 31

Gln Pro Ala Ala Ala
1               5

<210> SEQ ID NO 32
<211> LENGTH: 18
<212> TYPE: PRT
<213> ORGANISM: Artificial Sequence
<220> FEATURE:
<223> OTHER INFORMATION: Synthetic construct

<400> SEQUENCE: 32

Glu Gly Arg Gly Ser Leu Leu Thr Cys Gly Asp Val Glu Glu Asn Pro
1               5                   10                  15

Gly Pro

<210> SEQ ID NO 33
<211> LENGTH: 207
<212> TYPE: PRT
<213> ORGANISM: Artificial Sequence
<220> FEATURE:
<223> OTHER INFORMATION: Synthetic construct

<400> SEQUENCE: 33

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Cys Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Lys Ala Ala Arg
        115                 120                 125

Ala Val Gly Gly Ala Met Arg Gly Asn Pro Val Lys Ile Leu Ile Pro
    130                 135                 140

Cys His Arg Val Val Cys Ser Ser Gly Ala Val Gly Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Gly Leu Ala Gly Ala Trp Leu
            180                 185                 190

Lys Gly Ala Gly Ala Thr Ser Gly Ser Pro Pro Ala Gly Arg Asn
        195                 200                 205

<210> SEQ ID NO 34
<211> LENGTH: 342
<212> TYPE: DNA
<213> ORGANISM: Artificial Sequence
```

<220> FEATURE:
<223> OTHER INFORMATION: Synthetic construct

<400> SEQUENCE: 34

```
tccccaggcc ctgtgcctcc ctctacagcc ctcaggtacc tcattgagga gctggtcaac    60
atcacccaga accagaaggc tccgctctgc aatggcagca tggtatggag catcaacctg   120
acagctggca tgtactgtgc agccctggaa tccctgatca acgtgtcagg ctgcagtgcc   180
atcgagaaga cccagaggat gctgagcgga ttctgcccgc acaaggtctc agctgggcag   240
ttttccagct tgcatgtccg agacaccaaa atcgaggtgg cccagtttgt aaaggacctg   300
ctcttacatt taaagaaact ttttcgcgag ggacagttca ac                      342
```

<210> SEQ ID NO 35
<211> LENGTH: 342
<212> TYPE: DNA
<213> ORGANISM: Artificial Sequence
<220> FEATURE:
<223> OTHER INFORMATION: Synthetic construct

<400> SEQUENCE: 35

```
tccccaggcc ctgtgcctcc ctctacagcc ctcaggaagc tcattgagga gctggtcaac    60
atcacccaga accagaaggc tccgctctgc aatggcagca tggtatggag catcaacctg   120
acagctggca tgtactgtgc agccctggaa tccctgatca acgtgtcagg ctgcagtgcc   180
atcgagaaga cccagaggat gctgagcgga ttctgcccgc acaaggtctc agctgggcag   240
ttttccagct tgcatgtccg agacaccaaa atcgaggtgg cccagtttgt aaaggacctg   300
ctcttacatt taaagaaact ttttaaggag ggacagttca ac                      342
```

<210> SEQ ID NO 36
<211> LENGTH: 114
<212> TYPE: PRT
<213> ORGANISM: Artificial Sequence
<220> FEATURE:
<223> OTHER INFORMATION: Synthetic construct

<400> SEQUENCE: 36

```
Ser Pro Gly Pro Val Pro Ser Thr Ala Leu Arg Tyr Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Gln
            100                 105                 110

Phe Asn
```

<210> SEQ ID NO 37
<211> LENGTH: 114
<212> TYPE: PRT
<213> ORGANISM: Artificial Sequence
<220> FEATURE:
<223> OTHER INFORMATION: Synthetic construct

<400> SEQUENCE: 37

```
Ser Pro Gly Pro Val Pro Ser Thr Ala Leu Arg Lys Leu Ile Glu
1               5                   10                  15

Glu Leu Val Asn Ile Thr Gln Asn Gln Lys Ala Pro Leu Cys Asn Gly
                20                  25                  30

Ser Met Val Trp Ser Ile Asn Leu Thr Ala Gly Met Tyr Cys Ala Ala
            35                  40                  45

Leu Glu Ser Leu Ile Asn Val Ser Gly Cys Ser Ala Ile Glu Lys Thr
        50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Lys Glu Gly Gln
                100                 105                 110

Phe Asn
```

<210> SEQ ID NO 38
<211> LENGTH: 207
<212> TYPE: PRT
<213> ORGANISM: Artificial Sequence
<220> FEATURE:
<223> OTHER INFORMATION: Synthetic construct

<400> SEQUENCE: 38

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
                20                  25                  30

Leu Leu Gly Lys Gly Thr Ser Ala Ala Asp Ala Val Glu Val Pro Ala
            35                  40                  45

Pro Ala Ala Val Leu Gly Gly Pro Glu Pro Leu Met Gln Cys Thr Ala
        50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
                100                 105                 110

Ser Tyr Gln Gln Leu Ala Ala Leu Ala Gly Asn Pro Lys Ala Ala Arg
            115                 120                 125

Ala Val Gly Gly Ala Met Arg Gly Asn Pro Val Pro Ile Leu Ile Pro
        130                 135                 140

Cys His Arg Val Val Cys Ser Ser Gly Ala Val Ala Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
                180                 185                 190

Lys Gly Ala Gly Ala Thr Ser Gly Ser Pro Pro Ala Gly Arg Asn
            195                 200                 205
```

<210> SEQ ID NO 39
<211> LENGTH: 207
<212> TYPE: PRT

<213> ORGANISM: Artificial Sequence
<220> FEATURE:
<223> OTHER INFORMATION: Synthetic construct

<400> SEQUENCE: 39

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Cys Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Lys Ala Ala Arg
        115                 120                 125

Ala Val Gly Gly Ala Met Arg Gly Asn Pro Val Pro Ile Leu Ile Pro
    130                 135                 140

Cys His Arg Val Val Cys Ser His Gly Gly Val Gly Asn His Ser Ser
145                 150                 155                 160

Gly Val Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
            180                 185                 190

Lys Gly Ala Gly Ala Thr Ser Gly Ser Pro Pro Ala Gly Arg Asn
        195                 200                 205
```

<210> SEQ ID NO 40
<211> LENGTH: 207
<212> TYPE: PRT
<213> ORGANISM: Artificial Sequence
<220> FEATURE:
<223> OTHER INFORMATION: Synthetic construct

<400> SEQUENCE: 40

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Cys Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Lys Ala Ala Arg
        115                 120                 125
```

```
Ala Val Gly Gly Ala Met Arg Gly Asn Pro Val Pro Ile Leu Ile Pro
    130                 135                 140

Cys His Arg Val Val Tyr Ser Ser Gly Val Gly Asn Phe Ser Gly
145                 150                 155                 160

Gly Pro Ala Val Arg Glu Trp Leu Leu Ala His Glu Gly His Arg Leu
                165                 170                 175

Gly Lys Pro Gly Leu Gly Gly Ser Ser Gly Leu Ala Gly Ala Trp Leu
            180                 185                 190

Lys Gly Ala Gly Ala Thr Ser Gly Ser Pro Pro Ala Gly Arg Asn
        195                 200                 205

<210> SEQ ID NO 41
<211> LENGTH: 207
<212> TYPE: PRT
<213> ORGANISM: Artificial Sequence
<220> FEATURE:
<223> OTHER INFORMATION: Synthetic construct

<400> SEQUENCE: 41

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Val Leu Gly Gly Pro Glu Pro Leu Met Gln Cys Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Lys Ala Ala Arg
        115                 120                 125

Ala Val Gly Gly Ala Met Arg Gly Asn Pro Val Pro Ile Leu Ile Pro
    130                 135                 140

Cys His Arg Val Val Cys Ser Ser Gly Ala Val Gly Thr His Ser Gly
145                 150                 155                 160

Gly Leu Ala Val Lys Glu Trp Leu Leu Ser His Glu Gly His Arg Leu
                165                 170                 175

Gly Lys Pro Gly Leu Gly Gly Ser Ser Gly Leu Ala Gly Ala Trp Leu
            180                 185                 190

Lys Gly Ala Gly Ala Thr Ser Gly Ser Pro Pro Ala Gly Arg Asn
        195                 200                 205

<210> SEQ ID NO 42
<211> LENGTH: 6
<212> TYPE: DNA
<213> ORGANISM: Artificial Sequence
<220> FEATURE:
<223> OTHER INFORMATION: Synthetic construct

<400> SEQUENCE: 42 ccatgg                                                          6

<210> SEQ ID NO 43
<211> LENGTH: 238
```

<212> TYPE: PRT
<213> ORGANISM: Homo sapiens

<400> SEQUENCE: 43

```
Met Leu Gly Gln Pro Ala Pro Leu Glu Arg Phe Ala Ser Arg Arg Pro
1               5                   10                  15

Gln Val Leu Ala Val Arg Thr Val Cys Asp Leu Val Leu Gly Lys Met
            20                  25                  30

Asp Lys Asp Cys Glu Met Lys Arg Thr Thr Leu Asp Ser Pro Leu Gly
        35                  40                  45

Lys Leu Glu Leu Ser Gly Cys Glu Gln Gly Leu His Glu Ile Lys Leu
    50                  55                  60

Leu Gly Lys Gly Thr Ser Ala Ala Asp Ala Val Glu Val Pro Ala Pro
65                  70                  75                  80

Ala Ala Val Leu Gly Gly Pro Glu Pro Leu Met Gln Cys Thr Ala Trp
                85                  90                  95

Leu Asn Ala Tyr Phe His Gln Pro Glu Ala Ile Glu Glu Phe Pro Val
            100                 105                 110

Pro Ala Leu His His Pro Val Phe Gln Gln Glu Ser Phe Thr Arg Gln
        115                 120                 125

Val Leu Trp Lys Leu Leu Lys Val Leu Lys Phe Gly Glu Val Ile Ser
    130                 135                 140

Tyr Gln Gln Leu Ala Ala Leu Ala Gly Asn Pro Lys Ala Ala Arg Ala
145                 150                 155                 160

Val Gly Gly Ala Met Arg Gly Asn Pro Val Lys Ile Leu Ile Pro Cys
                165                 170                 175

His Arg Val Val Cys Ser Ser Gly Ala Val Gly Asn Tyr Ser Gly Gly
            180                 185                 190

Leu Ala Val Lys Glu Trp Leu Leu Ala His Gly His Arg Leu Gly
        195                 200                 205

Lys Pro Gly Leu Gly Ser Ser Gly Leu Ala Gly Ala Trp Leu Lys
    210                 215                 220

Gly Ala Gly Ala Thr Ser Gly Ser Pro Pro Ala Gly Arg Asn
225                 230                 235
```

<210> SEQ ID NO 44
<211> LENGTH: 380
<212> TYPE: PRT
<213> ORGANISM: Homo sapiens

<400> SEQUENCE: 44

```
Met Ala Phe Val Cys Leu Ala Ile Gly Cys Leu Tyr Thr Phe Leu Ile
1               5                   10                  15

Ser Thr Thr Phe Gly Cys Thr Ser Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110
```

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
    275                 280                 285

Glu Asn Glu Thr Tyr Thr Leu Lys Thr Thr Asn Glu Thr Arg Gln Leu
290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
        355                 360                 365

Tyr Pro Lys Met Ile Pro Glu Phe Phe Cys Asp Thr
    370                 375                 380

<210> SEQ ID NO 45
<211> LENGTH: 608
<212> TYPE: PRT
<213> ORGANISM: Artificial Sequence
<220> FEATURE:
<223> OTHER INFORMATION: Synthetic construct

<400> SEQUENCE: 45

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

```
Gln Arg Met Leu Ser Gly Phe Cys Pro His Lys Val Ser Ala Gly Gln
            100                 105                 110
Phe Ser Ser Leu His Val Arg Asp Thr Lys Ile Glu Val Ala Gln Phe
        115                 120                 125
Val Lys Asp Leu Leu Leu His Leu Lys Lys Leu Phe Arg Glu Gly Gln
    130                 135                 140
Phe Asn Pro Arg Lys Pro Thr Thr Thr Pro Ala Pro Arg Pro Pro Thr
145                 150                 155                 160
Pro Ala Pro Thr Ile Ala Ser Gln Pro Leu Ser Leu Arg Pro Glu Ala
                165                 170                 175
Cys Arg Pro Ala Ala Gly Gly Ala Val His Thr Arg Gly Leu Asp Phe
            180                 185                 190
Ala Gln Leu Leu Cys Tyr Leu Leu Asp Gly Ile Leu Phe Ile Tyr Gly
        195                 200                 205
Val Ile Leu Thr Ala Leu Phe Leu Arg Val Val Thr Phe Trp Val Arg
    210                 215                 220
Ser Lys Arg Ser Arg Leu Leu His Ser Asp Tyr Met Asn Met Thr Pro
225                 230                 235                 240
Arg Arg Pro Gly Pro Thr Arg Lys His Tyr Gln Pro Tyr Ala Pro Pro
                245                 250                 255
Arg Asp Phe Ala Ala Tyr Arg Ser Thr Arg Lys Phe Ser Arg Ser Ala
            260                 265                 270
Asp Ala Pro Ala Tyr Gln Gln Gly Gln Asn Gln Leu Tyr Asn Glu Leu
        275                 280                 285
Asn Leu Gly Arg Arg Glu Glu Tyr Asp Val Leu Asp Lys Arg Arg Gly
    290                 295                 300
Arg Asp Pro Glu Met Gly Gly Lys Pro Arg Arg Lys Asn Pro Gln Glu
305                 310                 315                 320
Gly Leu Tyr Asn Glu Leu Gln Lys Asp Lys Met Ala Glu Ala Tyr Ser
                325                 330                 335
Glu Ile Gly Met Lys Gly Glu Arg Arg Arg Gly Lys Gly His Asp Gly
            340                 345                 350
Leu Tyr Gln Gly Leu Ser Thr Ala Thr Lys Asp Thr Tyr Asp Ala Leu
        355                 360                 365
His Met Gln Ala Leu Pro Pro Arg Gln Pro Ala Ala Ala Glu Gly Arg
    370                 375                 380
Gly Ser Leu Leu Thr Cys Gly Asp Val Glu Glu Asn Pro Gly Pro Pro
385                 390                 395                 400
Trp Met Asp Lys Asp Cys Glu Met Lys Arg Thr Thr Leu Asp Ser Pro
                405                 410                 415
Leu Gly Lys Leu Glu Leu Ser Gly Cys Glu Gln Gly Leu His Glu Ile
            420                 425                 430
Lys Leu Leu Gly Lys Gly Thr Ser Ala Ala Asp Ala Val Glu Val Pro
        435                 440                 445
Ala Pro Ala Ala Val Leu Gly Gly Pro Glu Pro Leu Met Gln Cys Thr
    450                 455                 460
Ala Trp Leu Asn Ala Tyr Phe His Gln Pro Glu Ala Ile Glu Glu Phe
465                 470                 475                 480
Pro Val Pro Ala Leu His His Pro Val Phe Gln Glu Ser Phe Thr
                485                 490                 495
Arg Gln Val Leu Trp Lys Leu Leu Lys Val Val Lys Phe Gly Glu Val
            500                 505                 510
Ile Ser Tyr Gln Gln Leu Ala Ala Leu Ala Gly Asn Pro Lys Ala Ala
```

```
                515                 520                 525
Arg Ala Val Gly Gly Ala Met Arg Gly Asn Pro Val Lys Ile Leu Ile
    530                 535                 540

Pro Cys His Arg Val Val Cys Ser Ser Gly Ala Val Gly Asn Tyr Ser
545                 550                 555                 560

Gly Gly Leu Ala Val Lys Glu Trp Leu Leu Ala His Glu Gly His Arg
                565                 570                 575

Leu Gly Lys Pro Gly Leu Gly Ser Ser Gly Leu Ala Gly Ala Trp
            580                 585                 590

Leu Lys Gly Ala Gly Ala Thr Ser Gly Ser Pro Pro Ala Gly Arg Asn
    595                 600                 605

<210> SEQ ID NO 46
<211> LENGTH: 608
<212> TYPE: PRT
<213> ORGANISM: Artificial Sequence
<220> FEATURE:
<223> OTHER INFORMATION: Synthetic construct

<400> SEQUENCE: 46

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
                20                  25                  30

Ser Pro Gly Pro Val Pro Ser Thr Ala Leu Arg Tyr Leu Ile Glu
            35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Gln
    130                 135                 140

Phe Asn Pro Arg Lys Pro Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Gln Leu Leu Cys Tyr Leu Leu Asp Gly Ile Leu Phe Ile Tyr Gly
        195                 200                 205

Val Ile Leu Thr Ala Leu Phe Leu Arg Val Val Thr Phe Trp Val Arg
    210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Thr Arg Lys Phe Ser Arg Ser Ala
            260                 265                 270

Asp Ala Pro Ala Tyr Gln Gln Gly Gln Asn Gln Leu Tyr Asn Glu Leu
```

275                 280                 285
Asn Leu Gly Arg Arg Glu Glu Tyr Asp Val Leu Asp Lys Arg Gly
    290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
            325                 330                 335

Glu Ile Gly Met Lys Gly Glu Arg Arg Arg Gly Lys Gly His Asp Gly
        340                 345                 350

Leu Tyr Gln Gly Leu Ser Thr Ala Thr Lys Asp Thr Tyr Asp Ala Leu
    355                 360                 365

His Met Gln Ala Leu Pro Pro Arg Gln Pro Ala Ala Ala Glu Gly Arg
370                 375                 380

Gly Ser Leu Leu Thr Cys Gly Asp Val Glu Glu Asn Pro Gly Pro Pro
385                 390                 395                 400

Trp Met Asp Lys Asp Cys Glu Met Lys Arg Thr Thr Leu Asp Ser Pro
            405                 410                 415

Leu Gly Lys Leu Glu Leu Ser Gly Cys Glu Gln Gly Leu His Glu Ile
        420                 425                 430

Lys Leu Leu Gly Lys Gly Thr Ser Ala Ala Asp Ala Val Glu Val Pro
    435                 440                 445

Ala Pro Ala Ala Val Leu Gly Gly Pro Glu Pro Leu Met Gln Cys Thr
450                 455                 460

Ala Trp Leu Asn Ala Tyr Phe His Gln Pro Glu Ala Ile Glu Glu Phe
465                 470                 475                 480

Pro Val Pro Ala Leu His His Pro Val Phe Gln Gln Glu Ser Phe Thr
            485                 490                 495

Arg Gln Val Leu Trp Lys Leu Leu Lys Val Val Lys Phe Gly Glu Val
        500                 505                 510

Ile Ser Tyr Gln Gln Leu Ala Ala Leu Ala Gly Asn Pro Lys Ala Ala
    515                 520                 525

Arg Ala Val Gly Gly Ala Met Arg Gly Asn Pro Val Lys Ile Leu Ile
530                 535                 540

Pro Cys His Arg Val Val Cys Ser Ser Gly Ala Val Gly Asn Tyr Ser
545                 550                 555                 560

Gly Gly Leu Ala Val Lys Glu Trp Leu Leu Ala His Glu Gly His Arg
            565                 570                 575

Leu Gly Lys Pro Gly Leu Gly Gly Ser Ser Gly Leu Ala Gly Ala Trp
        580                 585                 590

Leu Lys Gly Ala Gly Ala Thr Ser Gly Ser Pro Pro Ala Gly Arg Asn
    595                 600                 605

<210> SEQ ID NO 47
<211> LENGTH: 608
<212> TYPE: PRT
<213> ORGANISM: Artificial Sequence
<220> FEATURE:
<223> OTHER INFORMATION: Synthetic construct

<400> SEQUENCE: 47

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala Leu Arg Lys Leu Ile Glu

```
                35                  40                  45
Glu Leu Val Asn Ile Thr Gln Asn Gln Lys Ala Pro Leu Cys Asn Gly
 50                  55                  60

Ser Met Val Trp Ser Ile Asn Leu Thr Ala Gly Met Tyr Cys Ala Ala
 65                  70                  75                  80

Leu Glu Ser Leu Ile Asn Val Ser Gly Cys Ser Ala Ile Glu Lys Thr
                 85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Lys Glu Gly Gln
130                 135                 140

Phe Asn Pro Arg Lys Pro Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Gln Leu Leu Cys Tyr Leu Leu Asp Gly Ile Leu Phe Ile Tyr Gly
        195                 200                 205

Val Ile Leu Thr Ala Leu Phe Leu Arg Val Val Thr Phe Trp Val Arg
210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Thr Arg Lys Phe Ser Arg Ser Ala
            260                 265                 270

Asp Ala Pro Ala Tyr Gln Gln Gly Gln Asn Gln Leu Tyr Asn Glu Leu
        275                 280                 285

Asn Leu Gly Arg Arg Glu Glu Tyr Asp Val Leu Asp Lys Arg Arg Gly
290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
            340                 345                 350

Leu Tyr Gln Gly Leu Ser Thr Ala Thr Lys Asp Thr Tyr Asp Ala Leu
        355                 360                 365

His Met Gln Ala Leu Pro Pro Arg Gln Pro Ala Ala Ala Glu Gly Arg
370                 375                 380

Gly Ser Leu Leu Thr Cys Gly Asp Val Glu Glu Asn Pro Gly Pro Pro
385                 390                 395                 400

Trp Met Asp Lys Asp Cys Glu Met Lys Arg Thr Thr Leu Asp Ser Pro
                405                 410                 415

Leu Gly Lys Leu Glu Leu Ser Gly Cys Glu Gln Gly Leu His Glu Ile
            420                 425                 430

Lys Leu Leu Gly Lys Gly Thr Ser Ala Ala Asp Ala Val Glu Val Pro
        435                 440                 445

Ala Pro Ala Ala Val Leu Gly Gly Pro Glu Pro Leu Met Gln Cys Thr
450                 455                 460
```

Ala Trp Leu Asn Ala Tyr Phe His Gln Pro Glu Ala Ile Glu Glu Phe
465                 470                 475                 480

Pro Val Pro Ala Leu His His Pro Val Phe Gln Gln Glu Ser Phe Thr
            485                 490                 495

Arg Gln Val Leu Trp Lys Leu Leu Lys Val Val Lys Phe Gly Glu Val
        500                 505                 510

Ile Ser Tyr Gln Gln Leu Ala Ala Leu Ala Gly Asn Pro Lys Ala Ala
            515                 520                 525

Arg Ala Val Gly Gly Ala Met Arg Gly Asn Pro Val Lys Ile Leu Ile
        530                 535                 540

Pro Cys His Arg Val Val Cys Ser Ser Gly Ala Val Gly Asn Tyr Ser
545                 550                 555                 560

Gly Gly Leu Ala Val Lys Glu Trp Leu Leu Ala His Glu Gly His Arg
            565                 570                 575

Leu Gly Lys Pro Gly Leu Gly Gly Ser Ser Gly Leu Ala Gly Ala Trp
        580                 585                 590

Leu Lys Gly Ala Gly Ala Thr Ser Gly Ser Pro Pro Ala Gly Arg Asn
        595                 600                 605

<210> SEQ ID NO 48
<211> LENGTH: 621
<212> TYPE: DNA
<213> ORGANISM: Artificial Sequence
<220> FEATURE:
<223> OTHER INFORMATION: Synthetic construct

<400> SEQUENCE: 48
atggacaaag attgcgagat gaagcggacc acactggact cccccctggg caaactggag      60
ctgtctggct gtgaacaggg gctgcacgag atcaaactgc tgggaaaggg cactagcgcc     120
gctgatgctg tggaagtgcc agctccagct gctgtgctgg aggacctga gccactgatg      180 cagtgcaccg cctggctgaa cgcttacttc catcagcctg aagccatcga ggaatttccc     240
gtgcctgccc tgcaccatcc agtgttccag caggagagtt ttacaaggca ggtgctgtgg     300
aagctgctga agtggtgaa gttcggggaa gtgatttcct accagcagct ggctgctctg     360
gctggaaacc caaaagctgc tcgggccgtg gaggagcta tgagaggcaa tccagtgcca     420
atcctgattc cctgccacag ggtggtgtgt agctccggag ctgtggggaa ctattctggg     480
ggactggccg tgaaagaatg gctgctggct cacgagggac ataggctggg aaagcctggc     540 ctggagggt ctagtggact ggctggagct tggctgaagg gagctggagc tacctcagga      600
agcccacctg ccggccggaa t                                                621

<210> SEQ ID NO 49
<211> LENGTH: 207
<212> TYPE: PRT
<213> ORGANISM: Homo sapiens

<400> SEQUENCE: 49

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Cys Thr Ala
    50                  55                  60

```
Trp Leu Asn Ala Tyr Phe His Gln Pro Glu Ala Ile Glu Glu Phe Pro
 65                  70                  75                  80

Val Pro Ala Leu His His Pro Val Phe Gln Gln Glu Ser Phe Thr Arg
                     85                  90                  95

Gln Val Leu Trp Lys Leu Leu Lys Val Val Lys Phe Gly Glu Val Ile
                100                 105                 110

Ser Tyr Gln Gln Leu Ala Ala Leu Ala Gly Asn Pro Lys Ala Ala Arg
            115                 120                 125

Ala Val Gly Gly Ala Met Arg Gly Asn Pro Val Pro Ile Leu Ile Pro
        130                 135                 140

Cys His Arg Val Val Cys Ser Ser Gly Ala Val Gly Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
                180                 185                 190

Lys Gly Ala Gly Ala Thr Ser Gly Ser Pro Pro Ala Gly Arg Asn
            195                 200                 205
```